United States Patent [19]
Johnston-Dow et al.

[11] Patent Number: 6,103,465
[45] Date of Patent: Aug. 15, 2000

[54] METHODS AND REAGENTS FOR TYPING HLA CLASS I GENES

[75] Inventors: Leslie Johnston-Dow, Palo Alto, Calif.; Robert B. Chadwick, Dublin, Ohio; Peter Parham, Stanford, Calif.

[73] Assignee: The Perkin-Elmer Corporation, Foster City, Calif.

[21] Appl. No.: 08/538,666

[22] Filed: Oct. 3, 1995

Related U.S. Application Data

[63] Continuation-in-part of application No. 08/390,251, Feb. 14, 1995, abandoned.

[51] Int. Cl.$^7$ .............................. C12Q 1/68; C07H 21/02
[52] U.S. Cl. .............................................. 435/6; 536/23.1
[58] Field of Search ........................ 435/6, 91.2; 935/77, 935/78; 536/23.1

[56] References Cited

U.S. PATENT DOCUMENTS

| | | | |
|---|---|---|---|
| 4,358,535 | 11/1982 | Falkow et al. .............................. | 435/5 |
| 4,683,195 | 7/1987 | Mullis et al. . | |
| 4,683,202 | 7/1987 | Mullis . | |
| 4,855,225 | 8/1989 | Fung et al. . | |
| 5,424,184 | 6/1995 | Santamaria et al. ......................... | 435/6 |
| 5,451,512 | 9/1995 | Apple et al. ............................ | 435/91.2 |

FOREIGN PATENT DOCUMENTS

| | | |
|---|---|---|
| 0540997A1 | 5/1993 | European Pat. Off. . |
| WO92/01675 | 9/1992 | WIPO . |
| WO 92/19771 | 11/1992 | WIPO . |
| WO92/01679 | 11/1992 | WIPO . |
| WO92/118396 | 5/1993 | WIPO . |

OTHER PUBLICATIONS

Fernandex–Vina et al., Human Immunology 33: 163–173 (1992), DNA typing for HLA class I Alleles: I. Subsets of HLA–A2 and of –A28.
Allen et al., Human Immunology 40: 25–32 (1994), A comprehensive polymerase chain reaction–oligonucleotide typing system for the HLA class I A locus.
Guttridge et al., Tissue Antigens 44: 43–46 (1994), Identification of HLA–B35, B53, B18, B5, B78, and B17 alleles by the polymerase chain reaction using sequence–specific primers (PCR–SSP).
Yoshida et al., Human Immunology 34: 257–266 (1992), Polymerase–chain–reaction–based analysis of polymorphism in the HLA–B gene.
Dominguez et al., Immunogenetics 36: 277–282 (1992), Molecular typing of HLA–B27 alleles.
Andrien et al., Tissue Antigens 42: 480–487 (1993), HLA–B locus DNA typing: detection of B*7801 and seven additional alleles by BW6–specific exon 2 amplification.
Bunce et al., Tissue Antigens 43: 7–17 (1994), Rapid DNA typing for HLA–C using sequence–specific primers(PCR__SSP): identification of serologically defined HLA–C alleles including several new alleles.
Janeway Jr., Scientific American, Sep., 73–79 (1993), How the immune system recognizes invaders.

Petersdorf et al., Tissue Antigens 44: 93–99 (1994), Molecular diversity of the HLA–C locus in unrelated marrow transplantation.
Santamaria et al., Human Immunology 33: 69–81 (1992), HLA class II "typing": direct sequencing of DRB, DQB, and DQA genes.
Santamaria et al., Human Immunology 37: 39–50 (1993), HLA class I sequence–based typing.
Petersdorf et al., Tissue Antigens 44: 211–216 (1994), Analysis of HLA–B*44 alleles encoded on extended HLA haplotypes by direct automated sequencing.
Cereb et al., Tissue Antigens 45: 1–11 (1995), Locus–specific amplification of HLA class I genes from genomic DNA: locus–specific sequences in the first and third introns of HLA–A, –B, and –C alleles.
Gelfand and White, PCR Protocols: A Guide to Methods and Applications, ed., Innis et al., Academic Press, CA, pp. 129–141 (1991), Thermostable DNA polymerases.
Chou et al, Nucleic Acids Research 20(7):1717–23 (1992) Prevention of pre–PCR mis–priming and primer dimerization improves low–copy–number amplifications.
Engelke et al., Proceedings of the National Academy of Sciences 85: 544–548 (1988), Direct sequencing of enzymatically amplified human genomic DNA.
McBride et al., Clinical Chemistry 35(11): 2196–2201 (1989), Automated DNA sequencing methods involving polymerase chain reaction.
Gorman et al., BioTechniques 7(4): 326–329 (1989), Simplified method for selective amplification and direct sequencing of cDNAs.
Trowsdale et al., Immunology Today 12(12): 443–446 (1991), Map of the human MHC.
Miller et al., Nucleic Acids Research 16(3): 9–10 (1988), A simple salting out procedure for extracting DNA from human nucleated cells.
Geraghty, Proceedings of the Eleventh International Histocompatibility Workshop and Conference vol. 2, Tsuji et al. eds., pp. 129–132, Oxford University Press (1992), The HLA class I gene family.
Applied Biosystems, 373A DNA Sequencing System User's Manual, Part No. 901156, Software Version 1.10, Document Rev. C, Jan. 1992.

(List continued on next page.)

*Primary Examiner*—Eggerton A. Campbell
*Attorney, Agent, or Firm*—Paul D. Grossman

[57] ABSTRACT

A method for typing HLA class 1 genes. The method entails first contacting a sample DNA with first and second amplification primers, wherein the first and second primers are each at least partially located in an exonic region. Next, using the first and second primers, a target sequence is amplified by the PCR to form an amplicon of the target sequence. Finally, the amplicon is detected with a sequence-specific detection means, e.g., DNA sequencing. The invention also includes specific amplification primers, specific sequencing primers, and kits especially adapted for use with the above HLA typing method.

41 Claims, 39 Drawing Sheets

OTHER PUBLICATIONS

Holtz et al., DNA–Technology and Its Forensic Application, Berghaus et al. eds., pp. 79–84, Springer–Verlag, Berlin (1991), DNA Typing Using PCR Amplified Fragments in the HLA Class I Region.

Lee et al., Nucleic Acids Research 20(10): 2471–2483 (1992), DNA sequencing with dye–labeled terminators and T7 polymerase: effect of dyes and dNTPs on incorporation of dye–terminators and probability analysis of termination fragments.

Prober et al., Science 238: 336–341 (1987), A system for rapid DNA sequencing with fluorescent chain–terminating, dideoxynucleotides.

Lawyer et al., J. Biol. Chem. 264:6427–6437 (1989), Isolation, characterization, and expression in *Escherichia Coli* of the DNA polymerase gene from *Thermus aquaticus*.

Krausa, P. et al., Tissue Antigens, 45(4): 223–31 (Apr. 1995), Genetic Polymorphism within HLA–A *02: significant allelic variation revealed in different populations.

Blasczyk, R. et al., Tissue Antigens, 46(2): 86–95 (Aug. 1995), Complete subtyping of the HLA–A locus by sequence-specific amplification followed by direct sequencing or single–strand conformation polymorphism analysis.

Kennedy, L. J. et al., Tissue Antigens, 46(2): 187–195 (1995), Definition of HLA–C alleles using sequence-specific oligonucleotide probes (PCR–SSOP).

```
HLA-A1 exon 2.layout   2/8/94   1:21 PM
                        10         20         30         40         50         60
1 HLA-A1         GCTCCCACTC CATGAGGTAT TTCTTCACAT CCGTGTCCCG GCCCGGCCGC GGGGAGCCCC
2 18Jan95 01    CNKKBENGCN GANGAGGAST TATTGSACAT CCGTGTCCCG GCCCGGCCGC GGGGAGCCCC
3E 18Jan95 03   GCTCCCACTC CATGAGGTAT TTCTTCACAT CCGTGTCCCG GCCCGGCCGC GGGGAGCCCC
4 consensus     gctcccactc cAtGAGGtaT TtcTtcACAT CCGTGTCCCG GCCCGGCCGC GGGGAGCCCC 70         80         90        100        110        120
1 HLA-A1         GCTTCATCGC CGTGGGCTAC GTGGACGACA CGCAGTTCGT GCGGTTCGAC AGCGACGCCG
2 18Jan95 01    GCTTCATCGC CGTGGGCTAC GTGGACGACA CGCAGTTCGT GCGGTTCGAC AGCGACGCCG
3E 18Jan95 03   GCTTCATCGC CGTGGGCTAC GTGGACGACA CGCAGTTCGT GCGGTTCGAC AGCGACGCCG
4 consensus     GCTTCATCGC CGTGGGCTAC GTGGACGACA CGCAGTTCGT GCGGTTCGAC AGCGACGCCG 130        140        150        160        170        180
1 HLA-A1         CGAGCCAGAA GATGGAGCCG CGGGCGCCGT GGATAGAGCA GGAGGGGCCG GAGTATTGGG
2 18Jan95 01    CGAGCCAGAA GATGGAGCCG CGGGCGCCGT GGATAGAGCA GGAGGGGCCG GAGTATTGGG
3E 18Jan95 03   CGAGCCAGAA GATGGAGCCG CGGGCGCCGT GGATAGAGCA GGAGGGGCCG GAGTATTGGG
4 consensus     CGAGCCAGAA GATGGAGCCG CGGGCGCCGT GGATAGAGCA GGAGGGGCCG GAGTATTGGG 190        200        210        220        230        240
1 HLA-A1         ACCAGGAGAC ACGGAATATG AAGGCCCACT CACAGACTGA CCGAGCGAAC CTGGGGACCC
2 18Jan95 01    ACCAGGAGAC ACGGAATATG AAGGCCCACT CACAGACTGA CCGAGCGAAC CTGGGGACCC
3E 18Jan95 03   ACCaGGAGAC ACGGAATATG aAGGCCCACT CACAGACTGA CCGAGCGAAC CTGGGGACCC
4 consensus     ACCAGGAGAC ACGGAATATG AAGGCCCACT CACAGACTGA CCGAGCGAAC CTGGGGACCC 250        260        270        280        290        300
1 HLA-A1         TGCGCGGCTA CTACAACCAG AGCGAGGACG
2 18Jan95 01    TGCGCGGCTA CTACAACCAG AGCGAGGAC
3E 18Jan95 03   tGCGCGGCT-  ---------- ----------
4 consensus     TGCGCGGCTa ctacaaccag agcgaggacG
```

Fig. 5

```
HLA-A exon 3.layout  2/8/94  1:23 PM
                           10         20         30         40         50         60
                           |          |          |          |          |          |
1  HLA-A1         GTTCTCACAC CATCCAGATA ATGTATGGCT GCGACGTGGG GCCGGACGGG CGCTTCCTCC
4  18Jan95  02   CTTTAANCAC CANCSAGNTA ATGNATGNCT GCGACGNAGG NCCGGANNNN GGTGTNCTGT
5E 18Jan95  04   GTTCTCACAC CATCCAGATA ATGTATGGCT GCGACGTGGG GCCGGACGGG CGCTTCCTCC
7  consensus     gTTctcaCAC CATCcAGaTA ATGtATGgCT GCGACGTgGG gCCGGAcggg cGctTcCTcc 70         80         90        100        110        120
                           |          |          |          |          |          |
1  HLA-A1         GCGGGTACCG GCAGGACGCC TACGACGGCA AGGATTACAT CGCCCTGAAC GAGGACCTGC
4  18Jan95  02   TNLCNTACCG NCAGGACGCC TACGACGGCA AGGATTACAT CGCCCTGAAC GAGGACCTGC
5E 18Jan95  04   GCGGGTACCG GCAGGACGCC TACGACGGCA AGGATTACAT CGCCCTGAAC GAGGACCTGC
7  consensus     gcgggTACCG gCAGGACGCC TACGACGGCA AGGATTACAT CGCCCTGAAC GAGGACCTGC 130        140        150        160        170        180
                           |          |          |          |          |          |
1  HLA-A1         GCTCTTGGAC CGCGGCGGAC ATGGCAGCTC AGATCACCAA GCGCAAGTGG GAGGCGGTCC
4  18Jan95  02   GCTCTTGGAC CGCGGCGGAC ATGGCAGCTC AGATCACCAA GGGCAAGTGG GAGGCGGTCC
5E 18Jan95  04   GCTCTTGGAC CGCGGCGGAC ATGGCAGCTC AGATCACCAA GCGCAAGTGG GAGGCGGTCC
7  consensus     GCTCTTGGAC CGCGGCGGAC ATGGCAGCTC AGATCACCAA GcGCAAGTGG GAGGCGGTCC 190        200        210        220        230        240
                           |          |          |          |          |          |
1  HLA-A1         ATGCGGCGGA GCAGCGGAGA GTCTACCTGG AGGGCCGGTG CGTGGACGGG CTCCGCAGAT
4  18Jan95  02   ATGCGGCGGA gCAGCGGAGA GTCTACCTGG AGGGCCGGTG CGTGGACGGG CTCCGCAGAT
5E 18Jan95  04   ATGCGGCGGA GCAgCGGAGA GTCTACCTGG AGGGCCGGTG CGTGGACGGg CTCCGCAGAT
7  consensus     ATGCGGCGGA GCAgCGGAGA GTCTACCTGG AGGGCCGGTG CGTGGACGGg CTCCGCAGAT 250        260        270        280        290        300
                           |          |          |          |          |          |
1  HLA-A1         ACCTGGAGAA CGGGAAGGAG ACGCTGCAGC GCACGG
4  18Jan95  02   ACCTGGAGAA CGGGAAGGAG ACGCTGCAAA GCACGG
5E 18Jan95  04   ACCTGGAGAA CGGSNAGSAG ACN-TGNAA- GCNNNN
7  consensus     ACCTGGAGAA CGGgaAGgAG ACgcTGcAam GCacgg
```

Fig. 8

HLA-B exon 2.layout 2/8/95 1:35 PM

```
                    10         20         30         40         50         60
1 HLA-B 0801 GGCTCCCACT CCATGAGGTA TTTCGACACC GCCATGTCCC GGCCCGGCCG CGGGGAGCCC
2 18Jan95 05 NN-------- ----GGaGgN TTTcGnCACC GCCATGTCCC GGCCCGGC_G CGGGGAGCCC
3E 18Jan95 07 GGCTCCCACT CCATGAGGTA TTTcGACACC GCCATGTCCC GGcCCGGCCG CGGGGAGCCC
8 consensus  ggctcccact ccatGagGta TTTCGaCACC GCCATGTCCC GGCCCGGCCG CGGGGAGCCC 70         80         90         100        110        120
1 HLA-B 0801 CGCTTCATCT CAGTGGGCTA CGTGGACGAC ACGCAGTTCG TGAGGTTCGA CAGCGACGCC
2 18Jan95 05 cgCTTCATCT CAGTGGGCTA CGTGGACGAC ACGCAgTTCG TGAGGTTCGA CAGCGACGCC
3E 18Jan95 07 CGCTTCATCT CAGTGGGCTA CGTGGACGAC ACGCAGTTCG TGAGGTTCGA CAgCGACGCC
8 consensus  CGCTTCATCT CAGTGGGCTA CGTGGACGAC ACGCAGTTCG TGAGGTTCGA CAGCGACGCC 130        140        150        160        170        180
1 HLA-B 0801 GCGAGTCCGA GAGAGGAGCC GCGGGCGCCG TGGATAGAGC AGGAGGGGCC GGAGTATTGG
2 18Jan95 05 GCGAGTCCGA GAGAGGAGCC GCGGGCGCCG TGGATAGAGC AGGAGGGGCC GGAGTATTGG
3E 18Jan95 07 GCGAGTCCGA GAGAGGAGCC GCGGGCGCCG TGGATAGAGC AGGAGGGGCC GGAGTATTGG
8 consensus  GCGAGTCCGA GAGAGGAGCC GCGGGCGCCG TGGATAGAGC AGGAGGGGCC GGAGTATTGG 190        200        210        220        230        240
1 HLA-B 0801 GACCGGAACA CACAGATCTT CAAGACCAAC ACACAGACTG ACCGAGAGAG CCTGCGGAAC
2 18Jan95 05 GACCGkAACA CAcAGATCTT CAAGACCAAC ACACAGACTk ACCGAaAGAG CCTkCGGAAC
3E 18Jan95 07 GACCGGAACA CACAGATCTT _AAGACCAAC ACACAGACTG _CCGAGAGAG C-TGCGGAAC
8 consensus  GACCGgAACA CACAGATCTT CAAGACCAAC ACACAGACTg ACCGAGAGAG CcTgCGGAAC 250        260        270        280        290        300
1 HLA-B 0801 CTGCGCGGCT ACTACAACCA GAGCGAGGCC
2 18Jan95 05 CTGCGcGGCT ACTACAACCA GAGCGAGGCC
3E 18Jan95 07 -TGCGCGGCT ---------- ----------
8 consensus  cTGCGcGGCT actacaacca gagcgaggcc
```

Fig. 11

```
HLA-B exon 3.layout  2/8/95  1:33 PM
                         10         20         30         40         50         60
1 HLA-B 0801  GGTCTCACAC CCTCCAGAGC ATGTACGGCT GCGACGTGGG GCCGGACGGG CGCCTCCTCC
2 18Jan95 08  GGTCTCACAC CCTCCAGAGC ATGTACGGCT GCGACGTGGG GCCGGACGGG CGCCTCCTCC
3 consensus   GGTCTCACAC CCTCCAGAGC ATGTACGGCT GCGACGTGGG GCCGGACGGG CGCCTCCTCC 70         80         90        100        110        120
1 HLA-B 0801  GCGGGCATAA CCAGTACGCC TACGACGGCA AGGATTACAT CGCCCTGAAC GAGGACCTGC
2 18Jan95 08  GCGGGCATAA CCAGTACGCC TACGACGGCA AGGATTACAT CGCCCTGAAC GAGGACCTGC
3 consensus   GCGGGCATAA CCAGTACGCC TACGACGGCA AGGATTACAT CGCCCTGAAC GAGGACCTGC 130        140        150        160        170        180
1 HLA-B 0801  GCTCCTGGAC CGCGGCGGAC ACCGCGGCTC AGATCACCCA GCGCAAGTGG GAGGCGGCCC
2 18Jan95 08  GCTCCTGGAC CGCGnCGGAC ACCGCGGCTC AGATCACCCA GCGCAAGTGG GAGGCGGCCC
3 consensus   GCTCCTGGAC CGCGnCGGAC ACCGCGGCTC AGATCACCCA GCGCAAGTGG GAGGCGGCCC 190        200        210        220        230        240
1 HLA-B 0801  GTGTGGCGGA GCAGGACAGA GCCTACCTGG AGGGCACGTG CGTGGAGTGG CTCCGCAGAT
2 18Jan95 08  GTGTGGCGGA GCAGGACAGA GCCTACCTGG AGGGCaCGTG CGTGGAGTG- CTCCGCAGAT
3 consensus   GTGTGGCGGA GCAGGACAGA GCCTACCTGG AGGGCACGTG CGTGGAGTGg CTCCGCAGAT 250        260        270        280        290        300
1 HLA-B 0801  ACCTGGAGAA CGGGAAGGAC ACGCTGGAGC GCGCGGAC
2 18Jan95 08  ACCTGGAGAA CGGGAAGGAC AC-CTGSAGM NAMMCMCS
3 consensus   ACCTGGAGAA CGGGAAGGAC ACgCTGsAGm nmnvsvms
```

Fig. 13

```
HLA-B exon 4 .layout  2/8/95  1:33 PM
                            10         20         30         40         50         60
 6 HLA-B 0801 CCCCCCAAAG ACACACGTGA CCCACCACCC CATCTCTGAC CATGAGGCCA CCCTGAGGTG
 8 02FEB95 25 TTTTA--- --AMACSNGM CCCAccACCc CATTTCTGAC CATGAGGCCA CCCTGAGGTG
 9E 02FEB95 26 CCCMCCAAAG ACACACGTGA CCCACCaCCC CATCTCTGAC CATSAGGCCA MCCTgaCgTG
11 consensus  CCcnccAaag acAcACgtGa CCCACCACCC CATCTCTGAC CATgAGGCCA cCCTGAGGTG 70         80         90        100        110        120
 6 HLA-B 0801 CTGGGCCCTG GGCTTCTACC CTGCGGAGAT CACACTGACC TGGCAGCGGG ATGGCGAGGA
 8 02FEB95 25 CTGGGCCCTG GGCTTCTACC CTGCGGAGAT CACACTGACC TGGCAGCGGG ATGGCGAGGA
 9E 02FEB95 26 cTgCGCCCTG GGCTTCTACc CTGCGGAGAT CACACTGACC TGGCaCCGGG ATGGCGAGGA
11 consensus  CTGGGCCCTG GGCTTCTACC CTGCGGAGAT CACACTGACC TGGCAGCGGG ATGGCGAGGA 130        140        150        160        170        180
 6 HLA-B 0801 CCAAACTCAG GACACTGAGC TTGTGGAGAC CAGACCAGCA GGAGATAGAA CCTTCCAGAA
 8 02FEB95 25 CCAAACTCAG GMCACTVMRC TTGTGSnNaC CAGACCAGCA GGAGATAGAA CCTTCCAGAA
 9E 02FEB95 26 CCAAACWCAG GACACTGAGC TTGTGGAGAC CAGACCAGCA GGAGATAGAA CCtTCCAGAA
11 consensus  CCAAACtCAG GaCACTgagC TTGTGgagaC CAGACCAGCA GGAGATAGAA CCTTCCAGAA 190        200        210        220        230        240
 6 HLA-B 0801 GTGGGCAGCT GTGGTGGTGC CTTCTGGAGA AGAGCAGAGA TACACATGCC ATGTACAGCA
 8 02FEB95 25 GTGGGCAGCT GTGGTGGTGC CTTCTGGAGA AGAGCAGAGA TACACATGCC ATGTACAGCA
 9E 02FEB95 26 GTGGGCAGCT GTGGTGGTGC CTTCTGGAGK AAGYAG---T CAGBAGCATC ACAMAWGCCS
11 consensus  GTGGGCAGCT GTGGTGGTGC CTTCTGGAGa Agagcagaga tAcacatgcC AtgtAcagCa 250        260        270        280        290        300
 6 HLA-B 0801 TGAGGGGCTG CCGAAGCCCC TCACCCTGAG ATGG
 8 02FEB95 25 TGAGGGGCTG CCGAAGCCCC TCACCCTGAG ATGG
 9E 02FEB95 26 KVHGKMMGG
11 consensus  tgaGgggctG CCGAAGCCCC TCACCCTGAG ATGG
```

Fig. 16

```
HLA-Cw1701/BM21 exon 2  2/8/95        PM
                  10         20         30         40         50
                  |          |          |          |          |
 1 C1701-EX2    GCTCCCACTC CATGAGGTAT TTCTACACCG CCGTGTCCCG GCCCGGCCGC
 3 BM21-C1-3.6  GCTCCCACTC CATGAGGTAT TTCTACACCG CCGTGTCCCG GCCCGGCCGC
10 BM21-C1-5.4                                   CGTGTCCCG GCCCGGCCGC
11 consensus    gctcccactc catgaggtat ttctacaccg cCGTGTCCCG GCCCGGCCGC 60         70         80         90        100
                  |          |          |          |          |
 1 C1701-EX2    GGAGAGCCCC GCTTCATCGC AGTGGGCTAC GTGGACGACA CGCAGTTCGT
 3 BM21-C1-3.6  GGAGAGCCCC GCTTCATCGC AGTGGGCTAC GTGGACGACA CGCAGTTCGT
10 BM21-C1-5.4  GGAGAGCCCC GCTTCATCGC AGTGGGCTAC GTGGACGACA CGCAGTTCGT
11 consensus    GGAGAGCCCC GCTTCATCGC AGTGGGCTAC GTGGACGACA CGCAGTTCGT 110        120        130        140        150
                  |          |          |          |          |
 1 C1701-EX2    GCGGTTCGAC AGCGACGCCG CGAGTCCGAG AGGGGAGCCG CGGGCGCCGT
 3 BM21-C1-3.6  GCGGTTCGAC AGCGACGCCG CGAGTCCGAG AGGGGAGCCG CGGGCGCCGT
10 BM21-C1-5.4  GCGGTTCGAC AGCGACGCCG CGAGTCCGAG AGGGGAGCCG CGGGCGCCGT
11 consensus    GCGGTTCGAC AGCGACGCCG CGAGTCCGAG AGGGGAGCCG CGGGCGCCGT 160        170        180        190        200
                  |          |          |          |          |
 1 C1701-EX2    GGGTGGAGCA GGAGGGGCCG GAGTATTGGG ACCGGGAGAC ACAGAAGTAC
 3 BM21-C1-3.6  GGGTGGAGCA GGAGGGGCCG GAGTATTGGG ACCGGGAGAC ACAGAAGTAC
10 BM21-C1-5.4  GGGTGGAGCA GGAGGGGCCG GAGTATTGGG ACCGGGAGAC ACAGAAGTAC
11 consensus    GGGTGGAGCA GGAGGGGCCG GAGTATTGGG ACCGGGAGAC ACAGAAGTAC 210        220        230        240        250
                  |          |          |          |          |
 1 C1701-EX2    AAGCGCCAGG CACAGGCTGA CCGAGTGAAC CTGCGGAAAC TGCGCGGCTA
 3 BM21-C1-3.6  AAGCGCCAGG CACAGGCTGA CCGAGTGAAC cTGCGGAAAC TGCG
10 BM21-C1-5.4  AAGCGCCAGG CACAGGCTGA CCGAGTGAAC CTGCGGAAAC TGCGCGGCTA
11 consensus    AAGCGCCAGG CACAGGCTGA CCGAGTGAAC CTGCGGAAAC TGCGCGGCTA 260        270        280        290        300
                  |          |          |          |          |
 1 C1701-EX2    CTACAACCAG AGCGAGGCCG
 3 BM21-C1-3.6  <==
10 BM21-C1-5.4  CTACAACCAG AGCGAGGCCG GTGAGTGACC CCC
11 consensus    CTACAACCAG AGCGAGGCCG GTGAGTGACC CCC
```

Fig. 19

HLA-Cw1701/BM21 exon 3   2/8/95

|              | 10         20         30         40         50 |
|---|---|
| 1 C1701-EX3  | GTTCTCACAC CATCCAGAGG ATGTATGGCT GCGACCTGGG GCCCGACGGG |
| 2E BM21-C1-3.7 | GTTCTCACAC CATCCAGAGG ATGTATGGCT GCGACCTGGG GCCCGACGGG |
| 4 consensus  | GTTCTCACAC CATCCAGAGG ATGTATGGCT GCGACCTGGG GCCCGACGGG |
|              | 60         70         80         90         100 |
| 1 C1701-EX3  | CGCCTCCTCC GCGGGTATAA CCAGTTCGCC TACGACGGCA AGGATTACAT |
| 2E BM21-C1-3.7 | CGCCTCCTCC GCGGGTATAA CCAGTTCGCC TACGACGGCA AGGATTACAT |
| 4 consensus  | CGCCTCCTCC GCGGGTATAA CCAGTTCGCC TACGACGGCA AGGATTACAT |
|              | 110        120        130        140        150 |
| 1 C1701-EX3  | CGCCCTGAAC GAGGACCTGC GCTCCTGGAC CGCGGCGGAC ACGGCGGCTC |
| 2E BM21-C1-3.7 | CGCCCTGAAC GAGGACCTGC GCTCCTGGAC CGCGGCGGAC ACGGCGGCTC |
| 4 consensus  | CGCCCTGAAC GAGGACCTGC GCTCCTGGAC CGCGGCGGAC ACGGCGGCTC |
|              | 160        170        180        190        200 |
| 1 C1701-EX3  | AGATCTCCCA GCGCAAGTTG GAGGCGGCCC GTGAGGCGGA GCAGCTGAGA |
| 2E BM21-C1-3.7 | AGATCTCCCA GCGCAAGTTG GAGGCGGCCC GTGAGGCGGA GCAGCTGAGA |
| 4 consensus  | AGATCTCCCA GCGCAAGTTG GAGGCGGCCC GTGAGGCGGA GCAGCTGAGA |
|              | 210        220        230        240        250 |
| 1 C1701-EX3  | GCCTACCTGG AGGGCGAGTG CGTGGAGTGG CTCCGCGGAT ACCTGGAGAA |
| 2E BM21-C1-3.7 | GCCTACCTGG AGGGCGAGTG CGTGGAGTGG CTCCGCGGAT ACCTGGAGAA |
| 4 consensus  | GCCTACCTGG AGGGCGAGTG CGTGGAGTGG CTCCGCGGAT ACCTGGAGAA |
|              | 260        270        280        290        300 |
| 1 C1701-EX3  | CGGGAAGGAG ACGCTGCAGC GCGCGG |
| 2E BM21-C1-3.7 | CGGGAAGGAG AC |
| 4 consensus  | CGGGAAGGAG ACGCTGCAGC GCGCGG |

Fig. 21

```
HLA-A(M7) exon2  9/25/94  11:01 AM
                  10         20         30         40         50         60
1 A*0202         GGCTCTCACT CCATGAGGTA TTTCTTCACA TCCGTGTCCC GGCCCGGCCG CGGGGAGCCC
2 A*0301         GGCTCCCACT CCATGAGGTA TTTCTTCACA TCCGTGTCCC GGCCCGGCCG CGGGGAGCCC
3 18july95 10    GgCTCYCACT CCATGAGGTA TTTCTTCACA TCCGTGTCCC GGCCCGGCCG CGGGGAGCCC
4 3Aug95 03      nnnNnnNACT CCATGAGGTA TTTCTTCACA TCCGTGTCCC GGCCCGGCCG CGGGGAGCCC
5                -----*---- ---------- ---------- ---------- ---------- ----------

70         80         90        100        110        120
1 A*0202         CGCTTCATCG CAGTGGGCTA CGTGGACGAC ACGCAGTTCG TGCGGTTCGA CAGCGACGCC
2 A*0301         CGCTTCATCG CCGTGGGCTA CGTGGACGAC ACGCAGTTCG TGCGGTTCGA CAGCGACGCC
3 18july95 10    CGCTTCATCG CMGTGGGCTA CGTGGACGAC ACGCAGTTCG TGCGGTTCGA CAGCGACGCC
4 3Aug95 03      CGCTTCATCG CmGTGGGCTA CGTGGACGAC ACGCAGTTCG TGCGGTTCGA CAGCGACGCC
5                ---------- --*------- ---------- ---------- ---------- ----------

130        140        150        160        170        180
1 A*0202         GCGAGCCGGA GGATGGAGCC GCGGGCGCCG TGGATAGAGC AGGAGGGTCC GGAGTATTGG
2 A*0301         GCGAGCCAGA GGATGGAGCC GCGGGCGCCG TGGATAGAGC AGGAGGGGCC GGAGTATTGG
3 18july95 10    GCGAGCCRGA GGATGGAGCC GCGGGCGCCG TGGATAGAGC AGGAGGGKCC GGAGTATTGG
4 3Aug95 03      GCGAGCCrGA GGATGGAGCC GCGGGCGCCG TGGATAGAGC AGGAGGGkCC GGAGTATTGG
5                -------*-- ---------- ---------- ---------- --------*-- ----------

190        200        210        220        230        240
1 A*0202         GACGGGGAGA CACGGAAAGT GAAGGCCCAC TCACAGACTC ACCGAGTGGA CCTGGGGACC
2 A*0301         GACCAGGAGA CACGGAATGT GAAGGCCCAG TCACAGACTG ACCGAGTGGA CCTGGGGACC
3 18july95 10    GACSRGGAGA CACGGAAWGT GAAGGCCCAS TCACAGACTS ACCGAGTGGA CCTGGGGACc
4 3Aug95 03      GACSrGGAGA CACGGAAwGT GAAGGCCCAs TCACAGACTs ACCGAGTGGA CCTGGGGACC
5                ---**----- -------*-- ---------* ---------* ---------- ----------

250        260        270        280        290        300
1 A*0202         CTGCGCGGCT ACTACAACCA GAGCGAGGCC G
2 A*0301         CTGCGCGGCT ACTACAACCA GAGCGAGGCC G
3 18july95 10    CLGCGCGGCT A
4 3Aug95 03      CTGCGCGGCT ACTACAACCA GAGCGAGGCC -
5                ---------- ---------- ---------- *
```

Fig. 24

```
HLA-A(M7) exon3  9/25/94  11:00 AM
                      10         20         30         40         50         60
                      |          |          |          |          |          |
1 A*0202        GGTTCTCACA CCCTCCAGAG GATGTATGGC TGCGACGTGG GGTCGGACTG GCGCTTCCTG
2 A*0301        GGTTCTCACA CCATCCAGAT AATGTATGGC TGCGACGTGG GGTCGGACGG GCGCTTCCTC
4 3Aug95 21     GGTTcTCACA CCmTCCAGAk rATGTATGGC TGCGACGTGG GGTCGGACkG GCGCTTCCTs
6£ 2Aug 01      GGTTCTCACA CCmTCCAGAk rATGTATGGC TGCGACGTGG GGTCGGACKG GCGCTTCCTS
7               ---------- --*------* *--------- ---------- --------*- ---------*

70         80         90        100        110        120
                      |          |          |          |          |          |
1 A*0202        CGCGGGTACC ACCAGTACGC CTACGACGGC AAGGATTACA TCGCCCTGAA AGAGGACCTG
2 A*0301        CGCGGGTACC GGCAGGACGC CTACGACGGC AAGGATTACA TCGCCCTGAA CGAGGACCTG
4 3Aug95 21     CGCGGGTACC rsCAGkACGC CTACGACGGC AAGGATTACA TCGCCCTGAA mGAGGACCTG
6£ 2Aug 01      CGCGGGTACC rSCAGKACGC CTACGACGGC AAGGATTACA TCGCCCTGAA MGAGGACCTG
7               ---------- **---*---- ---------- ---------- ---------- *---------

130        140        150        160        170        180
                      |          |          |          |          |          |
1 A*0202        CGCTCTTGGA CCGCGGCGGA CATGGCAGCT CAGACCACCA AGCACAAGTG GGAGGCGGCC
2 A*0301        CGCTCTTGGA CCGCGGCGGA CATGGCGGCT CAGATCACCA AGCGCAAGTG GGAGGCGGCC
4 3Aug95 21     CGCTCTTGGA CCGCGGCGGA CATGGCrGCT CAGAyCACCA AGCrCAAGTG GGAGGCGGCC
6£ 2Aug 01      CGCTCTTGGA CCGCGGCGGA CATGGCRGCT CAGAYCACCA AGCRCAAGTG GGAGGCGGCC
7               ---------- ---------- ------*--- ----*----- ---*------ ----------

190        200        210        220        230        240
                      |          |          |          |          |          |
1 A*0202        CATGTGGCGG AGCAGTGGAG AGCCTACCTG GAGGGCACGT GCGTGGAGTG GCTCCGCAGA
2 A*0301        CATGAGGCGG AGCAGTTGAG AGCCTACCTG GATGGCACGT GCGTGGAGTG GCTCCGCAGA
4 3Aug95 21     CATGwGGCGG AgCAGTkGAG AGCCTACCTG GAkGGCACGT GCGTGGAGTG GCTCCGCAGA
6£ 2Aug 01      CATGWGGCGG AGCAGTKGAG AGCCTACCTG GAKGGCACGT GCGTGGAGTG gCtCCGCAGA
7               ----*----- ------*--- ---------- ---*------ ---------- ----------

250        260        270        280        290        300
                      |          |          |          |          |          |
1 A*0202        TACCTGGAGA ACGGGAAGGA GACGCTGCAG CGCACGG
2 A*0301        TACCTGGAGA ACGGGAAGGA GACGCTGCAG CGCACGG
4 3Aug95 21     TACCTGGAGA ACGGGAAGGA GACGCTGCAG cgcacgg
6£ 2Aug 01      TACCTGGAGA ACGGGAAGGA GACGCTGCAG CGCACGG
7               ---------- ---------- ---------- -------
```

Fig. 27

```
HLA-B(32511) exon2  9/25/94  2:01 PM
                        10         20         30         40         50         60
                        |          |          |          |          |          |
19 B*1801       GGCTCCCACT CCATGAGGTA TTTCCACACC TCCGTGTCCC GGCCCGGCCG CGGGGAGCCC
20 B*27052      GGCTCCCACT CCATGAGGTA TTTCCACACC TCCGTGTCCC GGCCCGGCCG CGGGGAGCCC
14 19June95  18 ---------- --ArgaGgtA TttcCACACC TCCGTGtCCC GGCCCGGCCG CgGGGAGCCC
16E 09June95 02 GGCTCCCACT CCaTGAGGTA TTTcCACACc TCCGTGTCCC GGCCCGGCCG CGGGGAgCCC
21              ********** **-------- ---------- ---------- ---------- ----------

70         80         90        100        110        120
                        |          |          |          |          |          |
19 B*1801       CGCTTCATCT CAGTGGGCTA CGTGGACGGC ACCCAGTTCG TGAGGTTCGA CAGCGACGCC
20 B*27052      CGCTTCATCA CCGTGGGCTA CGTGGACGAC ACGCTGTTCG TGAGGTTCGA CAGCGACGCC
14 19June95  18 CgcTTCATCw CMGTGGGCTA CGTGGACGEC ACsCMGTTCG TGAGGTTCGA CAGCGACGCC
16E 09June95 02 CGCTTCATCw CMGTGGGCTA CGTGGACGrM acsCMGTTCg TGAGGTTCGA CAGCGACGCC
21              ---------* -*-------- ---------* --*-*----- ---------- ----------

130        140        150        160        170        180
                        |          |          |          |          |          |
19 B*1801       GCGAGTCCGA GGACGGAGCC CCGGGCGCCG TGGATAGAGC AAGAGGGGCC GGAGTATTGG
20 B*27052      GCGAGTCCGA GAGAGGAGCC GCGGGCGCCG TGGATAGAGC AGGAGGGGCC GGAGTATTGG
14 19June95  18 GCGAGTCCGA GRRMGGAGCC sCGGGCGCCG TGGATAGAGC AMGAGGGGCC GGAGTATTGG
16E 09June95 02 GCGAgTCCGA GRRMGgAGCC sCGGGCGCCG TGGATAGAGC AMGAGGGGCC GGAGTATTGG
21              ---------- -*****---- *--------- ---------- -*-------- ----------

190        200        210        220        230        240
                        |          |          |          |          |          |
19 B*1801       GACCGGAACA CACAGATCTC CAAGACCAAC ACACAGACTT ACCGAGAGAG CCTGCGGAAC
20 B*27052      GACCGGGAGA CACAGATCTG CAAGGCCAAG GCACAGACTG ACCGAGAGGA CCTGCGGACC
14 19June95  18 GACCGGrASA CACAGATCTS CAAGrCCAAS RCACAGACTK ACCGAGAGRR CCTGCGGAMC
16E 09June95 02 GACCGGRASA CACAGATCTS CAAGRCCAAS RCACAGACTK ACCGAGAGRR CcTGCGGAMC
21              ------*-*- ---------* ----*----- *--------* ---------** --------*-

250        260        270        280        290        300
                        |          |          |          |          |          |
19 B*1801       CTGCGCGGCT ACTACAACCA GAGCGAGGCC G
20 B*27052      CTGCTCCGCT ACTACAACCA GAGCGAGGCC G
14 19June95  18 CTGCKCSGCT ACTACAACCA GAGCGAGGCC -
16E 09June95 02 CtgcKcSGC
21              ----*-*--- ---------- ---------- *
```

Fig. 30

```
HLA-B(32511)  exon3   9/25/94   2:11 PM
                     10         20         30         40         50         60
                     |          |          |          |          |          |
1 B*1801       GGTCTCACAC CCTCCAGAGG ATGTACGGCT GCGACGTGGG GCCGGACGGG CGCCTCCTCC
2 B*27052      GGTCTCACAC CCTCCAGAAT ATGTATGGCT GCGACGTGGG GCCGGACGGG CGCCTCCTCC
3 19June95 34  ------Acac cctCcaGArk ATGTAyGGCT GCGACGTggG GCCGGACGGG CGCCTCCTCC
4 19June95 02  GGTCTCACAC CCTCCAGARK ATGTAyGGCT GCGACGTGGG GCCGGACGGG CGCCTCCTCC
5              ******---- ---------** -----*---- ---------- ---------- ----------

70         80         90        100        110        120
                     |          |          |          |          |          |
1 B*1801       GCGGGCATGA CCAGTCCGCC TACGACGGCA AGGATTACAT CGCCCTGAAC GAGGACCTGA
2 B*27052      GCGGGTACCA CCAGGACGCC TACGACGGCA AGGATTACAT CGCCCTGAAC GAGGACCTGA
3 19June95 34  GCGGGyAysA CCAGkmCGCC TACGACGGCA AGGATTnCAT CGCnntGAAn GAGGACCTGA
4 19June95 02  GCGGGyAysA CCAGkmCGCC TACGACGGCA AGGATTACAT CGCCCTGAAC GAGGACCTGA
5              -----*-**- ----**---- ---------- ---------- ---------- ----------

130        140        150        160        170        180
                     |          |          |          |          |          |
1 B*1801       GCTCCTGGAC CGCGGCGGAC ACCGCGGCTC AGATCACCCA GCGCAAGTGG GAGGCGGCCC
2 B*27052      GCTCCTGGAC CGCCGCGGAC ACGGCGGCTC AGATCACCCA GCGCAAGTGG GAGGCGGCCC
3 19June95 34  GCTCcTGGAC CGCsGcgGAC ACsGcnnnnC AGATCACCCA GCGCAAGTGG GAGGCGGCCC
4 19June95 02  GCTCCTGGAC CGCsGCGGAC ACsGCGGCTC AGATCACCCA GCGCAAGTGG GAGGCGGCCC
5              ---*------ --*------- ---------- ---------- ---------- ----------

190        200        210        220        230        240
                     |          |          |          |          |          |
1 B*1801       GTGTGGCGGA GCAGCTGAGA GCCTACCTGG AGGGCACGTG CGTGGAGTGG CTCCGCAGAC
2 B*27052      GTGTGGCGGA GCAGCTGAGA GCCTACCTGG AGGGCGAGTG CGTGGAGTGG CTCCGCAGAT
3 19June95 34  GTGTGGCGGA gcAGCTGAGA GCCTACCTGG AGGGCrmGTG CGTGGAGTGG CTCCGCAGAy
4 19June95 02  GTGTGGCGGA GCAGCTGAGA GCCTACCTGG AGGGCRMGTG CGTGGAGTGg cTCCGCAGAy
5              ---------- ---------- ---------- -----**--- ---------- ---------*

250        260        270        280        290        300
                     |          |          |          |          |          |
1 B*1801       ACCTGGAGAA CGGGAAGGAG ACGCTGCAGC GCGCGG
2 B*27052      ACCTGGAGAA CGGGAAGGAG ACGCTGCAGC GCGCGG
3 19June95 34  ACCTGGAGAA CGGGAAGGAG ACGCTGCAGC GCGCGG
4 19June95 02  ACCTGgAGAA CGGGgAGGaG AcgT
5              --------- ----*----- ---*------ ------
```

Fig. 33

```
KT17 exon 2 layout  9/27/95  12:45'
                        -160        -150        -140        -130        -120
                         |           |           |           |           |
1 05·KT17-C5.1                                                                      ==>
6
2E 11·KT17-3.6          TC GGAGCCTGGC CCTGACCGAG ACCTGGGCCG GTGAGTGCGG GGTTGGGA
5 Cw*0303/0401 exon 2                                                               ==>
3 Cw*0303-exon2                                                                     ==>
4 Cw*0401-exon2                                                                     ==>

-110        -100         -90         -80         -70
                         |           |           |           |           |
1 05·KT17-C5.1                                                                      ==>
6
2E 11·KT17-3.6          GG GAAWCGGCCT CTGSGGAGAG GAGCGAGGGG CCCGCCCGGC GAGGGCGC
5 Cw*0303/0401 exon 2                                                               ==>
3 Cw*0303-exon2                                                                     ==>
4 Cw*0401-exon2                                                                     ==>

-60         -50         -40         -30         -20
                          |           |           |           |           |
1 05·KT17-C5.1                                                                      ==>
6
2E 11·KT17-3.6          AG GACCCGGGGA GCCGCGCAGG GAGGAGGGTC GGGCGGGTCT CAGCCACT
5 Cw*0303/0401 exon 2                                                               ==>
3 Cw*0303-exon2                                                                     ==>
4 Cw*0401-exon2                                                                     ==>

-10          0          10          20          30
                          |           |           |           |           |
1 05·KT17-C5.1                   CCCNAG GCTCCCACTC CATGAGGTAT TTCTMCACMK CYGTGTCC
6                                       ---------- ---------- ---------- --------
2E 11·KT17-3.6          CC TCGTCCCCAG GCTCCCACTC CATGAGGTAT TTCTMCACMK CYGTGTCC
5 Cw*0303/0401 exon 2              GCTCCCACTC CATGAGGTAT TTCTmCACmk CyGTGTCC
3 Cw*0303-exon2                    GCTCCCACTC CATGAGGTAT TTCTACACCG CTGTGTCC
4 Cw*0401-exon2                    GCTCCCACTC CATGAGGTAT TTCTCCACAT CCGTGTCC 40          50          60          70          80
                           |           |           |           |           |
1 05·KT17-C5.1          YG GCCCGGCCGC GGGGAGCCCC RCTTCATCGC AGTGGGCTAC GTGGACGA
6                       -- ---------- ---------- ---------- ---------- --------
2E 11·KT17-3.6          YG GCCCGGCCGC GGGGAGCCCC RCTTCATCGC AGTGGGCTAC GTGGACGA
5 Cw*0303/0401 exon 2   yG GCCCGGCCGC GGGGAGCCCC rCTTCATCGC AGTGGGCTAC GTGGACGA
3 Cw*0303-exon2         CG GCCCGGCCGC GGGGAGCCCC ACTTCATCGC AGTGGGCTAC GTGGACGA
4 Cw*0401-exon2         TG GCCCGGCCGC GGGGAGCCCC GCTTCATCGC AGTGGGCTAC GTGGACGA 90         100         110         120         130
                           |           |           |           |           |
1 05·KT17-C5.1          CA CGCAGTTCGT GCGGTTCGAC AGCGACGCCG CGAGTCCRAG AGGGGAGC
6                       -- ---------- ---------- ---------- ---------- --------
2E 11·KT17-3.6          CA CGCAGTTCGT GCGGTTCGAC AGCGACGCCG CGAGTCCRAG AGGGGAGC
5 Cw*0303/0401 exon 2   CA CGCAGTTCGT GCGGTTCGAC AGCGACGCCG CGAGTCCrAG AGGGGAGC
3 Cw*0303-exon2         CA CGCAGTTCGT GCGGTTCGAC AGCGACGCCG CGAGTCCGAG AGGGGAGC
4 Cw*0401-exon2         CA CGCAGTTCGT GCGGTTCGAC AGCGACGCCG CGAGTCCAAG AGGGGAGC 140         150         160         170         180
                           |           |           |           |           |
1 05·KT17-C5.1          CG CGGGMGCCGT GGGTGGAGCA GGAGGGGCCG GAGTATTGGG ACCGGGAG
6                       -- ---------- ---------- ---------- ---------- --------
2E 11·KT17-3.6          CG CGGGMGCCGT GGGTGGAGCA GGAGGGGCCG GAGTATTGGG ACCGGGAG
5 Cw*0303/0401 exon 2   CG CGGGmGCCGT GGGTGGAGCA GGAGGGGCCG GAGTATTGGG ACCGGGAG
3 Cw*0303-exon2         CG CGGGCGCCGT GGGTGGAGCA GGAGGGGCCG GAGTATTGGG ACCGGGAG
4 Cw*0401-exon2         CG CGGGAGCCGT GGGTGGAGCA GGAGGGGCCG GAGTATTGGG ACCGGGAG
```

Fig. 36A

```
KT17 exon 2 layout  9/27/95  12:45
```

|  | 190      200      210      220      230 |
|---|---|
| 1 05•KT17-C5.1<br>6 | AC ACAGAAGTAC AAGCGCCAGG CACAGRCTGA CCGAGTGARC CTGCGGAA<br>-- ---------- ---------- ---------- ---------- -------- |
| 2£ 11•KT17-3.6 | AC ACAGAAGTAC AAGCGCCAGG CACAGRCTGA CCGAGTGARC CTGCGGAA |
| 5 Cw*0303/0401 exon 2 | AC ACAGAAGTAC AAGCGCCAGG CACAGrCTGA CCGAGTGArC CTGCGGAA |
| 3 Cw*0303-exon2 | AC ACAGAAGTAC AAGCGCCAGG CACAGACTGA CCGAGTGAGC CTGCGGAA |
| 4 Cw*0401-exon2 | AC ACAGAAGTAC AAGCGCCAGG CACAGGCTGA CCGAGTGAAC CTGCGGAA |

|  | 240      250      260      270      280 |
|---|---|
| 1 05•KT17-C5.1<br>6 | MC TGCGCGGCTA CTACAACCAG AGCGAGGMCR GTGAGTGACC CCGGCCCG<br>-- ---------- ---------- ---------- |
| 2£ 11•KT17-3.6 | MC TGCGCGG |
| 5 Cw*0303/0401 exon 2 | mC TGCGCGGCTA CTACAACCAG AGCGAGGmCr |
| 3 Cw*0303-exon2 | CC TGCGCGGCTA CTACAACCAG AGCGAGGCCA |
| 4 Cw*0401-exon2 | AC TGCGCGGCTA CTACAACCAG AGCGAGGACG |

|  | 290      300      310      320      330 |
|---|---|
| 1 05•KT17-C5.1<br>6 | GG GCGCAGGTCA CGACCCCTTC CTCCATGCCC CCACGGNACG GGCCCGGG<br><== |
| 2£ 11•KT17-3.6 | <== |
| 5 Cw*0303/0401 exon 2 | <== |
| 3 Cw*0303-exon2 | <== |
| 4 Cw*0401-exon2 | <== |

|  | 340      350      360      370      380 |
|---|---|
| 1 05•KT17-C5.1<br>6 | TT CGCCCCAAGT TCTTCCCGCG TCTGAGATCC ACCCCGAGG<br><== |
| 2£ 11•KT17-3.6 | <== |
| 5 Cw*0303/0401 exon 2 | <== |
| 3 Cw*0303-exon2 | <== |
| 4 Cw*0401-exon2 | <== |

Fig. 36B

```
KT17 exon 3 layout    9/27/95  12:47
                      -110       -100        -90        -80        -70
                      |          |           |          |          |
3E 21·KT17-3.7        AWTCC CCARTYAMCY TTWMCCSGKT TCAATTTCAA KTTWRGSCMA AAWYC
5                                                                     ==>
4 Cw*0303/0401 exon 3                                                 ==>
1 Cw*0303-exon3                                                       ==>
2 Cw*0401-exon3                                                       ==>

-60        -50        -40        -30        -20
                      |          |          |          |          |
3E 21·KT17-3.7        CCSSS GGKTKGTYSG GASYGGGGCG GGGCTCGGGG GACSGGGCTG ACCAC
5                                                                     ==>
4 Cw*0303/0401 exon 3                                                 ==>
1 Cw*0303-exon3                                                       ==>
2 Cw*0401-exon3                                                       ==>

-10        0          10         20         30
                      |          |          |          |          |
3E 21·KT17-3.7        GGGGG CGGGGCCCAG GGTCTCACAY CMTCCAGAGG ATGTWTGGCT GCGAC
5                     ---------------- ---------- ---------- ---------- -----
4 Cw*0303/0401 exon 3                  GGTCTCACAy CmTCCAGAGG ATGTwTGGCT GCGAC
1 Cw*0303-exon3                        GGTCTCACAT CATCCAGAGG ATGTATGGCT GCGAC
2 Cw*0401-exon3                        GGTCTCACAC CCTCCAGAGG ATGTTTGGCT GCGAC 40         50         60         70         80
                      |          |          |          |          |
3E 21·KT17-3.7        STGGG GCCSGACGGG CGCCTCCTCC GCGGGTATRA CCAGTWCGCC TACGA
5                     ----- ---------- ---------- ---------- ---------- -----
4 Cw*0303/0401 exon 3 sTGGG GCCsGACGGG CGCCTCCTCC GCGGGTATrA CCAGTwCGCC TACGA
1 Cw*0303-exon3       GTGGG GCCCGACGGG CGCCTCCTCC GCGGGTATGA CCAGTACGCC TACGA
2 Cw*0401-exon3       CTGGG GCCGGACGGG CGCCTCCTCC GCGGGTATAA CCAGTTCGCC TACGA 90         100        110        120        130
                      |          |          |          |          |
3E 21·KT17-3.7        CGGCA AGGATTACAT CGCCCTGAAC GAGGATCTGC GCTCCTGGAC CGCCG
5                     ----- ---------- ---------- ---------- ---------- ---*-
4 Cw*0303/0401 exon 3 CGGCA AGGATTACAT CGCCCTGAAC GAGGATCTGC GCTCCTGGAC CGCGG
1 Cw*0303-exon3       CGGCA AGGATTACAT CGCCCTGAAC GAGGATCTGC GCTCCTGGAC CGCGG
2 Cw*0401-exon3       CGGCA AGGATTACAT CGCCCTGAAC GAGGATCTGC GCTCCTGGAC CGCGG 140        150        160        170        180
                      |          |          |          |          |
3E 21·KT17-3.7        CGGAC ACGGCGGCTC AGATCACCCA GCGCAAGTGG GAGGCGGCCC GTGAG
5                     ----- ---------- ---------- ---------- ---------- -----
4 Cw*0303/0401 exon 3 CGGAC ACGGCGGCTC AGATCACCCA GCGCAAGTGG GAGGCGGCCC GTGAG
1 Cw*0303-exon3       CGGAC ACGGCGGCTC AGATCACCCA GCGCAAGTGG GAGGCGGCCC GTGAG
2 Cw*0401-exon3       CGGAC ACGGCGGCTC AGATCACCCA GCGCAAGTGG GAGGCGGCCC GTGAG 190        200        210        220        230
                      |          |          |          |          |
3E 21·KT17-3.7        GCGGA GCAGCKGAGA GCCTACCTGG AGGGCMYGTG CGTGGAGTGG CTCCG
5                     ----- ---------- ---------- ---------- ---------- -----
4 Cw*0303/0401 exon 3 GCGGA GCAGCkGAGA GCCTACCTGG AGGGCmyGTG CGTGGAGTGG CTCCG
1 Cw*0303-exon3       GCGGA GCAGCTGAGA GCCTACCTGG AGGGCCTGTG CGTGGAGTGG CTCCG
2 Cw*0401-exon3       GCGGA GCAGCGGAGA GCCTACCTGG AGGGCACGTG CGTGGAGTGG CTCCG 240        250        260        270        280
                      |          |          |          |          |
3E 21·KT17-3.7        CAGAT ACCTGRAGAA YGGGAAG
5                     ----- ---------- -------
4 Cw*0303/0401 exon 3 CAGAT ACCTGrAGAA yGGGAAGGAG ACGCTGCAGC GCGCGG
1 Cw*0303-exon3       CAGAT ACCTGAAGAA TGGGAAGGAG ACGCTGCAGC GCGCGG
2 Cw*0401-exon3       CAGAT ACCTGGAGAA CGGGAAGGAG ACGCTGCAGC GCGCGG
```

Fig. 38

```
                          SEQUENCE LISTING (1) GENERAL INFORMATION:

(iii) NUMBER OF SEQUENCES: 32

(2) INFORMATION FOR SEQ ID NO: 1:

(i) SEQUENCE CHARACTERISTICS:
        (A) LENGTH: 17 nucleotides
        (B) TYPE: nucleic acid
        (C) STRANDEDNESS:  single
        (D) TOPOLOGY:  linear (xi) SEQUENCE DESCRIPTION: SEQ ID NO: 1:

CGCCGAGGAT GGCCGTC                                                      17

(2) INFORMATION FOR SEQ ID NO: 2:

(i) SEQUENCE CHARACTERISTICS:
        (A) LENGTH: 26 nucleotides
        (B) TYPE: nucleic acid
        (C) STRANDEDNESS:  single
        (D) TOPOLOGY:  linear (xi) SEQUENCE DESCRIPTION: SEQ ID NO: 2:

GGAGAACCAG GCCAGCAATG ATGCCC                                            26

(2) INFORMATION FOR SEQ ID NO: 3:

(i) SEQUENCE CHARACTERISTICS:
        (A) LENGTH: 26 nucleotides
        (B) TYPE: nucleic acid
        (C) STRANDEDNESS:  single
        (D) TOPOLOGY:  linear (xi) SEQUENCE DESCRIPTION: SEQ ID NO: 3:

GGAGAACTAG GCCAGCAATG ATGCCC                                            26

(2) INFORMATION FOR SEQ ID NO: 4:

(i) SEQUENCE CHARACTERISTICS:
        (A) LENGTH: 19 nucleotides
        (B) TYPE: nucleic acid
        (C) STRANDEDNESS:  single
        (D) TOPOLOGY:  linear
```

(xi) SEQUENCE DESCRIPTION: SEQ ID NO: 4:

GGCCCTGACC GAGACCTGG                                                                              19

(2) INFORMATION FOR SEQ ID NO: 5:

(i) SEQUENCE CHARACTERISTICS:
        (A) LENGTH: 24 nucleotides
        (B) TYPE: nucleic acid
        (C) STRANDEDNESS:  single
        (D) TOPOLOGY:  linear (xi) SEQUENCE DESCRIPTION: SEQ ID NO: 5:

TCCGATGACC ACAACTGCTA GGAC                                                                        24

(2) INFORMATION FOR SEQ ID NO: 6:

(i) SEQUENCE CHARACTERISTICS:
        (A) LENGTH: 21 nucleotides
        (B) TYPE: nucleic acid
        (C) STRANDEDNESS:  single
        (D) TOPOLOGY:  linear (xi) SEQUENCE DESCRIPTION: SEQ ID NO: 6:

GGCCCTGACCG AGACCTGGGC                                                                            21

(2) INFORMATION FOR SEQ ID NO: 7:

(i) SEQUENCE CHARACTERISTICS:
        (A) LENGTH: 21 nucleotides
        (B) TYPE: nucleic acid
        (C) STRANDEDNESS:  single
        (D) TOPOLOGY:  linear (xi) SEQUENCE DESCRIPTION: SEQ ID NO: 7:

GGCCCTGACC CAGACCTGGG C                                                                           21

(2) INFORMATION FOR SEQ ID NO: 8:

(i) SEQUENCE CHARACTERISTICS:
        (A) LENGTH: 24 nucleotides
        (B) TYPE: nucleic acid
        (C) STRANDEDNESS:  single
        (D) TOPOLOGY:  linear (xi) SEQUENCE DESCRIPTION: SEQ ID NO: 8:

CCACAGCTCCT AGGACAGCTA GGA                                                                        24

(2) INFORMATION FOR SEQ ID NO: 9:

(i) SEQUENCE CHARACTERISTICS:
        (A) LENGTH: 19 nucleotides
        (B) TYPE: nucleic acid
        (C) STRANDEDNESS:  single
        (D) TOPOLOGY:  linear (xi) SEQUENCE DESCRIPTION: SEQ ID NO: 9:

CTCGCCCCCA GGCTCCCAC                                                                              19

(2) INFORMATION FOR SEQ ID NO: 10:

(i) SEQUENCE CHARACTERISTICS:
        (A) LENGTH: 17 nucleotides
        (B) TYPE: nucleic acid
        (C) STRANDEDNESS:  single
        (D) TOPOLOGY:  linear (xi) SEQUENCE DESCRIPTION: SEQ ID NO: 10:

GCGGGGGCGG GTCCAGG                                                    17

(2) INFORMATION FOR SEQ ID NO: 11:

(i) SEQUENCE CHARACTERISTICS:
        (A) LENGTH: 21 nucleotides
        (B) TYPE: nucleic acid
        (C) STRANDEDNESS: single
        (D) TOPOLOGY: linear (xi) SEQUENCE DESCRIPTION: SEQ ID NO: 11:

CTGACTCTTC CCATCAGACC C                                               21

(2) INFORMATION FOR SEQ ID NO: 12:

(i) SEQUENCE CHARACTERISTICS:
        (A) LENGTH: 21 nucleotides
        (B) TYPE: nucleic acid
        (C) STRANDEDNESS: single
        (D) TOPOLOGY: linear (xi) SEQUENCE DESCRIPTION: SEQ ID NO: 12:

CACTCACCGG CCTCGCTCTG G                                               21

(2) INFORMATION FOR SEQ ID NO: 13:

(i) SEQUENCE CHARACTERISTICS:
        (A) LENGTH: 19 nucleotides
        (B) TYPE: nucleic acid
        (C) STRANDEDNESS: single
        (D) TOPOLOGY: linear (xi) SEQUENCE DESCRIPTION: SEQ ID NO: 13:

CCACTGCCCC TGGTACCCG                                                  19

(2) INFORMATION FOR SEQ ID NO:14:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (xi) SEQUENCE DESCRIPTION: SEQ ID NO: 14:

AGGGTGAGGG GCTTCGGCAG CC                                              22

(2) INFORMATION FOR SEQ ID NO:15:

(i) SEQUENCE CHARACTERISTICS:
        (A) LENGTH: 19 nucleotides
        (B) TYPE: nucleic acid
        (C) STRANDEDNESS: single
        (D) TOPOLOGY: linear (xi) SEQUENCE DESCRIPTION: SEQ ID NO: 15:

CTCGCCCCCA GGCTCCCAC                                                  19

(2) INFORMATION FOR SEQ ID NO:16:

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (xi) SEQUENCE DESCRIPTION: SEQ ID NO: 16:

GCGGGGGCGG GTCCAGG                                                      17

(2) INFORMATION FOR SEQ ID NO:17:

(i) SEQUENCE CHARACTERISTICS:
        (A) LENGTH: 21 nucleotides
        (B) TYPE: nucleic acid
        (C) STRANDEDNESS: single
        (D) TOPOLOGY: linear (xi) SEQUENCE DESCRIPTION: SEQ ID NO: 17:

CTGACTCTTC CCATCAGACC C                                                 21

(2) INFORMATION FOR SEQ ID NO:18:

(i) SEQUENCE CHARACTERISTICS:
        (A) LENGTH: 21 nucleotides
        (B) TYPE: nucleic acid
        (C) STRANDEDNESS: single
        (D) TOPOLOGY: linear (xi) SEQUENCE DESCRIPTION: SEQ ID NO: 18:

CACTCACCGG CCTCGCTCTG G                                                 21

(2) INFORMATION FOR SEQ ID NO:19:

(i) SEQUENCE CHARACTERISTICS:
        (A) LENGTH: 19 nucleotides
        (B) TYPE: nucleic acid
        (C) STRANDEDNESS: single
        (D) TOPOLOGY: linear (xi) SEQUENCE DESCRIPTION: SEQ ID NO: 19:

CCACTGCCCC TGGTACCCG                                                    19

(2) INFORMATION FOR SEQ ID NO:20:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (xi) SEQUENCE DESCRIPTION: SEQ ID NO: 20:

AGGGTGAGGG GCTTCGGCAG CC                                                22

(2) INFORMATION FOR SEQ ID NO:21:

(i) SEQUENCE CHARACTERISTICS:
        (A) LENGTH: 18 nucleotides
        (B) TYPE: nucleic acid
        (C) STRANDEDNESS: single
        (D) TOPOLOGY: linear (xi) SEQUENCE DESCRIPTION: SEQ ID NO: 21:

CCTCCTGCTG CTCTCGGC                                                     18

(2) INFORMATION FOR SEQ ID NO:22:

(i) SEQUENCE CHARACTERISTICS:
        (A) LENGTH: 19 nucleotides
        (B) TYPE: nucleic acid
        (C) STRANDEDNESS: single
        (D) TOPOLOGY: linear (xi) SEQUENCE DESCRIPTION: SEQ ID NO: 22:

CCTCCTGCTG CTCTCGGGA                                                    19

(2) INFORMATION FOR SEQ ID NO:23:

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (xi) SEQUENCE DESCRIPTION: SEQ ID NO: 23:

GCTGCTCTGG GGGGCAG                                                17

(2) INFORMATION FOR SEQ ID NO:24:

(i) SEQUENCE CHARACTERISTICS:
        (A) LENGTH: 21 nucleotides
        (B) TYPE: nucleic acid
        (C) STRANDEDNESS: single
        (D) TOPOLOGY: linear (xi) SEQUENCE DESCRIPTION: SEQ ID NO: 24:

GCTCCGATGA CCACAACTGCT                                            21

(2) INFORMATION FOR SEQ ID NO:25:

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (xi) SEQUENCE DESCRIPTION: SEQ ID NO: 25:

TCGGGCAGGT CTCAGCC                                                17

(2) INFORMATION FOR SEQ ID NO:26:

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (xi) SEQUENCE DESCRIPTION: SEQ ID NO: 26:

TCGGGCGGGTCTCAGCC                                                 17

(2) INFORMATION FOR SEQ ID NO:27:

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (xi) SEQUENCE DESCRIPTION: SEQ ID NO: 27:

GGGCTCGGGG GACCGGG                                                17

(2) INFORMATION FOR SEQ ID NO:28:

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (xi) SEQUENCE DESCRIPTION: SEQ ID NO: 28:

GGGCTCGGGG GACTGGG                                                17

(2) INFORMATION FOR SEQ ID NO:29:

(i) SEQUENCE CHARACTERISTICS:
        (A) LENGTH: 15 nucleotides
        (B) TYPE: nucleic acid
        (C) STRANDEDNESS: single
        (D) TOPOLOGY: linear (xi) SEQUENCE DESCRIPTION: SEQ ID NO: 29:

GAGGCGCCCC GTGGC                      15

(2) INFORMATION FOR SEQ ID NO:30:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (xi) SEQUENCE DESCRIPTION: SEQ ID NO: 30:

CATCCTGCTG CTCTCGGGAG                 20

(2) INFORMATION FOR SEQ ID NO:31:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (xi) SEQUENCE DESCRIPTION: SEQ ID NO: 31:

AGGAGGGTCG GGCGGGTCTCAG              22

(2) INFORMATION FOR SEQ ID NO:32:

(i) SEQUENCE CHARACTERISTICS:
        (A) LENGTH: 26 nucleotides
        (B) TYPE: nucleic acid
        (C) STRANDEDNESS: single
        (D) TOPOLOGY: linear (xi) SEQUENCE DESCRIPTION: SEQ ID NO: 32:

GGGCTGACCA CGGGGGCGGG GCCCAG          26

METHODS AND REAGENTS FOR TYPING HLA CLASS I GENES

This application is a C.I.P. of Ser. No. 08/390,251, filed on Feb. 14, 1995, abandoned.

BACKGROUND

The present invention relates to methods and reagents for typing HLA class I genes utilizing locus-specific nucleic acid amplification followed by sequence-specific detection of the amplified product.

The immune system has evolved a special mechanism to detect infections which occur within cells as opposed to infections which occur in extracellular fluid or blood, e.g., Janeway Jr., Scientific American, September, 73–79 (1993). Generally speaking, this mechanism acts in two steps: first, the immune system finds a way to signal to the body that certain cells have been infected, and then, it mobilizes cells specifically designed to recognize these infected cells and to eliminate the infection.

The initial step, signaling that a cell is infected, is accomplished by special molecules that deliver segments of the invading microbe to the outer surface of the infected cell. These molecules bind to peptide fragments of the invading microbe and then transport the peptides to the outside surface of the infected cell.

These transporter molecules are proteins of the major histocompatibility complex of genes, which in humans is referred to as the human leukocyte antigen complex, or HLA. These HLA molecules can be divided into two Classes: (i) class I molecules which are found on almost all types of cells, and (ii) class II molecules which appear only on cells involved in the immune response.

The two different classes of HLA molecules present peptides that arise in different places within cells. Class I molecules bind to peptides that originate from proteins in the cystolic compartment of the cell. After binding, the class I molecules fold around the foreign peptide then carry the peptide to the cell surface. The presentation of the peptide by the class I molecules then signals other cells of the immune system to destroy the host cell. The genes coding for the class I molecules are further subclassified as the HLA-A, HLA-B, and HLA-C genes.

Unlike class I molecules, class II molecules do not require peptide-directed folding to become active. Moreover, rather than signaling the destruction of the host cell, peptides presented by the class II molecules activate the internal defenses of the host cell, or alternatively, guide the synthesis of specific antibody molecules by the immune system.

The genes that encode the HLA molecules are among the most variable genes in humans: each variant coding for molecules which bind to different peptides. These genes are the same in all the cells of a particular individual, but differ from person to person.

HLA typing is performed routinely in connection with many medical indications, e.g., organ transplantation (rejection of organ grafts is believed to be greatly diminished if the HLA alleles of donor and recipient are identical), the study of auto-immune disease, and the determination of susceptibility to infectious disease.

Traditionally, the majority of HLA typing has been performed using serological techniques. However, these techniques have a number of serious drawbacks: (i) the availability of standard antisera is limited, (ii) the accuracy and resolution of the technique is limited by the small number of alleles which can be tested for, (iii) the speed of serological tests is very slow, and, (iv) new alleles can not be detected.

Recently, to solve many of the problems of serologically-based typing methods, molecular techniques have been employed for HLA typing, including restriction fragment length polymorphism analysis (RFLP), sequence specific oligonucleotide probing and/or priming techniques, and DNA sequencing. By looking directly at the genotype of the HLA system rather than the phenotype, the information content and accuracy of the typing procedure can be greatly enhanced. Examples of sequencing-based methods are provided by Santamaria et al., PCT/US92/01675; Holtz et al., DNA-Technology and Its Forensic Application, Berghaus et al. eds., p 79–84 (1991); Petersdorf et al., Tissue Antigens 44: 211–216 (1994); Guttridge et al., Tissue Antigens 44: 43–46 (1994); Santamaria et al., Human Immunology 37: 39–50 (1993); Santamaria et al., PCT/US92/01676; Santamaria et al., Human Immunology 33: 69–81 (1992); and Petersdorf et al., Tissue Antigens, 43: in press (1994). Examples of probing-based methods are provided by Bunce and Welsh, Tissue Antigens 43: 7–17 (1994); Anrien et al., Tissue Antigens 42: 480–487 (1993); Dominguez et al., Immunogenetics, 36: 277–282 (1992); Yoshida et al., Human Immunology 34: 257–266 (1992); Allen et al., Human Immunology 40: 25–32 (1994); Fernandez-Vina et al., Human Immunology 33: 163–173 (1992); and Teodorica and Erlich, EPO 92118396.8.

Important problems encountered in any of the above molecular techniques include the complexity, reliability and specificity of the DNA amplification procedures. These problems have become particularly critical as these molecular typing techniques have become more commonly used in the clinical environment. Because of the similarity among the HLA-A, -B, and -C genes, it has been up until very recently impossible to find amplification methods which allow discrimination between the three class I genes while at the same time are independent of (i) inadvertent amplification of closely related genes, e.g., neighboring pseudogenes, and (ii) independent of the extreme polymorphism found in these genes, e.g., Cereb et al., Tissue Antigens 45: 1–11 (1995). However, the protocol of Cereb relies on intronic primer sites, making it suseptable to promiscuous intronic mutations.

Current techniques have addressed these problems by limiting the generality of the methods, e.g., limiting the analysis to a subset of exons in a given gene, e.g., Petersdorf et al., Tissue Antigens, 44: 93–99 (1994), where the analysis requires multiple amplification primer sets and sequential amplifications to cover only the HLA-C subtype. This approach is not preferred because of the complexity of the protocols, the amount of information about the sample required prior to the analysis, and the number of reagents required.

SUMMARY

The present invention relates to our discovery of methods and reagents for the DNA typing of HLA class I genes utilizing locus-specific nucleic acid amplification followed by sequence-specific detection of the amplified product.

An object of our invention is to provide methods and reagents for the amplification of the HLA-A, HLA-B, and HLA-C genes of the HLA class I gene family wherein the amplification is able to discriminate among the HLA-A, HLA-B, and HLA-C genes and other related class I genes and pseudogenes.

A further object of our invention is to provide methods and reagents for the specific amplification of the HLA-A, HLA-B, and HLA-C genes of the HLA class I gene family which are not subject to variability due to intronic sequence polymorphisms.

An additional object of our invention is to provide methods and reagents for the specific amplification of each of the HLA-A, HLA-B, and HLA-C genes of the HLA class I gene family wherein a single set of amplification primers serve to amplify the informative regions of each of the HLA-A, -B, or -C genes.

Another object of our invention is to provide methods and reagents for the specific DNA sequencing of the HLA-A, HLA-B, and HLA-C genes of the HLA class I gene family wherein specificity is maximized while the number of sequencing primers and method steps is minimized.

Still another object of our invention is to provide various reagent kits useful for the practice of the aforementioned methods.

Another object of our invention is to provide methods and reagents for the specific DNA sequencing of the HLA-A, HLA-B, and HLA-C genes of the HLA class I gene family wherein the sample DNA is genomic DNA.

The foregoing and other objects of the invention are achieved by a method for typing HLA class I genes wherein a sample DNA containing a HLA class I gene is contacted with a first amplification primer, the first primer including sequence complementary to a first exon of a HLA class I gene, and a second amplification primer, the second primer including sequence complementary to a second exon of the HLA class I gene, wherein the first and second primers are complementry to oppisite strands of the sample DNA. Then, a portion of the sample DNA is amplified by PCR using the first and second primers. Finally, the amplicon formed by the PCR is detected using a sequence-specific detection method.

In a preferred embodiment of the present invention, the sequence-specific detection method is DNA sequencing.

In another aspect, the present invention provides amplification primers and sequencing primers adapted for carrying out the above HLA typing method.

In yet another aspect, the present invention provides kits for carrying out the above HLA typing method.

These and other objects, features, and advantages of the present invention will become better understood with reference to the following description, appended claims, and drawings.

BRIEF DESCRIPTION OF THE DRAWINGS

FIG. 5 is the sequence alignment of the sequences of FIGS. 3 and 4.

FIG. 8 is the sequence alignment of the sequences of FIGS. 6 and 7.

FIG. 11 is the sequence alignment of the sequences of FIGS. 9 and 10.

FIG. 13 is the sequence alignment of the sequence of FIG. 12.

FIG. 16 is the sequence alignment of the sequences of FIGS. 14 and 15.

FIG. 19 is the sequence alignment of the sequences of FIGS. 17 and 18.

FIG. 21 is the sequence alignment of the sequences of FIG. 20.

FIG. 24 is the sequence alignment of the sequences of FIGS. 22 and 23.

FIG. 27 is the sequence alignment of the sequences of FIGS. 25 and 26.

FIG. 30 is the sequence alignment of the sequences of FIGS. 28 and 29.

FIG. 33 is the sequence alignment of the sequences of FIGS. 31 and 32.

FIGS. 36A and 36B are the sequence alignment of the sequences of FIGS. 34 and 35.

FIG. 38 is the sequence alignment of the sequence of FIG. 37.

DESCRIPTION OF THE PREFERRED EMBODIMENTS

Figure 1:
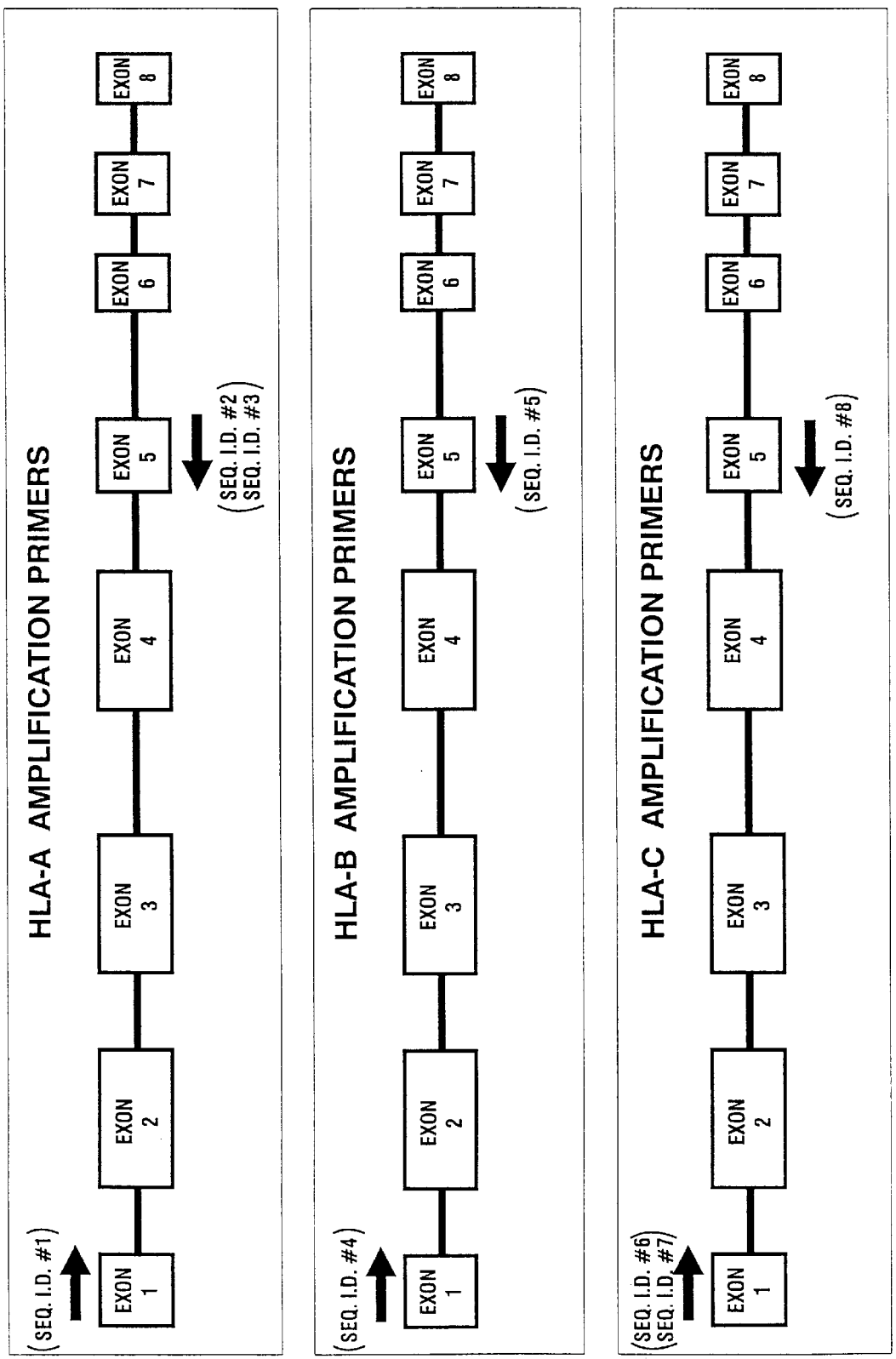
FIG. 1 is a schematic map of the amplification primer locations.
Figure 2:
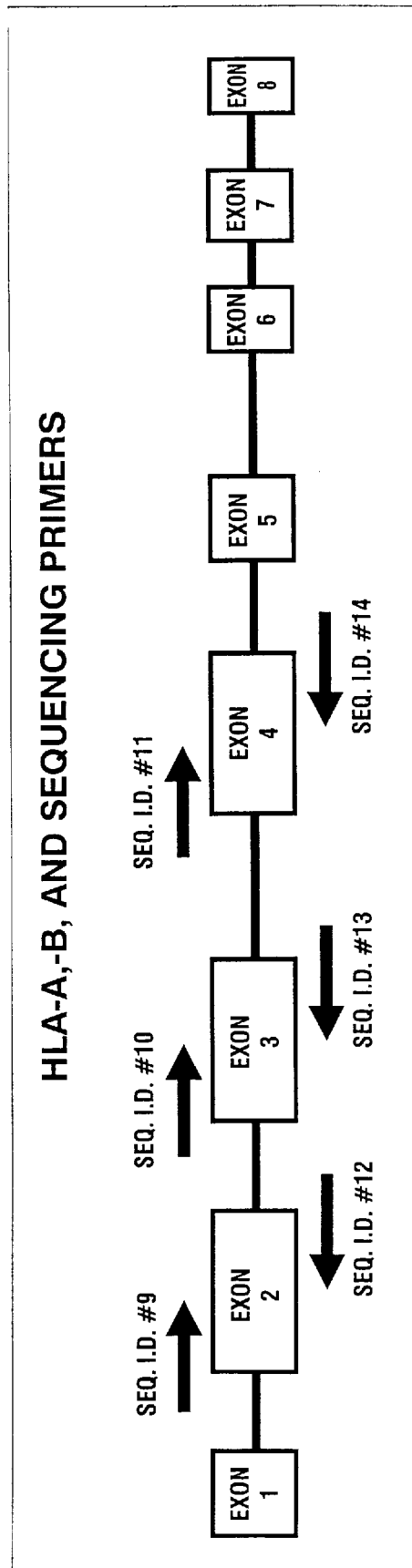
FIG. 2 is a schematic map of the sequencing primer locations.

The present invention is directed to methods and reagents for typing HLA class I genes utilizing locus-specific nucleic acid amplification followed by sequence-specific detection of the amplified product. Generally, the method of the present invention involves amplification of a segment of one or a combination of the HLA-A, HLA-B, and/or HLA-C genes, e.g. by the polymerase chain reaction (PCR), followed by detection of the resulting amplicon(s) by a detection method capable of distinguishing between different-sequence amplicons, e.g., DNA sequencing, sequence specific oligonucleotide probes, restriction digestion, and the like. The reagents of the instant invention include preferred PCR primers and preferred sequencing primers.

1. Definitions

As used herein, the term "gene" refers to a segment of DNA composed of a transcribed region and a regulatory sequence that makes possible a transcription, including both the sense and antisense strands of the DNA. The terms "locus" or "gene locus" refers to the specific place on a chromosome where a gene is located. The term "allele" refers to the multiple forms of a gene that can exist at a single gene locus.

As used herein, the terms "HLA class I genes" or "HLA class I gene family" refer to a subgroup of the genes of the human leukocyte antigen complex located on the short arm of chromosome 6 in the distal portion of the 6p21.3 chromosome, the other members of the human leukocyte antigen complex being the class II and class III genes, e.g., Trowsdale et al., Immunology Today, 12(12): 443–446 (1991).

As used herein, the term "exon" refers to a polynucleotide segment that codes for amino acids, while those segments that are not translated into amino acids are referred to herein as "introns". The term "intron-exon border" refers the interface of the intron segment and the exon segment. When referring to the two strands making up a double stranded DNA molecule, as used herein, the term "antisense strand" or "minus strand" refers to the strand of the pair which serves as the template for transcription of DNA into mRNA, while the term "sense strand" or "plus strand" refers to the other strand of the pair which carries the codons for translation in its sequence.

The term "oligonucleotide" or "polynucleotide" as used herein refer to a molecule having two or more deoxyribonucleotides or ribonucleotides, the number of nucleotides in the molecule depending on its intended function. As used herein the term "primer" refers to an oligonucleotide, preferably produced synthetically, which, when hybridized to a complementary template strand of DNA, is capable of acting as a point of initiation for synthesis of a primer extension product. The terms "first amplification primer" and "second amplification primer" refer to members of a pair of PCR primers which are used to initiate amplification of a "target sequence" of the sample DNA. The first primer and second primer are complementary to opposite strands of the target DNA, i.e., antisense and sense strands, and are located at the opposite ends of the target sequence. A "set" of first primers or second primers refer to a collection of two or more degenerate primers complementary to multiple alleles located at the same gene locus, where, as used herein, the term "degenerate primers" refers to a collection of primers differing in sequence by base substitutions at one or more particular sequence locations.

2. Oligonucleotide Primers

The oligonucleotide primers, both sequencing primers and amplification primers, can be synthesized using any suitable method, e.g., phosphoramidite, phosphotriester, phosphite-triester or phosphodiester synthesis methods, e.g., Gait, Oligonucleotide Synthesis, IRL Press, Washington, D.C. (1984). Preferably, the oligonucleotides of the present invention are prepared using an automated DNA synthesizer, e.g., Applied Biosystems Model 392 DNA Synthesizer (Applied Biosystems Division of the Perkin-Elmer Corporation (ABI), Foster City, Calif.). In a less preferred method, primers can be isolated from a biological source using appropriate restriction endonucleases.

3. Preparation of Sample DNA

Any source of human nucleic acid can be used to obtain the sample nucleic acid as long as the source contains the nucleic acid sequence of interest. Typical samples include peripheral blood mononuclear cells (PBMNCs), lymphoblastoid cell lines (LCLs), hair cells, or the like. Preferably genomic DNA extracted from PBMNCs or LCLs is used.

A large number of methods are available for the isolation and purification of sample DNA for use in the present invention. The preferred purification method should provide sample DNA (i) sufficiently free of protein to allow efficient nucleic acid amplification and sequencing and (ii) of a size sufficient to allow trans-intronic amplification of the class I genes. Preferred purification methods include (i) organic extraction followed by ethanol precipitation, e.g., using a phenol/chloroform organic reagent, e.g., Ausubel et al. eds., Current Protocols in Molecular Biology Volume 1, Chapter 2, Section I, John Wiley & Sons, New York, N.Y. (1993), preferably using an automated DNA extractor, e.g., the Model 341 DNA Extractor available from ABI; (ii) solid phase adsorption methods, e.g., Walsh et al., Biotechniques 10(4): 506–513 (1991); and (iii) salt-induced DNA precipitation methods, e.g., Miller et al., Nucleic Acids Research 16(3): 9–10 (1988), such methods being typically referred to as 'salting-out' methods. More preferably, the sample DNA is purified by salt-induced DNA precipitation methods. Preferably, each of the above purification methods is preceded by an enzyme digestion step to help eliminate protein from the sample, e.g., digestion with proteinase K, or like proteases.

4. PCR Amplification

Amplification of sample DNA for each gene locus of interest is accomplished using the polymerase chain reaction (PCR) as generally described in U.S. Pat. Nos. 4,683,195 and 4,683,202 to Mullis. Generally, the PCR consists of an initial denaturation step which separates the strands of a double stranded nucleic acid sample, followed by the repetition of (i) an annealing step, which allows amplification primers to anneal specifically to a portion of a target sequence of the separated strands of the sample DNA molecule or copies thereof; (ii) an extension step which extends the primers in a 5' to 3' direction thereby forming an amplicon nucleic acid complementary to the target sequence, and (iii) a denaturation step which causes the separation of the amplicon and the target sequence. Each of the above steps may be conducted at a different temperature, where the temperature changes may be accomplished using a thermocycler (Perkin-Elmer Corporation, Norwalk, Conn. (PE)).

The present invention introduces the use of locus-specific amplification primers including sequence which is complementary to conserved exon sequences, where, in a preferred embodiment, the conserved exon sequences are not involved in antigenic determination, but differ in sequence between related genes, e.g., between HLA-A, -B, and -C genes, and related pseudogenes. In contrast to existing HLA typing methods which include primers complementary to purely intronic sequence, the primers of the present invention provide a number of critically important practical advantages.

One important advantage of the present invention is that it makes possible the amplification of the entire informative region of a class I gene in a single PCR product amplicon. As used herein, the term "informative region" refers to a region of a class I gene which is polymorphic between different individuals and codes for portions of the class I proteins which are involved with antigenic determination. By enabling the amplification of the entire informative region in one amplicon, the method of the present invention requires fewer amplification primers, preferably only one pair per gene, leading to the use of fewer reaction tubes and fewer steps in the amplification protocol.

A second significant advantage of the amplification aspect of HLA typing method of the present invention is that the preferred amplification primers can distinguish between the class I genes, i.e., HLA-A, HLA-B, and HLA-C genes, and all closely related genes and pseudogenes, where, as used herein, the term "pseudogene" refers to neighboring sequence regions which are highly homologous to a particular expressed gene but does not give rise to detectable levels of mRNA. This ability to distinguish between related genes is a particularly import feature of the present invention given the extreme level of polymorphism between genes of different individuals and the similar structure of the HLA class I genes.

By building the gene-level specificity of the typing procedure into the amplification step, the post-amplification detection steps do not require gene-level specificity. Again, this significantly reduces the complexity of the overall typing method. For example, when DNA sequencing is used as the detection step (see below), one set of sequencing primers can be used for sequencing all the class I genes, resulting in many fewer sequencing primers and fewer sequencing reactions.

A further considerable advantage of the amplification step of the present invention is that the quality of the amplification is not subject to intronic polymorphisms. This provides for a much more reproducible and robust technique which is immune to the extreme variability of these regions.

Yet another advantage of the amplification step of the present invention is that the sample DNA that is used as the amplification template is genomic DNA rather than mRNA. This makes the amplification process independent of the varying amounts of mRNA present in sample donors depending on their medical condition, e.g., their degree of immuno suppression, greatly enhancing the reliability of the present typing method. Furthermore, because of the poor chemical stability of mRNA, using genomic target DNA reduces the demand placed on the preparation and storage of the sample material.

In a preferred embodiment, the amplification primers are between five nucleotides and 50 nucleotides in length; more preferably between 10 nucleotides and 30 nucleotides in length. This size range provides primers long enough to have a statistically unique sequence, thereby resulting in high stringency hybridization, and short enough to allow easy synthesis and favorable hybridization kinetics.

For the analysis of the HLA-A class I genes, the preferred amplification primers are chosen such that the first amplification primer is complementary to sequence located in exon 1 of the HLA-A gene, and the second amplification primer is complementary to sequence located in exon 5 of the HLA-A gene. Preferably, the first amplification primer comprises a set of degenerate primers having between one and three degenerate sequence locations. More preferably, the first amplification primer includes the sequence CGC-CGAGGATGGCCGTC (SEQ ID #1) and the second amplification primer comprises a set of two degenerate primers, the first degenerate primer of the set including the sequence GGAGAACCAGGCCAGCAATGATGCCC (SEQ ID #2), and the second degenerate primer of the set including the sequence GGAGAACTAGGCCAGCAATGATGCCC (SEQ ID #3), where the underlined nucleotides indicates the location of the C→T degeneracy (note that all sequences reported herein are written in a 5' to 3' orientation). In a more preferred embodiment, the first degenerate primer (SEQ ID #2) and the second degenerate primer (SEQ ID #3) are present in a 1:1 molar ratio.

For the analysis of the HLA-B class I genes, the preferred amplification primers are chosen such that the first amplification primer is complementary to sequence located in exon 1 of the LILA-B gene, and the second amplification primer is complementary to sequence located in exon 5 of the HLA-B gene. Preferably, the first amplification primer includes the sequence GGCCCTGACCGAGACCTGG (SEQ ID #4) and the second amplification primer includes the sequence TCCGATGACCACAACTGCTAGGAC (SEQ ID #5). More preferably, the first amplification primer includes the sequences CCTCCTGCTGCTCTCGGC (SEQ ID #21), CCTCCTGCTGCTCTCGGGA (SEQ ID #22), and GCTGCTCTGGGGGGCAG (SEQ ID #23), and the second amplification primer includes the sequence GCTCCGAT-GACCACAACTGCT (SEQ ID #24).

For the analysis of the HLA-C class I genes, the preferred amplification primers are chosen such that the first amplification primer is complementary to sequence located in exon 1 of the HLA-C gene, and the second amplification primer is complementary to sequence located in exon 5 of the HLA-C gene. Preferably, the first amplification primer comprises a set of degenerate primers having between one and three degenerate sequence locations. More preferably, the first amplification primer comprises a set of two degenerate primers, the first degenerate primer of the set including the sequence GGCCCTGACCGAGACCTGGGC (SEQ ID #6), and the second degenerate primer of the set including the sequence GGCCCTGACCCAGACCTGGGC (SEQ ID #7), where the underlined nucleotides indicates the location of the G→C degeneracy. More preferably, the first amplification primer includes the sequence CATCCTGCT-GCTCTCGGGAG (SEQ ID#30). Preferably, the second amplification primer includes the sequence CCACAGCTC-CTAGGACAGCTAGGA (SEQ ID #8).

Preferably, the PCR method of the present invention is performed using the "hot start" process, e.g., Chou et al., Nucleic Acids Research 20: 1717–23 (1992). In the hot start process, a solid wax layer is formed over a subset of the PCR reactants. The remaining reactants are then added above the wax. In the first thermal cycle, rapid heating to the denaturation temperature melts the wax, whereupon thermal convection suffices to mix the upper and lower layers while the melted wax serves as a vapor barrier for the remainder of the amplification. The performance improvements realized by the hot start process follow from the reduction of primer oligomerization and mis-priming side reactions that can occur during the initial stages of the PCR. Wax particles especially adapted for use with the hot start process are commercially available, e.g., from the Perkin-Elmer Corporation (PE p/n N808-0100).

5. Sequence-Specific Detection

Once the desired HLA class I target sequence has been amplified, the resulting amplicon is then subjected to a sequence specific detection step. The sequence-specific detection methods for use with the present invention may include any method which is capable of distinguishing nucleic acid sequences differing by one or more nucleotides. Such methods include sequence-specific oligonucleotide probe hybridization (SSOP), restriction digestion with allele-specific restriction enzymes, DNA sequencing, and the like. The preferred sequence-specific detection method is DNA sequencing; the more preferred method being the Sanger-type dideoxy-mediated chain termination DNA sequencing method.

Two preferred labeling methods can be practiced with the present invention: (i) primer labeling methods, where the label is attached to the sequencing primer, e.g., Connell et al., Biotechniques 5(4): 342–348 (1987), or (ii) dideoxy terminator methods, where a label is attached to each of the dideoxy-A, -G, -C, or -T dideoxy terminators, e.g., Lee et al., Nucleic Acids Research 20(10): 2471–2483 (1992) and Prober et al., Science 238: 336–341 (1987). Suitable labels include any label which can be attached to a nucleotide, dideoxynucleotide, or polynucleotide in a chemically stable manner. Such labels include, fluorescent labels, chemiluminescent labels, spin labels, radioactive labels, and the like. The more preferred labeling method uses fluorescent labels which are attached to the sequencing primer.

Preferably, the sequencing method of the present invention sequences three exons of each the class I genes. For each of the HLA-A, -B, and -C genes, it is preferred that the exons to be sequenced include exon 2, exon 3, and exon 4. More preferably, each of the two DNA strands of each exon are sequenced, i.e., both the sense and antisense strands of the exon. By sequencing the exons in both directions, the effect of sequencing errors on the assignment of HLA type is minimized.

An important aspect of the present invention is that a single set of sequencing primers can be used to sequence the preferred exons 2, 3, and 4 of each of the HLA-A, -B, and -C class I genes, thereby greatly reducing the number of reagents and the complexity of the sequencing protocols required.

In a preferred embodiment, the sequencing primers are designed such that each primer is complementary to sequence located at an intron-exon boundary, thereby ensuring that the entire polymorphic portion of the exon of interest can be sequenced using a single sequencing primer. More preferably, the sequencing primers are between 10 nucleotides and 30 nucleotides in length.

Preferably, for obtaining the sequence of the antisense strand of exon 2, the sequencing primer is complementary to a region from −20 nucleotides to +20 nucleotides of the 5' intron-exon border of the sense strand of exon 2 (note in the above nomenclature, the "+" indicates a 5' to 3' direction along the polynucleotide strand and the "−" indicates a 3' to 5' direction along the polynucleotide strand). More preferably, the sequencing primer includes the sequence CACTCACCGGCCTCGCTCTGG (SEQ ID#12).

For obtaining the sequence of the sense strand of exon 2, the preferred sequencing primer is complementary to a region from +30 nucleotides to −20 nucleotides of the 5' intron-exon border of the antisense strand of exon 2. More preferably, the sequencing primer includes the sequences CTCGCCCCCAGGCTCCCAC (SEQ ID #9), AGGAGGGTCGGGCGGGTCTCAG (SEQ ID #31), or the degenerate sequences TCGGGCAGGTCTCAGCC (SEQ ID #25) and TCGGGCGGGTCTCAGCC (SEQ ID#26).

Preferably, for obtaining the sequence of the antisense strand of exon 3, the sequencing primer is complementary to a region from −30 nucleotides to +20 nucleotides of the 5' intron-exon border of the sense strand of exon 3. More preferably, the sequencing primer includes the sequences CCACTGCCCCTGGTACCCG (SEQ ID #13) or GAG-GCGCCCCGTGGC (SEQ ID #29)

For obtaining the sequence of the sense strand of exon 3, the preferred sequencing primer is complementary to a region from +20 nucleotides to −20 nucleotides of the 5' intron-exon border of the antisense strand of exon 3. More preferably, the sequencing primer includes the sequences GCGGGGGCGGGTCCAGG (SEQ ID #10), GGGCTGAC-CACGGGGGCGGGGCCCAG (SEQ ID #32), or the degenerate sequences GGGCTCGGGGGACCGGG (SEQ ID#27) and GGGCTCGGGGGACTGGG (SEQ ID #28).

For obtaining the sequence of the antisense strand of exon 4, the preferred sequencing primer is complementary to a region from −30 nucleotides to +20 nucleotides of the 5' intron-exon border of the sense strand of exon 4. Preferably, the sequencing primer includes the sequence AGGGT-GAGGGGCTTCGGCAGCC (SEQ ID#14).

For obtaining the sequence of the antisense strand of exon 4, the preferred sequencing primer is complementary to a region from +40 nucleotides to −10 nucleotides of the 5' intron-exon border of the antisense strand of exon 4. Preferably, the sequencing primer includes the sequence CTGACTCTTCCCATCAGACCC (SEQ ID#11).

The polymerase enzyme for use in the present invention can be any one of a number of possible known polymerase enzymes. Preferably, the polymerase is a thermostable polymerase, such as Taq DNA polymerase, a 94 kDa thermostable, recombinant DNA polymerase obtained by expression of a modified form of the Taq DNA polymerase gene in E. coli, e.g., Gelfand and White, PCR Protocols: A Guide to Methods and Applications, ed., Innis et al., Academic Press, CA, p129–141 (1991). The Taq DNA polymerase is preferred for PCR applications because of its optimal catalytic activity is in the same temperature range at which stringent annealing of primers to template DNA occurs, i.e., 55° C. to 75° C. The Taq enzyme is commercially available from the Perkin-Elmer Corporation under the AmpliTaq™ trademark (PE p/n N801-0060).

A more preferred DNA polymerase for use in the instant invention is the TaqCS DNA polymerase. The TaqCS DNA polymerase is a single-point mutant of the Taq enzyme in which glycine number 46 has been replaced by an aspartic acid residue, i.e., a G46D mutant. Because the TaqCS enzyme coupled with cycle sequencing methods uses five to ten times less sequencing template as is required when using wildtype Taq enzyme, the use of the TaqCS enzyme obviates the need for any post-PCR purification prior to performing the sequencing reaction, resulting in a much simplified typing protocol. The TaqCS enzyme is available from the Perkin-Elmer Corporation under the AmpliTaqCS™ trademark. Another preferred varient of the AmpliTaq™ enzyme is the AmpliTaq™ DNA polymerase, FS, also available from Perkin-Elmer (p/n 402114)

6. Typing

Once the relevant DNA sequence information has been obtained, the sample is typed by comparing the experimentally determined DNA sequence (multiple sequences in the case of heterozygote samples) with well characterized sequences having known HLA types. Preferably the sequence comparison is performed using a computerized database.

7. Kits for Practicing the Preferred Embodiments of the Invention

The present invention lends itself readily to the preparation of kits containing the elements necessary to carry out the methods of the instant invention. As used herein, the term "kit" refers generally to a collection of containers containing the necessary elements to carry out the process of the invention in an arrangement both convenient to the user and which maximizes the chemical stability of the elements. Such a kit may comprise a carrier being compartmentalized to receive in close confinement therein one or more containers, such as tubes or vials, as well as printed instructions including a description of the most preferred protocols for carrying out the methods of the invention in a particular application, e.g., typing HLA-A, -B, and/or -C class I genes.

A first set of containers may contain the reagents for amplification of the desired target sequences. One container may contain an "upper" PCR amplification reagent, the reagent preferably including an aqueous solution of A, G, C, and T deoxynucleotides, and a polymerase enzyme, preferably a thermostable polymerase, e.g., TAQ polymerase. A second container may contain a "lower" PCR amplification reagent comprising an aqueous solution containing application-specific amplification primers, buffer, and other salts, e.g., magnesium. A third container may contain wax beads for use as a temporary liquid barrier between the upper and lower amplification reagents, e.g., the hot start process. Generally, the contents of the above kit components may be used as follows: (i) an aliquot of the lower amplification buffer may be added to a reaction container and a wax bead may be placed on top of the buffer; (ii) the contents of the reaction tube may then be heated to melt the wax, thereby forming a liquid barrier; (iii) the upper amplification buffer and the sample may then be added to the reaction container on top of the wax barrier; and finally, (iv) the above mixture may be subjected to thermal cycling, e.g., using a thermal cycler instrument.

A second set of containers may be included in the kits of the present invention, the second set comprising containers holding reagents for DNA sequencing. This set of containers may include four containers for each sequencing direction, i.e., 5' to 3' or 3' to 5' directions, of each locus to be sequenced, each container including application-specific sequencing primers, deoxy-and dideoxynucleotides, buffer, and other salts.

Clearly, other arrangements of containers and reagents may be used in the kits of the present invention. For example, some of the reagents of the kits may be supplied in a lyophilized state to enhance storage stability; the kits may include controls for calibration purposes; and, the kits may also include instructions describing preferred protocols for using the kits.

8. Examples

The invention will be further clarified by a consideration of the following examples, which are intended to be purely exemplary of the invention.

EXAMPLE 1

PCR Amplification of HLA-A, HLA-B, and HLA-C Class I Genes

PCR amplification was performed using a Perkin-Elmer 9600 thermal cycler. The amplification was performed with a wax-barrier hot start using Ampliwax™ wax pellets (PE p/n N808-0100). The amplification was performed on human genomic DNA that was purified from (i) peripheral blood cells, i.e., in the HLA-A and HLA-B examples, or (ii) from cultured cell lines, i.e., HLA-C where the BM21 cell line was used as the sample DNA source. The purification method used for all samples was the salting-out method, e.g., Miller et al., Nucleic Acids Research 16(3): 9–10 (1988). The average length of the purified genomic DNA was estimated to be at least 5 kilobases.

The amplification primers used for amplifying each of the HLA-A, -B, and -C genes are shown in Table I below.

TABLE I

Amplification Primers

| SEQ ID | Gene | Exon | Strand[c] | Sequence[a,b] |
|---|---|---|---|---|
| SEQ ID #1 | HLA-A | 1 | Antisense | CGCCGAGGATGGCCGT[G] |
| SEQ ID #2 | HLA-A | 5 | Sense | GGAGAAC$\underline{C}$AGGCCAGCAATGATGCCC |
| SEQ ID #3 | HLA-A | 5 | Sense | GGAGAAC$\underline{T}$AGGCCAGCAATGATGCCC |
| SEQ ID #4 | HLA-B | 1 | Antisense | GGCCCTGACCGAGACCTGG |
| SEQ ID #5 | HLA-B | 5 | Sense | TCCGATGACCACAACTGCTAGGAC |
| SEQ ID #6 | HLA-C | 1 | Antisense | GGCCCTGACC$\underline{G}$AGACCTGGGC |
| SEQ ID #7 | HLA-C | 1 | Antisense | GGCCCTGACC$\underline{C}$AGACCTGGGC |
| SEQ ID #8 | HLA-C | 5 | Sense | CCACAGCTCCTAGGACAGCTAGGA | a. Underlined nucleotides indicate a degenerate position.
b. Sequences SEQ ID #2 and SEQ ID #3, and sequences SEQ ID #6 and SEQ ID #7 are both degenerate primer pairs that were used as a 1:1 molar mixture.
c. The Strand refers to the strand of the target DNA duplex to which the amplification primer binds.

The PCR reaction for each of the HLA-A, -B, and -C genes was prepared as follows. First, a 5× concentrated PCR buffer was prepared having a final composition of 300 mM Tris[hydroxymethyl]aminomethane-HCl (Tris-HCl), 75 mM $(NH_4)_2SO_4$, and 7.5 mM $MgCl_2$, and having a pH of 9.0, such buffer being commercially available from Invitrogen Corporation, San Diego, Calif. (p/n Ki220-02-E). Next, 10 µl of the concentrated PCR buffer was mixed with 5 µl of a 10 mM deoxynucleotide triphosphate (dNTP) solution (2.5 mM each of dATP, dCTP, dGTP, and dTTP), 1 µl of a 10 pMole/µl solution of the sense-strand amplification primer(s), 1 µl of a 10 pMole/µl solution of the antisense-strand amplification primer(s), 2.5 µl of a 100 ng/µl solution of the purified human genomic DNA, and, 20.5 µl of sterile double-distilled (dd) H$_2$O, resulting in a final volume of 40 µl.

Next, each of the above-prepared 40 µl reaction mixtures was added to a Microamp reaction tube (PE p/n N801-0533, N801-0534, N801-0540) containing one Ampliwax™ pellet (PE p/n N808-0100). The tube was then capped, briefly spun in a centrifuge at 3000 rpm to remove all droplets from the side of the tube, then heated to 65° C. for 5 minutes to melt the Ampliwax™ pellet. The tube was then cooled to 4° C., thus forming a wax liquid barrier. A dilution of the Ampli-Taq™ DNA polymerase enzyme (PE p/n N801-0060) was then made to a final concentrations of 0.1 U/µl in sterile ddH$_2$O. This enzyme solution was then layered on top of the wax liquid barrier.

The reaction tubes were then placed in a Perkin-Elmer 9600 thermal cycler, denatured at 98° C. for 20 s, then the following thermal cycle was run: 98° C. for 5 s followed by 68° C. for 2 min, where the cycle was repeated eight times; and 96° C. for 5 s followed by 70° C. for 2 min, where the cycle was repeated 32 times.

Following thermocycling, 8 µl of each of the reactions was analyzed by agarose gel electrophoresis to ensure proper PCR amplification. A 0.7% agarose gel was used containing ethidium bromide at 0.8 µg/ml and TBE buffer (89 mM Tris-HCl, 89 mM Boric Acid, 2 mM Na$_2$EDTA, pH8.3) as both the gel and running buffer. The gel was electrophoresed at 7 V/cm for 2 hrs and visualized using a UV transilluminator. A band at about 2.0 kb for the HLA-A, and -B, or C products was seen indicating successful amplification of each of the specific genes (sizes based on internal size standards).

EXAMPLE 2

DNA Sequencing of Exons 2, 3, and 4 of the HLA-A, HLA-B, and HLA-C Class I Genes Using the Amplification Products from Example 1

Sequencing was performed with no purification of the PCR products using the TaqCS polymerase enzyme.

The sequencing primers shown below in Table II were used to sequence exons 2, 3 and 4 of HLA-A, B and C genes.

TABLE II

DNA Sequencing Primers

| SEQ ID | Exon | Strand[a] | Sequence[b] |
|---|---|---|---|
| SEQ ID #9 | 2 | Antisense | CTCGCCCCCAGGCTCCCAC |
| SEQ ID #10 | 3 | Antisense | GCGGGGCGGGTCCAGG |
| SEQ ID #11 | 4 | Antisense | CTGACTCTTCCCATCAGACCC |
| SEQ ID #12 | 2 | Sense | CACTCACCGGCCTCGCTCTGG |
| SEQ ID #13 | 3 | Sense | CCACTGCCCCTGGTACCCG |
| SEQ ID #14 | 4 | Sense | AGGGTGAGGGCTTCGGCAGCC | a. The Strand refers to the strand of the DNA duplex to which the sequencing primer binds.
b. Note that the primer sequences include a CAGGA leader sequence at the 5'-end that was added reduce the effect of interaction of the dye label with the primer. The CGGA leader sequence was not used for controlling hybridization specificity.

Each of the above primers is labeled at the 5'-end with one of the four fluorescent dyes 5-carboxy-fluorescein (FAM), 2',7'-dimethoxy-4', 5'-dichloro-6-carboxy-fluorescene (JOE), N,N,N',N'-tetramethyl-6-carboxyrhodamine (TAMRA), and 6-carboxy-X-rhodamine (ROX), e.g., U.S. Pat. No. 4,855,225.

The sequencing reaction mixes were prepared as shown in Tables III and IV, each reaction being prepared in a Microamp tube (PE p/n N801-0533, N801-0534, N801-0540) while placed in crushed ice. Note that four reaction mixes were prepared for each sequencing primer providing one reaction mix for each A, G, C, or T termination reaction.

TABLE III

Sequencing reaction Mixes for Sequencing Primers
SEQ ID #12, SEQ ID #13, SEQ ID #14, and SEQ ID #15

| | A | C | G | T |
|---|---|---|---|---|
| 5X Seq. Buffer[a] | 1 µl | 1 µl | 2 µl | 2 µl |
| A d/dd[b] | 1 µl | — | — | — |
| C d/dd[c] | — | 1 µl | — | — |
| G d/dd[d] | — | — | 2 µl | — |
| T d/dd[e] | — | — | — | 2 µl |
| A Dye Primer[f] | 1 µl | — | — | — |
| C Dye Primer[f] | — | 1 µl | — | — |
| G Dye Primer[f] | — | — | 2 µl | — |
| T Dye Primer[f] | — | — | — | 2 µl |
| Taq dilution[g] | 1 µl | 1 µl | 2 µl | 2 µl |
| Diluted Template[h] | 1 µl | 1 µl | 2 µl | 2 µl |

[a]The composition of the 5X Seq. Buffer was 400 mM Tris-HCl, 10 mM MgCl$_2$, pH 9.0.
[b]The composition of the A d/dd mix was 900 µM ddATP, 93.75 µM dATP, 250 µM dCTP, 375 µM7-deaza-dGTP, and 250 µM dTTP.
[c]The composition of the C d/dd mix was 450 µM ddCTP, 250 µM dATP, 93.75 µM dCTP, 375 µM7-deaza-dGTP, and 250 µM dTTP.
[d]The composition of the G d/dd mix was 90 µM ddGTP, 250 µM dATP, 250 µM dCTP, 180 µM7-deaza-dGTP, and 250 µM dTTP.
[e]The composition of the T d/dd mix was 1250 µM ddGTP, 250 µM dATP, 250 µM dCTP, 180 µM7-deaza-dGTP, and 250 µM dTTP.
[f]Each primer solution was made at a concentration of 0.4 pmoles/µl.
[g]The TaqCS polymerase was diluted by mixing 1 µl of a TaqCS stock solution with 5 µl of the 5X concentrated sequencing buffer from (a). The TaqCS stock was at a concentration of 5 Units/µl where one unit is defined as in Lawyer et al., J. Biol. Chem. 264:6427–6437 (1989) herein incorporated by reference.
[h]The template was diluted by mixing 1 µl of the PCR product from Example 1 with 5 µl water.

TABLE IV

Sequencing Reaction Mixes for Sequencing Primers
SEQ ID #9 and SEQ ID #10

| | A | C | G | T |
|---|---|---|---|---|
| 5X Seq. Buffer[a] | 1 µl | 1 µl | 2 µl | 2 µl |
| A d/dd[b] | 1 µl | — | — | — |
| C d/dd[c] | — | 1 µl | — | — |
| G d/dd[d] | — | — | 2 µl | — |
| T d/dd[e] | — | — | — | 2 µl |
| A Dye Primer[f] | 2 µl | — | — | — |
| C Dye Primer[f] | — | 2 µl | — | — |
| G Dye Primer[f] | — | — | 4 µl | — |
| T Dye Primer[f] | — | — | — | 4 µl |
| Taq dilution[g] | 1 µl | 1 µl | 2 µl | 2 µl |
| Diluted Template[h] | 1 µl | 1 µl | 2 µl | 2 µl |

[a]–[f]These notes have the same meaning as those in Table III above.

Each of the sequencing reaction mixes were denatured at 98° C. for 5 s then thermocycled in a Perkin-Elmer 9600 thermocycler using the following program: 96° C. for 5 s followed by 55° C. for 40 s, followed by 68° C. for 1 min, where the cycle was repeated 15 times; and 96° C. for 5 s followed by 68° C. for 1 min, where the cycle was repeated 15 times.

After completion of the sequencing reactions, each of the A, G, C, and T reactions for each gene were pooled and added to 200 µl of 95% Ethanol on ice. After allowing the DNA to precipitate, the tubes were centrifuged at 17,000 rpm for 20 min, whereupon the ethanol was decanted by vacuum aspiration. Next, 200 μl of 70% ethanol was added to the dry DNA pellet, vortexed vigorously, then centrifuged at 17,000 rpm for 15 min, then dried in a vacuum centrifuge set to medium heat for 5 minutes. The precipitated samples were then resuspended and loaded on a standard DNA sequencing gel, and run on an automated fluorescent DNA sequencer as described in the Applied Biosystems 373A manual (373A DNA Sequencing System Users Manual, Sections 2, 3, and 4, p/n 901156, Software version 1.10, Document Rev. C, January 1992, ABI).

The following FIGS. 3–21 show examples of HLA class I typing data collected using the protocols of Examples 1 and 2.

Figure 3:
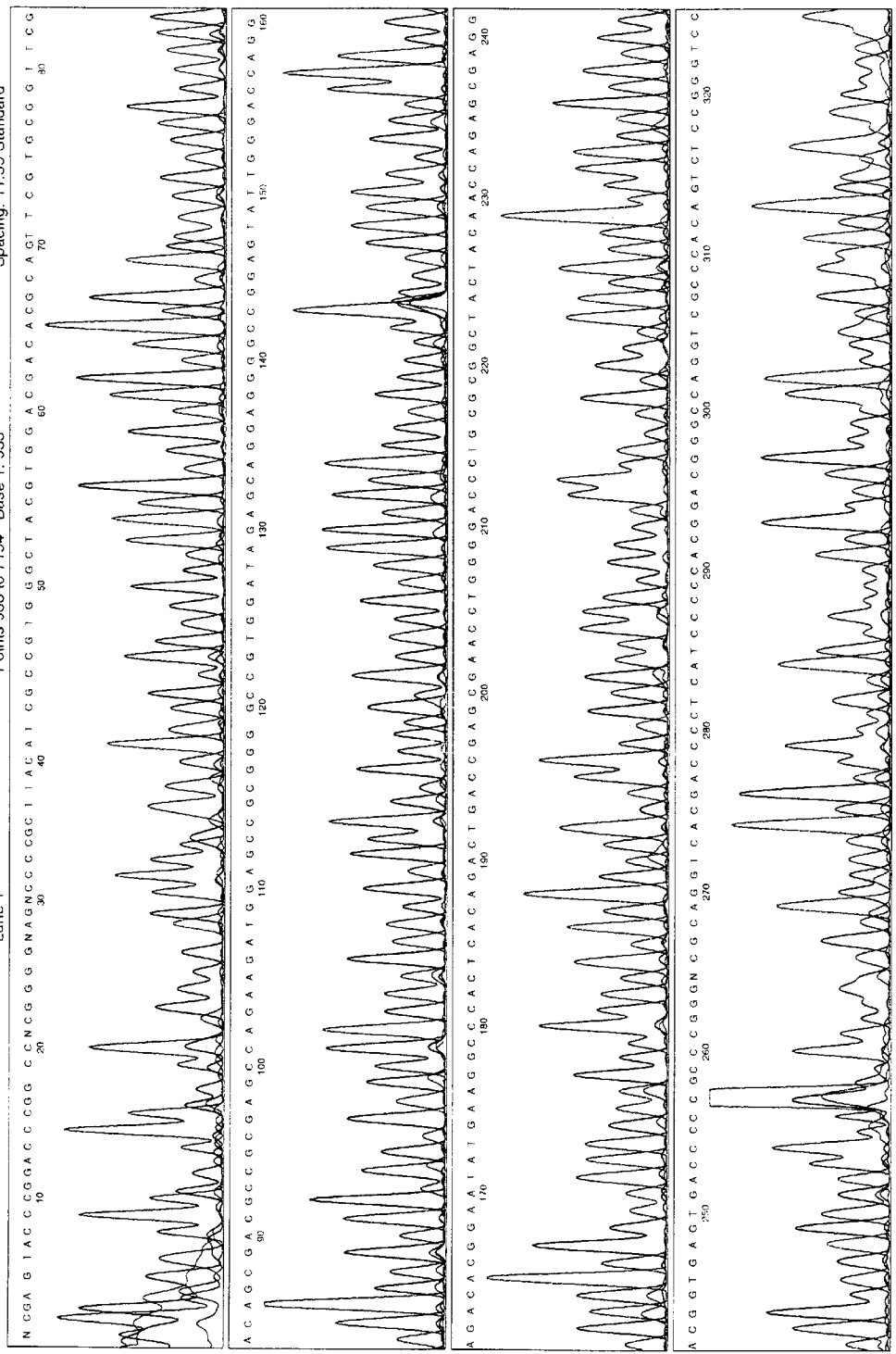
FIG. 3 is the raw sequence of the sense strand of exon 2 of the HLA-A gene.
Figure 4:
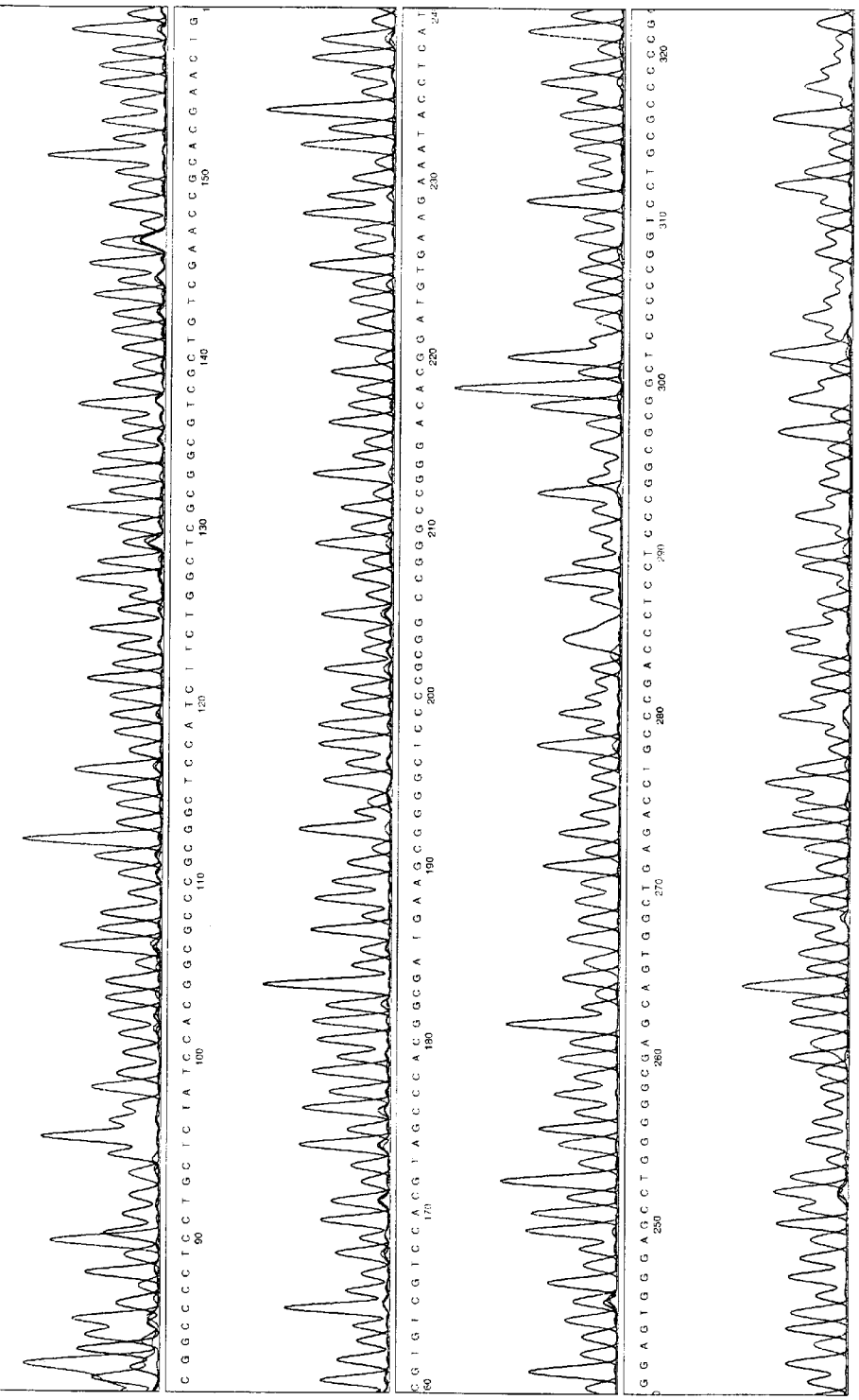
FIG. 4 is the raw sequence of the antisense strand of exon 2 of the HLA-A gene.

FIGS. 3–8 show typing data from the HLA-A class I gene. FIGS. 3 and 4 show the raw sequence of the sense strand and the antisense strand of exon 2 of the HLA-A gene using the sequencing primers SEQ ID #9 and SEQ ID #12, respectively. FIG. 5 shows a sequence alignment of the data from FIGS. 3 and 4 where: line 1 is the reference sequence of the putative allele, HLA-A0101 (Genbank Accession No. M24043); line 2 is the experimentally determined sequence of the sense strand obtained from FIG. 3; line 3 is the experimentally determined sequence of the antisense strand obtained from FIG. 4; and, line 4 is a consensus sequence derived from the sequences in lines 1, 2, and 3 (note that the line numbers 1, 2, 3, and 4 refer to the numbers in the leftmost column of each of the sequence panels in FIG. 5 and each of the following alignment figures, i.e., FIGS. 8, 11, 16, 19, and 21).

Figure 6:
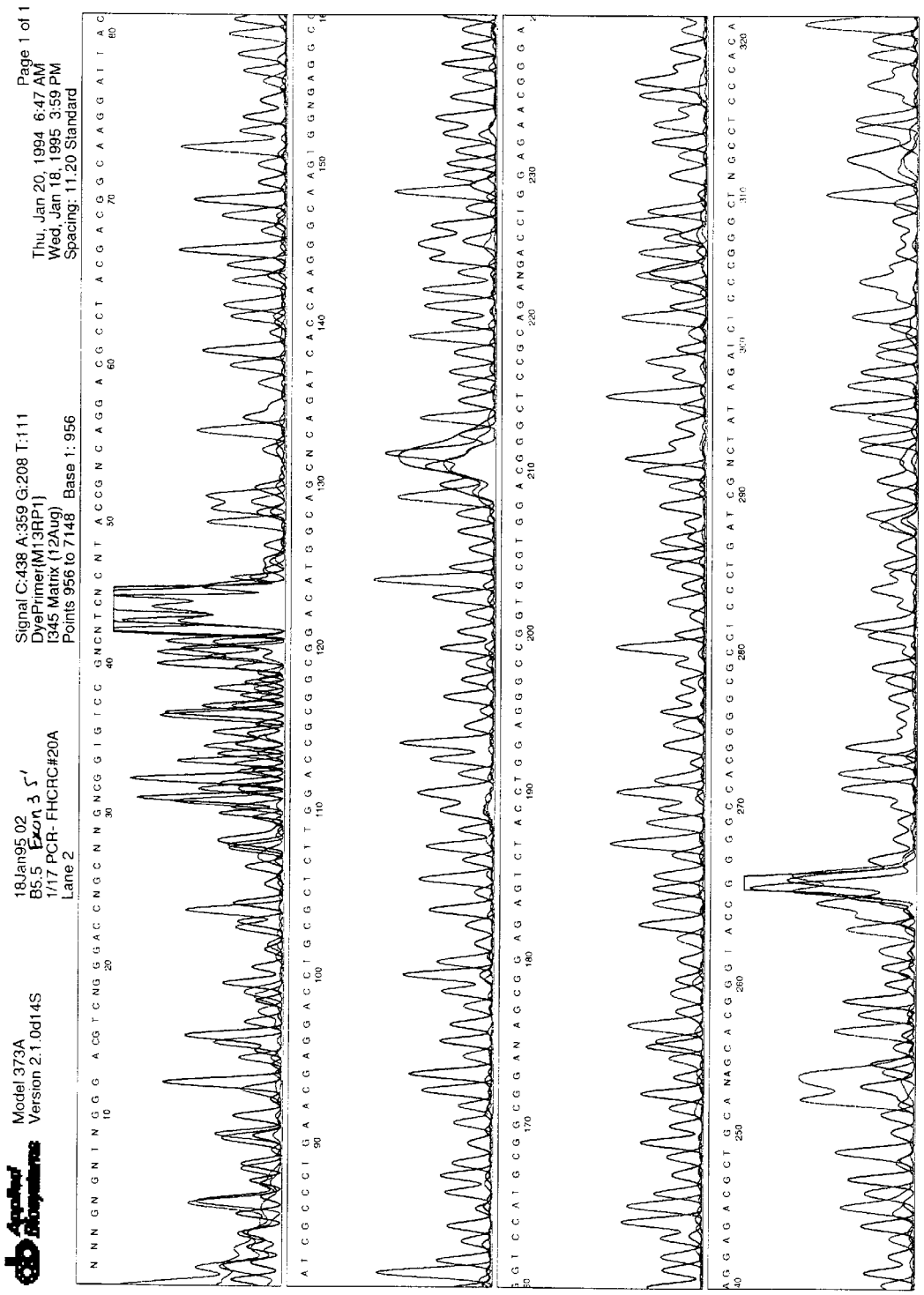
FIG. 6 is the raw sequence of the sense strand of exon 3 of the HLA-A gene.
Figure 7:
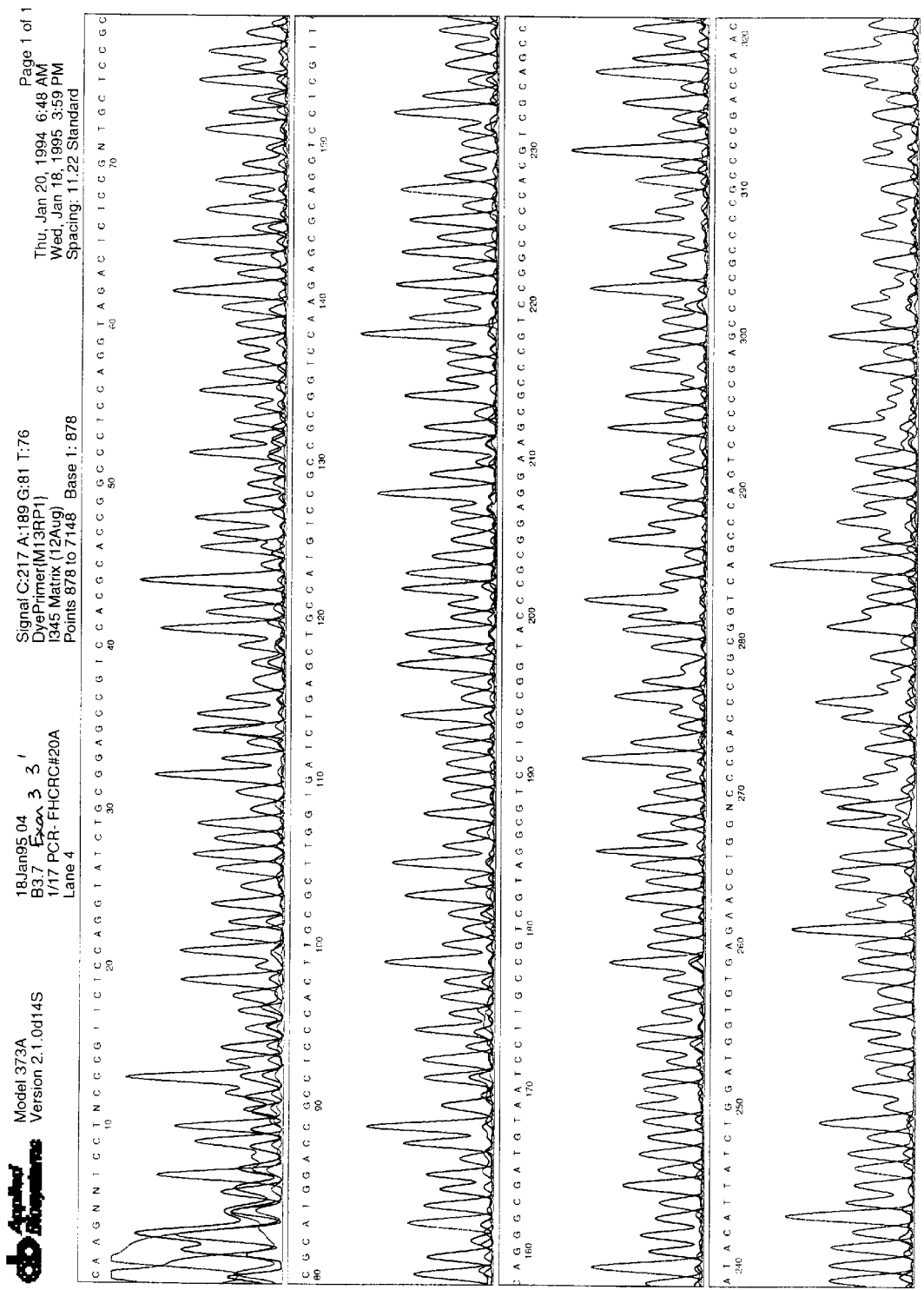
FIG. 7 is the raw sequence of the antisense strand of exon 3 of the HLA-A gene.

FIGS. 6 and 7 show the raw sequence of the sense strand and the antisense strand of exon 3 of the HLA-A gene using the sequencing primers SEQ ID #10 and SEQ ID #14, respectively. FIG. 8 shows a sequence alignment of the data from FIGS. 6 and 7 where: line 1 is the reference sequence of the putative allele, HLA-A0101 (or HLA-A1) (Genbank Accession No. M24043); line 4 is the experimentally determined sequence of the sense strand obtained from FIG. 6; line 5 is the experimentally determined sequence of the antisense strand obtained from FIG. 7; and line 7 is a consensus sequence derived from the sequences in lines 1, 4, and 5.

Figure 9:
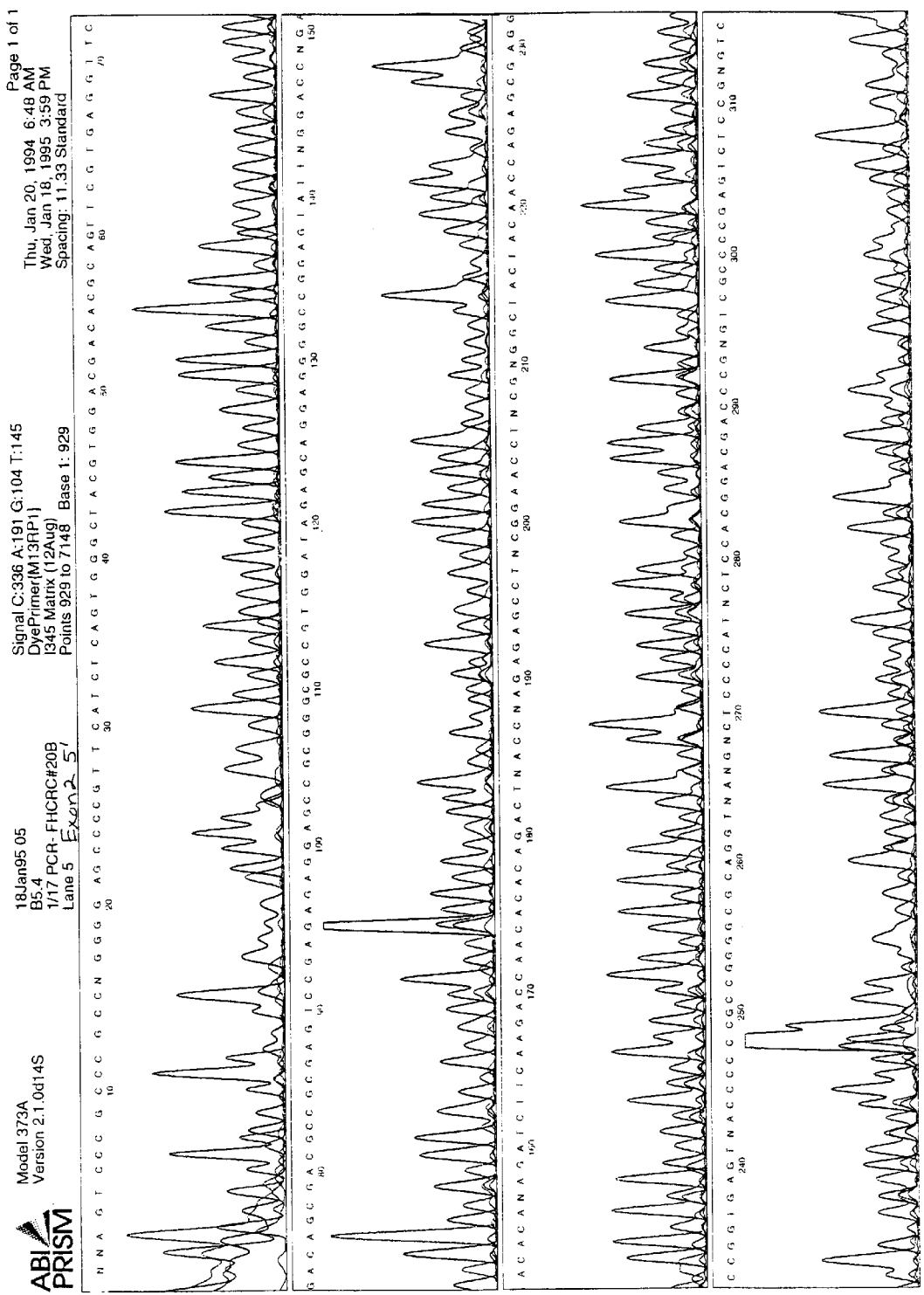
FIG. 9 is the raw sequence of the sense strand of exon 2 of the HLA-B gene.
Figure 10:
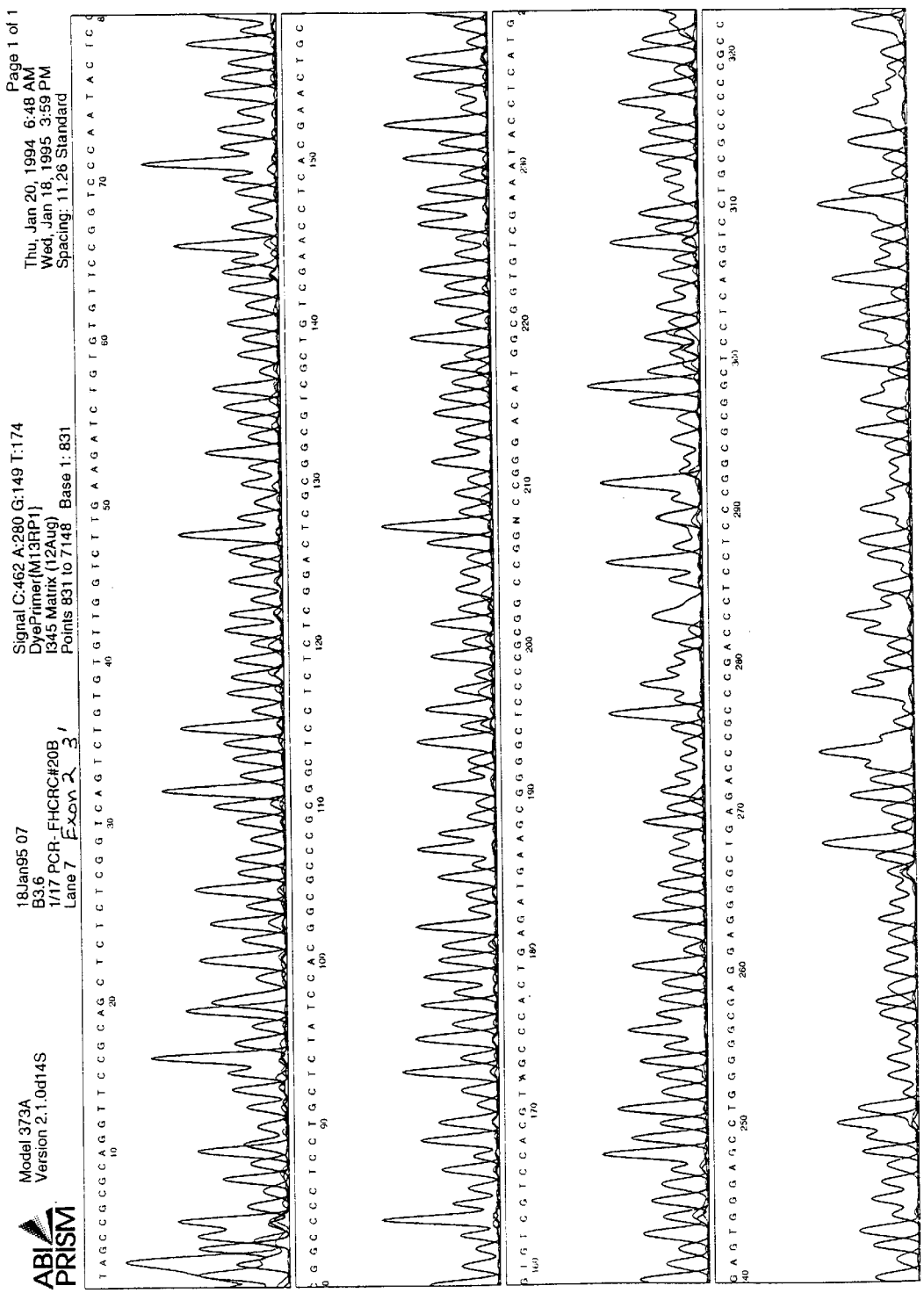
FIG. 10 is the raw sequence of the antisense strand of exon 2 of the HLA-B gene.

FIGS. 9–16 show typing data from the HLA-B class I gene. FIGS. 9 and 10 show the raw sequence of the sense and antisense strands of exon 2 of the HLA-B gene using the sequencing primers SEQ ID #9 and SEQ ID #13, respectively. FIG. 11 shows a sequence alignment of the data from FIGS. 9 and 10 where: line 1 is the reference sequence of the putative allele, HLA-B0801 (Genbank Accession No. M24036); line 2 is the experimentally determined sequence of the sense strand obtained from FIG. 9; line 3 is the experimentally determined sequence of the antisense strand obtained from FIG. 10; and, line 8 is a consensus sequence derived from the sequences in lines 1, 2 and 3.

Figure 12:
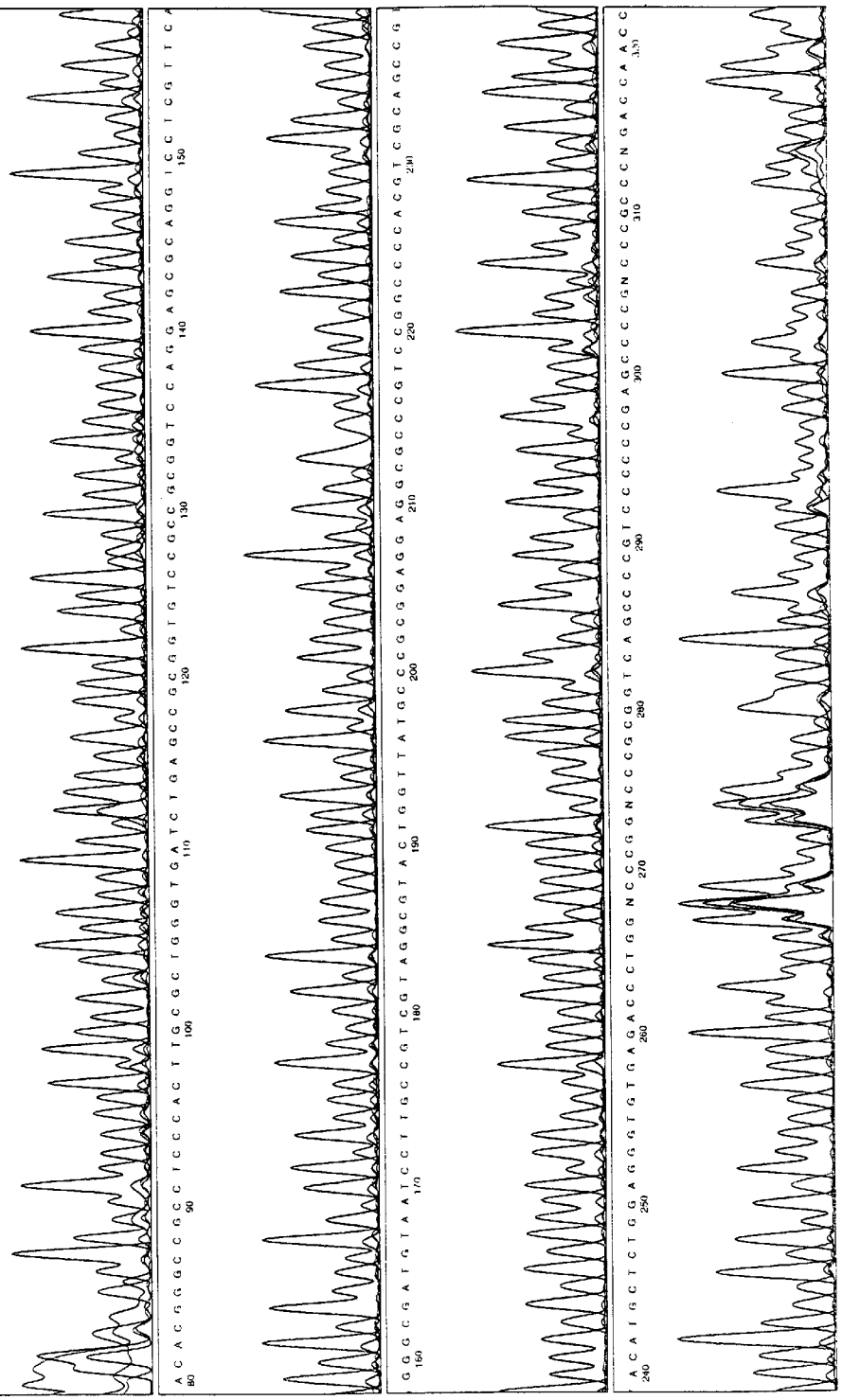
FIG. 12 is the raw sequence of the antisense strand of exon 3 of the HLA-B gene.

FIG. 12 shows the raw sequence of the antisense strand of exon 3 of the HLA-B gene using the sequencing primer SEQ ID #14. FIG. 13 shows a sequence alignment of the data from FIG. 12 where: line 1 is the reference sequence of the putative allele, HLA-B0801 (Genbank Accession No. M24036); line 2 is the experimentally determined sequence of the antisense strand obtained from FIG. 12; and line 3 is a consensus sequence derived from the sequences in lines 1 and 2.

Figure 14:
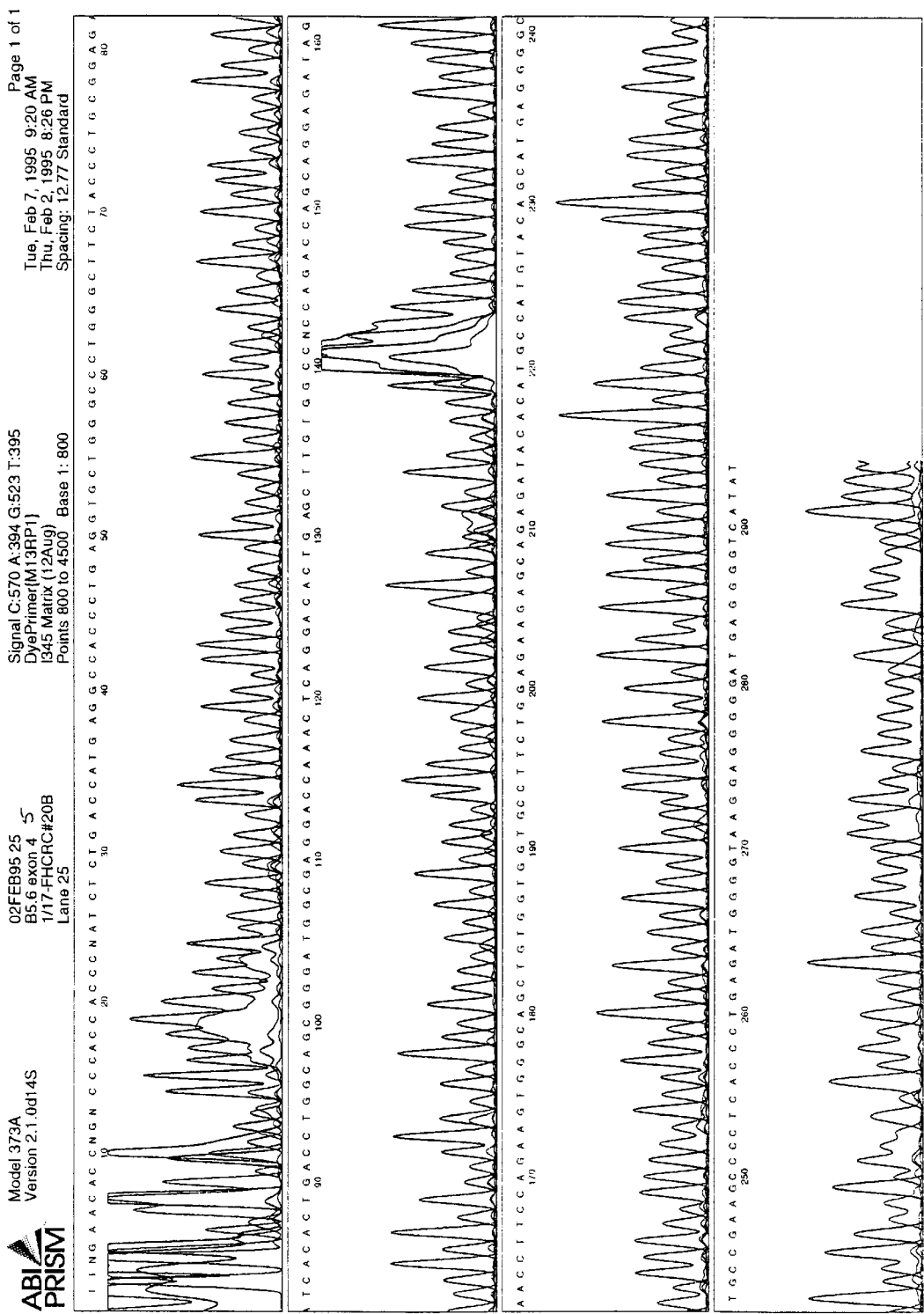
FIG. 14 is the raw sequence of the sense strand of exon 4 of the HLA-B gene.
Figure 15:
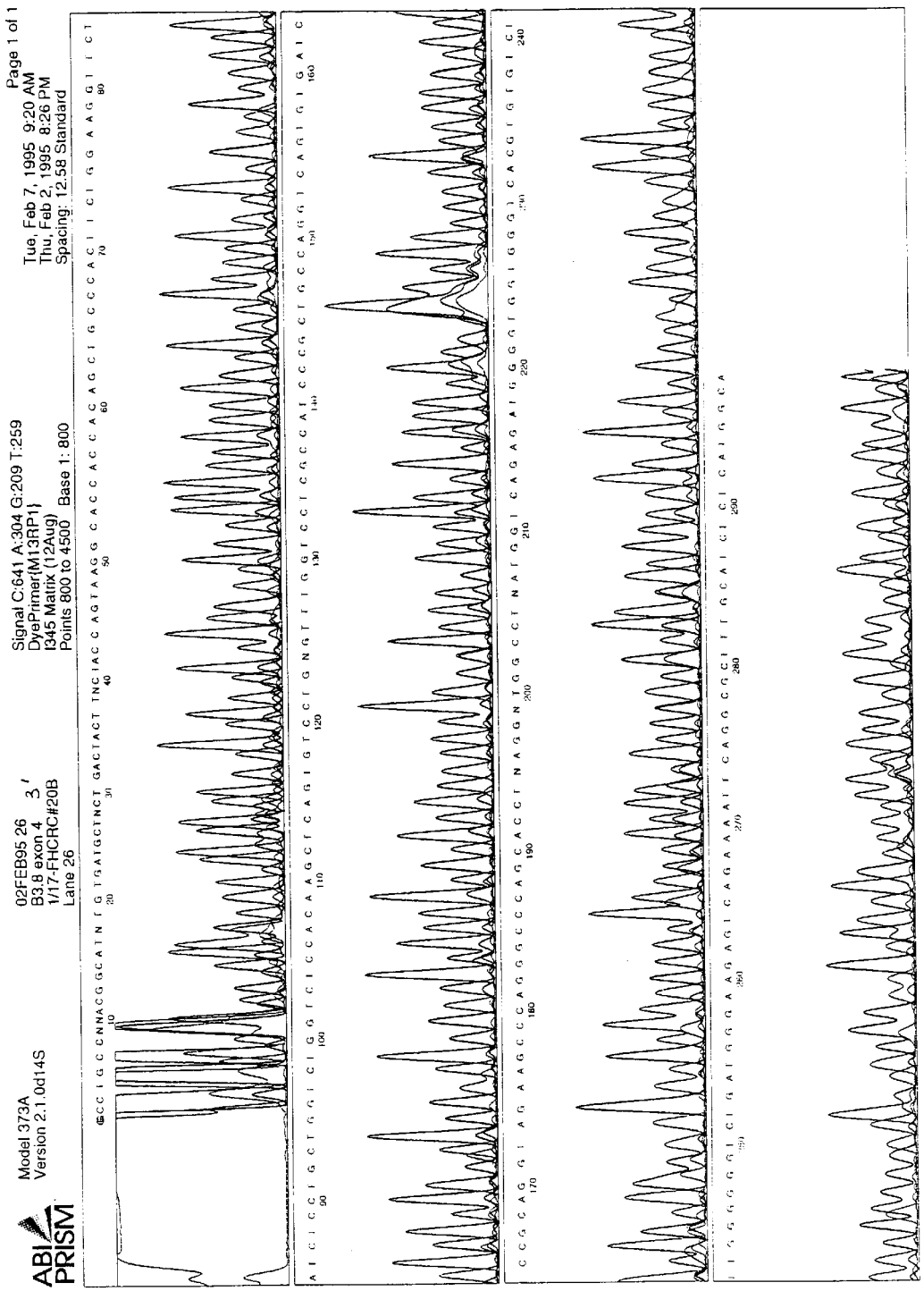
FIG. 15 is the raw sequence of the antisense strand of exon 4 of the HLA-B gene.

FIGS. 14 and 15 show the raw sequence of the sense and antisense strands of exon 4 of the HLA-B gene using the sequencing primers SEQ ID #12 and SEQ ID #15, respectively. FIG. 16 shows a sequence alignment of the data from FIGS. 14 and 15 where: line 6 is the reference sequence of the putative allele, HLA-B0801 (Genbank Accession No. M24036); line 8 is the experimentally determined sequence of the sense strand obtained from FIG. 14; line 9 is the experimentally determined sequence of the antisense strand obtained from FIG. 15; and, line 11 is a consensus sequence derived from the sequences in lines 6, 8 and 9.

Figure 17:
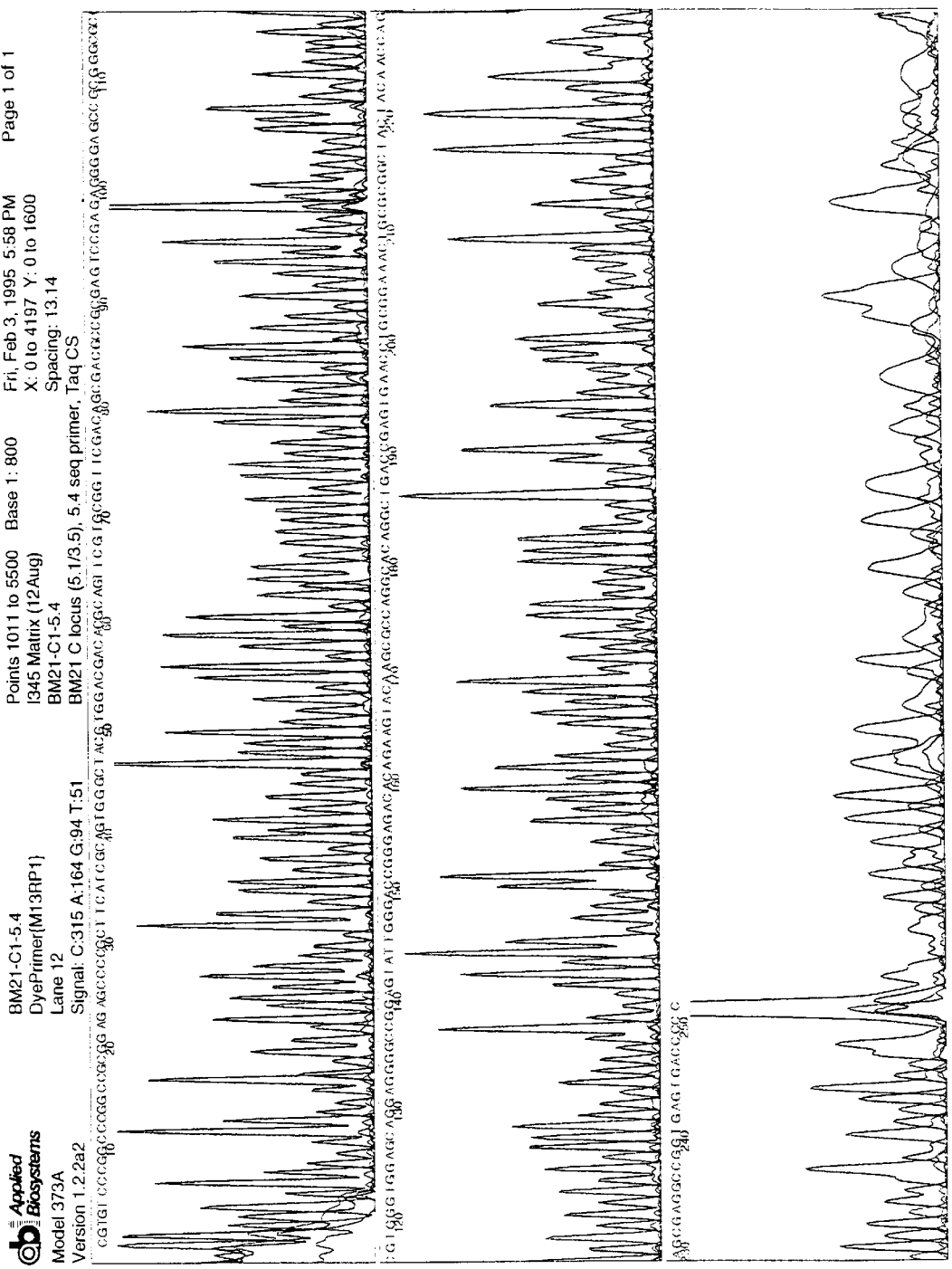
FIG. 17 is the raw sequence of the sense strand of exon 2 of the HLA-C gene.
Figure 18:
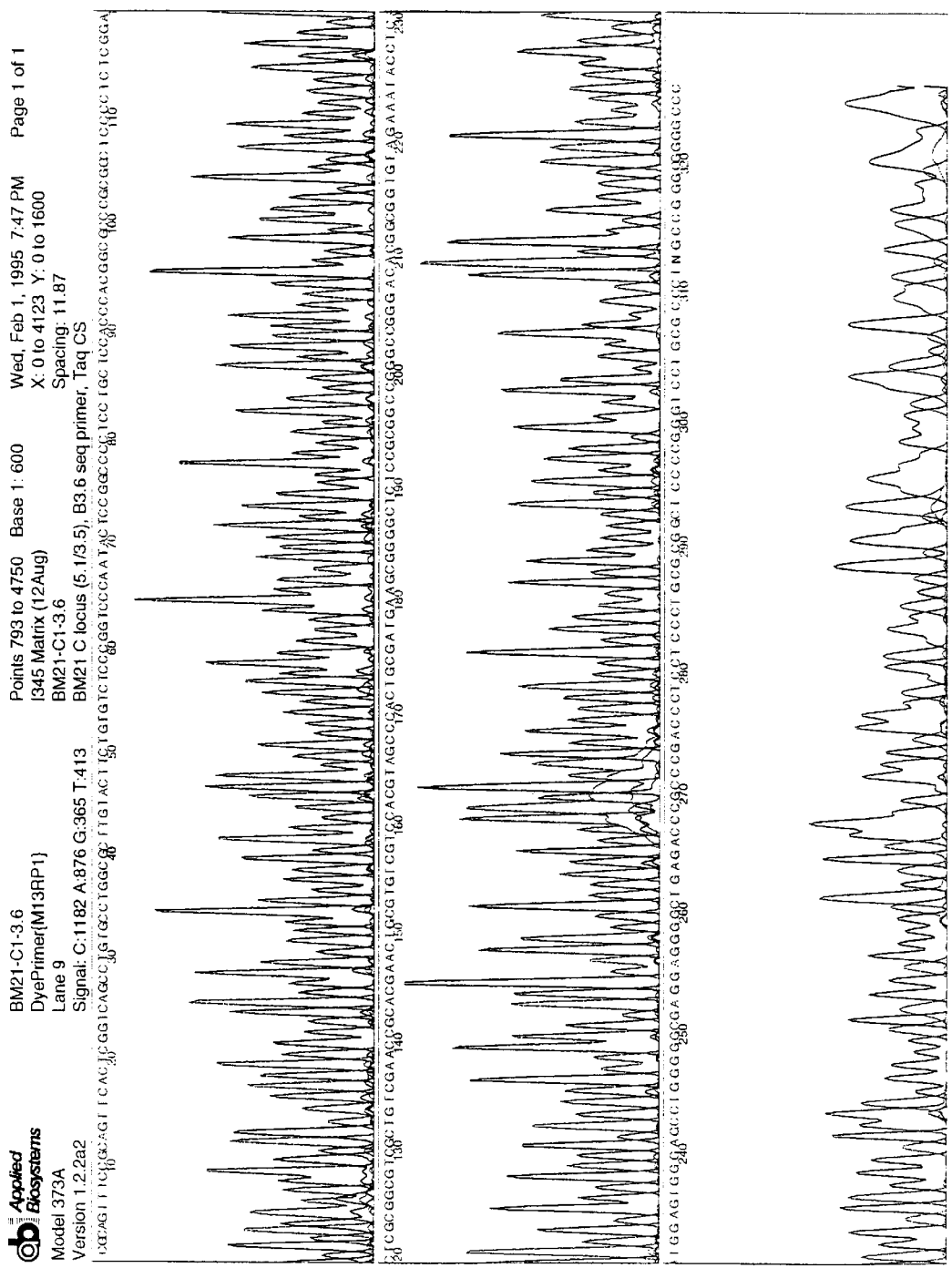
FIG. 18 is the raw sequence of the antisense strand of exon 2 of the HLA-C gene.

FIGS. 17 and 18 show the raw sequence of the sense and antisense strand of exon 2 of the HLA-C gene using the sequencing primers SEQ ID #9 and SEQ ID #13, respectively. FIG. 19 shows a sequence alignment of the data from FIGS. 17 and 18 where: line 1 is the reference sequence of the putative allele, HLA-CW1701 (Genbank Accession No. U06835); line 10 is the experimentally determined sequence of the sense strand obtained from FIG. 17; line 3 is the experimentally determined sequence of the antisense strand obtained from FIG. 18; and, line 11 is a consensus sequence derived from the sequences in lines 1, 3 and 10.

Figure 20:
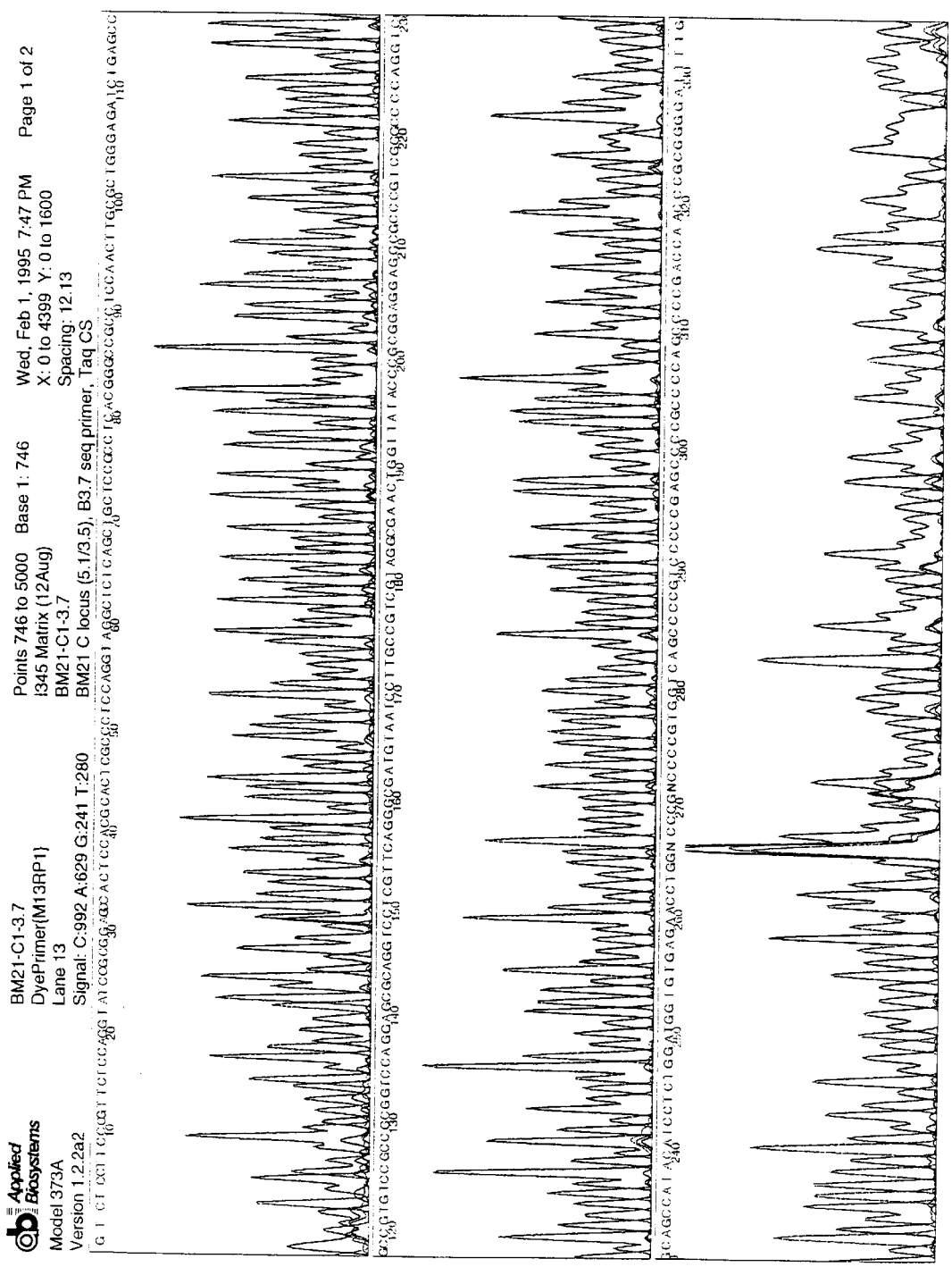
FIG. 20 is the raw sequence of the antisense strand of exon 3 of the HLA-C gene.

FIG. 20 shows the raw sequence of the antisense strand of exon 3 of the HLA-C gene using the sequencing primer SEQ ID #14. FIG. 21 shows a sequence alignment of the data from FIG. 20 where: line 1 is the reference sequence of the putative allele, HLA-C1701 (Genbank Accession No. U06835); line 2 is the experimentally determined sequence of the antisense strand obtained from FIG. 20; and line 4 is a consensus sequence derived from the sequences in lines 1 and 2.

EXAMPLE 3

PCR Amplification of HLA-A and HLA-B Class I Genes

PCR amplification was performed using a Perkin-Elmer 9600 thermal cycler. The amplification was performed with a wax-barrier hot start using Ampliwax™ wax pellets (PE p/n N808-0100). The amplification was performed on human genomic DNA that was purified from peripheral blood cells using the salting-out method, e.g., Miller et al., supra. The average length of the purified genomic DNA was estimated to be at least 5 kilobases. The amplification primers used for amplifying each of the HLA-A and HLA-B genes are shown in Table V below.

TABLE V

| | | Amplification Primers | | |
|---|---|---|---|---|
| SEQ ID | Gene | Exon | Strand[c] | Sequence[a,b] |
| SEQ ID #1 | HLA-A | 1 | Antisense | CGCCGAGGATGGCCGTC |
| SEQ ID #2 | HLA-A | 5 | Sense | GGAGAACCAGGCCAGCAATGATGCCC |

TABLE V-continued

Amplification Primers

| SEQ ID | Gene | Exon | Strand[c] | Sequence[a,b] |
|---|---|---|---|---|
| SEQ ID #3 | HLA-A | 5 | Sense | GGAGAACTAGGCCAGCAATGATGCCC |
| SEQ ID #21 | HLA-B | 1 | Antisense | CCTCCTGCTGCTCTCGGC |
| SEQ ID #22 | HLA-B | 1 | Antisense | CCTCCTGCTGCTCTCGGGA |
| SEQ ID #23 | HLA-B | 1 | Antisense | GCTGCTCTGGGGGGCAG |
| SEQ ID #24 | HLA-B | 5 | Sense | GCTCCGATGACCACAACTGCT | a. Underlined nucleotides indicate a degenerate position.
b. Sequences SEQ ID #2 and SEQ ID #3, and sequences SEQ ID #21–24 make up degenerate primer sets wherein each member of a primer set is present in an equimolar concentration.
c. The Strand refers to the strand of the target DNA duplex to which the amplification primer binds, i.e., an antisense primer binds to the antisense strand of the target.

The PCR reaction for the HLA-A gene was prepared as follows. Four μl of the 5× concentrated PCR buffer from Example 1 was mixed with 5 μl of a 10 mM deoxynucleotide triphosphate (dNTP) solution (2.5 mM each of dATP, dCTP, dGTP, and dTTP), 1 μl of a 10 pMole/μl solution of the SEQ ID #2 and SEQ ID #3 amplification primer(s), 2.5 μl of a 100 ng/μl solution of the purified human genomic DNA, and, a volume of sterile double-distilled (dd) H$_2$O sufficient to result in a final volume of 30 μl.

Next, the above-prepared 30 μl reaction mixture was added to a Microamp reaction tube (PE p/n N801-0533, N801-0534, N801-0540) containing one Ampliwax™ pellet (PE p/n N808-0100). The tube was capped, briefly spun in a centrifuge at 3000 rpm to remove all droplets from the side of the tube, then heated to 65° C. for 5 minutes to melt the Ampliwax™ pellet. The tube was then cooled to 4° C., thus forming a wax liquid barrier.

Above the wax barrier was added a solution containing 6 μl of the 5× concentrated PCR buffer, 1 μl of a 10 pMole/μl solution of the SEQ ID #1 amplification primer, 1U of AmpliTaq™ DNA polymerase, and a volume of sterile double-distilled (dd) H$_2$O sufficient to result in a final volume of 30 μl.

The PCR reaction for the HLA-B gene was prepared as follows. Four μl of the 5× concentrated PCR buffer from Example 1 was mixed with 5 μl of a 10 mM deoxynucleotide triphosphate (dNTP) solution (2.5 mM each of dATP, dCTP, dGTP, and dTTP), 1 μl of a 10 pMole/μl solution of the SEQ ID #24 amplification primer, 2.5 μl of a 100 ng/μl solution of the purified human genomic DNA, and, a volume of sterile double-distilled (dd) H$_2$O sufficient to result in a final volume of 20 μl.

Next, the above-prepared 20 μl reaction mixture was added to a Microamp reaction tube containing one Ampliwax™ pellet. The tube was capped, briefly spun in a centrifuge at 3000 rpm to remove all droplets from the side of the tube, then heated to 65° C. for 5 minutes to melt the Ampliwax™ pellet. The tube was then cooled to 4° C., thus forming a wax liquid barrier.

Above the wax barrier was added a solution containing 6 μl of the 5× concentrated PCR buffer, 1 μl of a 15 pMole/μl solution of the SEQ ID #21, SEQ ID #22, and SEQ ID #23 amplification primers, 1U of AmpliTaq™ DNA polymerase, and a volume of sterile double-distilled (dd) H$_2$O sufficient to result in a final volume of 30 μl.

The above-prepared reaction tubes were placed in a Perkin-Elmer 9600 thermal cycler, denatured at 98° C. for 20 s, then subjected to the following thermal cycle program: (i) 98° C. for 5 s, 65° C. for 30 s, 72° C. for 2 min, where the cycle was repeated eight times; followed by (ii) 96° C. for 5 s, 60° C. for 30 s, 72° C. for 2 min, where the cycle was repeated 32 times.

Following thermocycling, 8 μl of each of the reactions was analyzed by agarose gel electrophoresis to ensure proper PCR amplification. A 0.7% agarose gel was used containing ethidium bromide at 0.8 μg/ml and TBE buffer (89 mM Tris-HCl, 89 mM Boric Acid, 2 mM Na$_2$EDTA, pH8.3) as both the gel and running buffer. The gel was electrophoresed at 7 V/cm for 2 hrs and visualized using a UV transilluminator. A band at about 2.0 kb for the HLA-A, or -B, products was seen indicating successful amplification of each of the specific genes (sizes based on internal size standards).

EXAMPLE 4

DNA Sequencing of Exons 2, 3, and 4 of the HLA-A and HLA-B Class I Genes Using the Amplification Products from Example 3

Sequencing was performed with no purification of the PCR products using the AmpliTaq® DNA polymerase FS enzyme from Perkin-Elmer (p/n 402114). The sequencing protocol used was that suggested by Perkin-Elmer with some minor modifications, e.g., ABI Prism Dye Primer Cycle Sequencing Core Kit Protocol, Revision A, July 1995, such reference incorporated herein by reference.

The sequencing primers shown below in Table VI were used to sequence exons 2 and 3 of the HLA-A and HLA-B genes.

TABLE VI

DNA Sequencing Primers

| SEQ ID | Gene | Exon | Strand[a] | Sequence[b,c] |
|---|---|---|---|---|
| SEQ ID #25 | A | 2 | Antisense | TCGGGCAGGTCTCAGCC |
| SEQ ID #26 | A | 2 | Antisense | TCGGGCGGGTCTCAGCC |
| SEQ ID #12 | A,B | 2 | Sense | CACTCACCGGCCTCGCTCTGG |
| SEQ ID #27 | A | 3 | Antisense | GGGCTCGGGGACCGGG |
| SEQ ID #28 | A | 3 | Antisense | GGGCTCGGGGACTGGG |
| SEQ ID #29 | A | 3 | Sense | GAGGCGCCCGTGGC |
| SEQ ID #9 | B | 2 | Antisense | CTCGCCCCCAGGCTCCCAC |
| SEQ ID #10 | B | 3 | Antisense | GCGGGGCGGGTCCAGG |
| SEQ ID #13 | B | 3 | Sense | CCACTGCCCCTGGTACCCG | a. The Strand refers to the strand of the DNA duplex to which the sequencing primer binds.
b. Note that the primer sequences include a CAGGA leader sequence at the 5'-end that was added reduce the effect of interaction of the dye label with the primer. The CGGA leader sequence was not used for controlling hybridization specificity.
c. Sequences SEQ ID 25 and SEQ ID 26, and sequences SEQ ID 27 and SEQ ID 28 make up degenerate primer sets werein each member of a primer set is present in an equimolar concentration.

Each of the primers in Table VI is labeled at the 5'-end with one of the four fluorescent dyes 5-carboxy-fluorescein (FAM), 2',7'-dimethoxy-4', 5'-dichloro-6-carboxy-fluorescene (JOE), N,N,N',N'-tetramethyl-6-carboxyrhodamine (TAMRA), and 6-carboxy-X-rhodamine (ROX), e.g., U.S. Pat. No. 4,855,225.

The following FIGS. 22–33 show examples of HLA class I typing data collected using the protocols of Examples 3 and 4.

Figure 22:
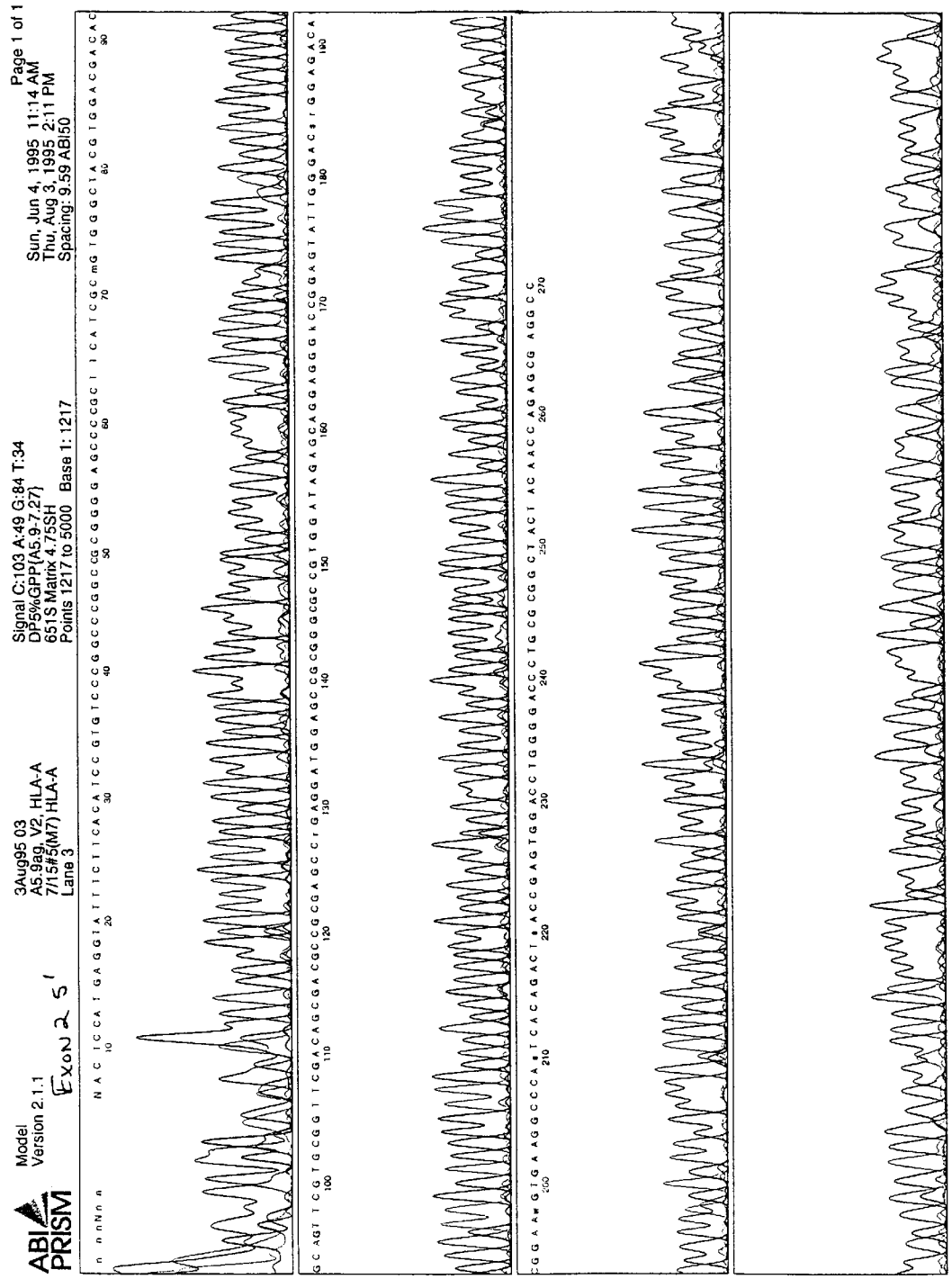
FIG. 22 is the raw sequence of the sense strand of exon 2 of the HLA-A gene.
Figure 23:
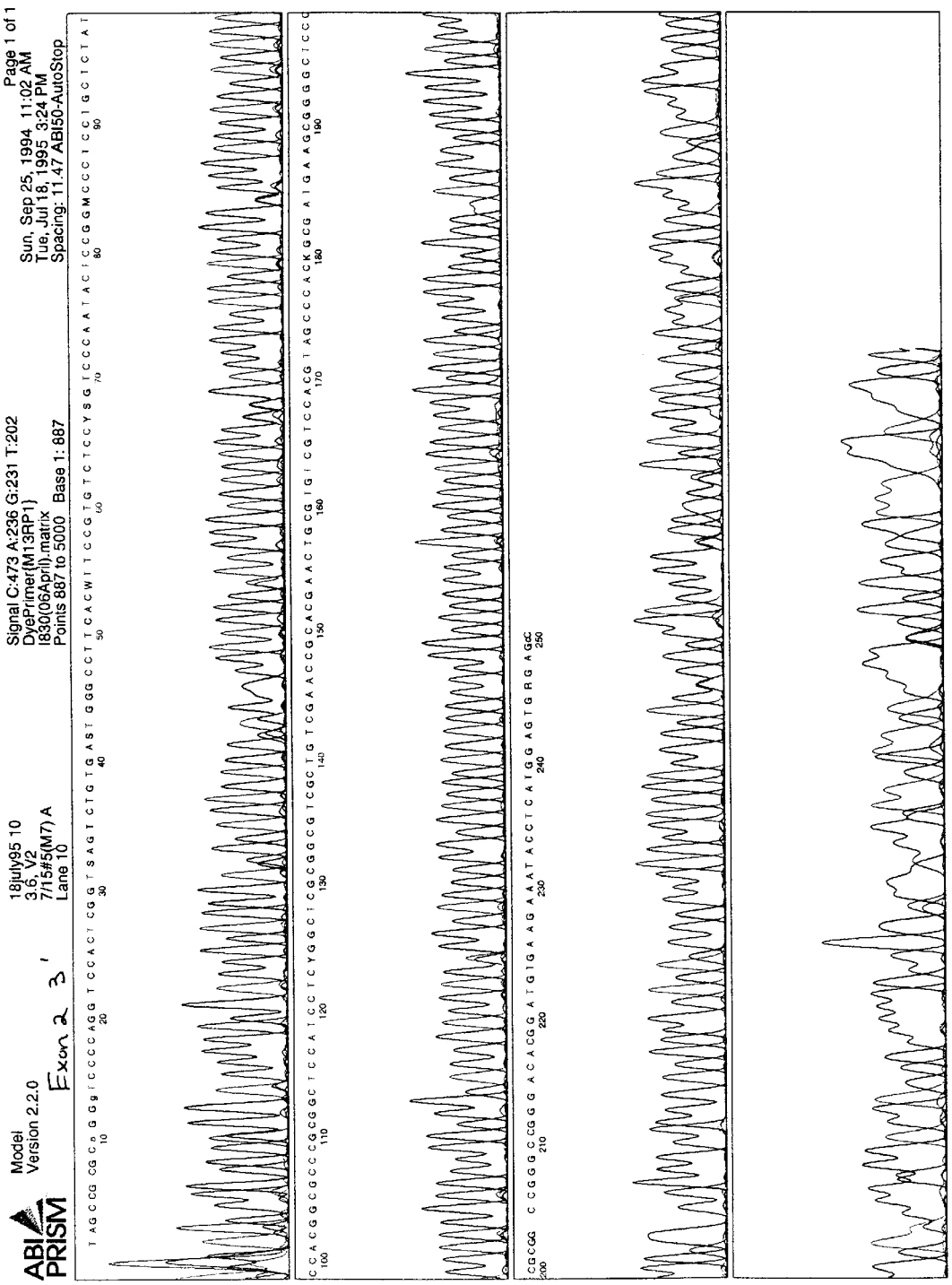
FIG. 23 is the raw sequence of the antisense strand of exon 2 of the HLA-A gene.

FIGS. 22–27 show typing data from the HLA-A class I gene. FIGS. 22 and 23 show the raw sequence of the sense strand and the antisense strand of exon 2 of the HLA-A gene, respectively. Sequencing primers SEQ ID #25 and SEQ ID #26 were used to obtain the sequence of the the sense strand shown in FIG. 22, and sequencing primer SEQ ID #12 was used to obtain the sequence of the antisense strand shown in FIG. 23. FIG. 24 shows a sequence alignment of the data from FIGS. 22 and 23 where: lines 1 and 2 are the reference sequence of the putative diploid alleles, HLA-A0202 and HLA-A0301, respectively; line 3 is the experimentally determined sequence of the sense strand obtained from FIG. 22; and line 4 is the experimentally determined sequence of the antisense strand obtained from FIG. 23 (note that the line numbers 1, 2, 3, and 4 refer to the numbers in the leftmost column of each of the sequence panels in FIG. 24).

Figure 25:
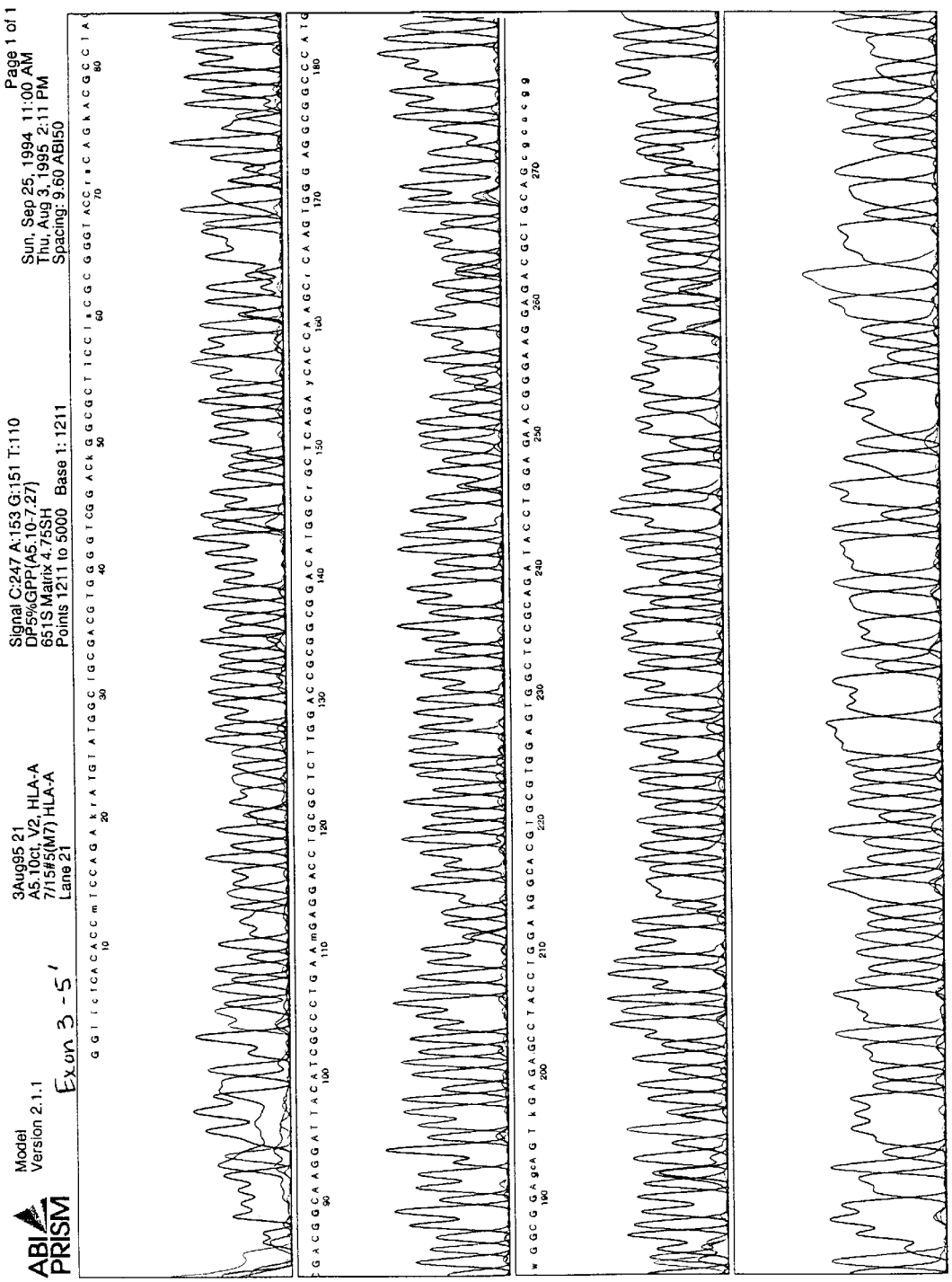
FIG. 25 is the raw sequence of the sense strand of exon 3 of the HLA-A gene.
Figure 26:
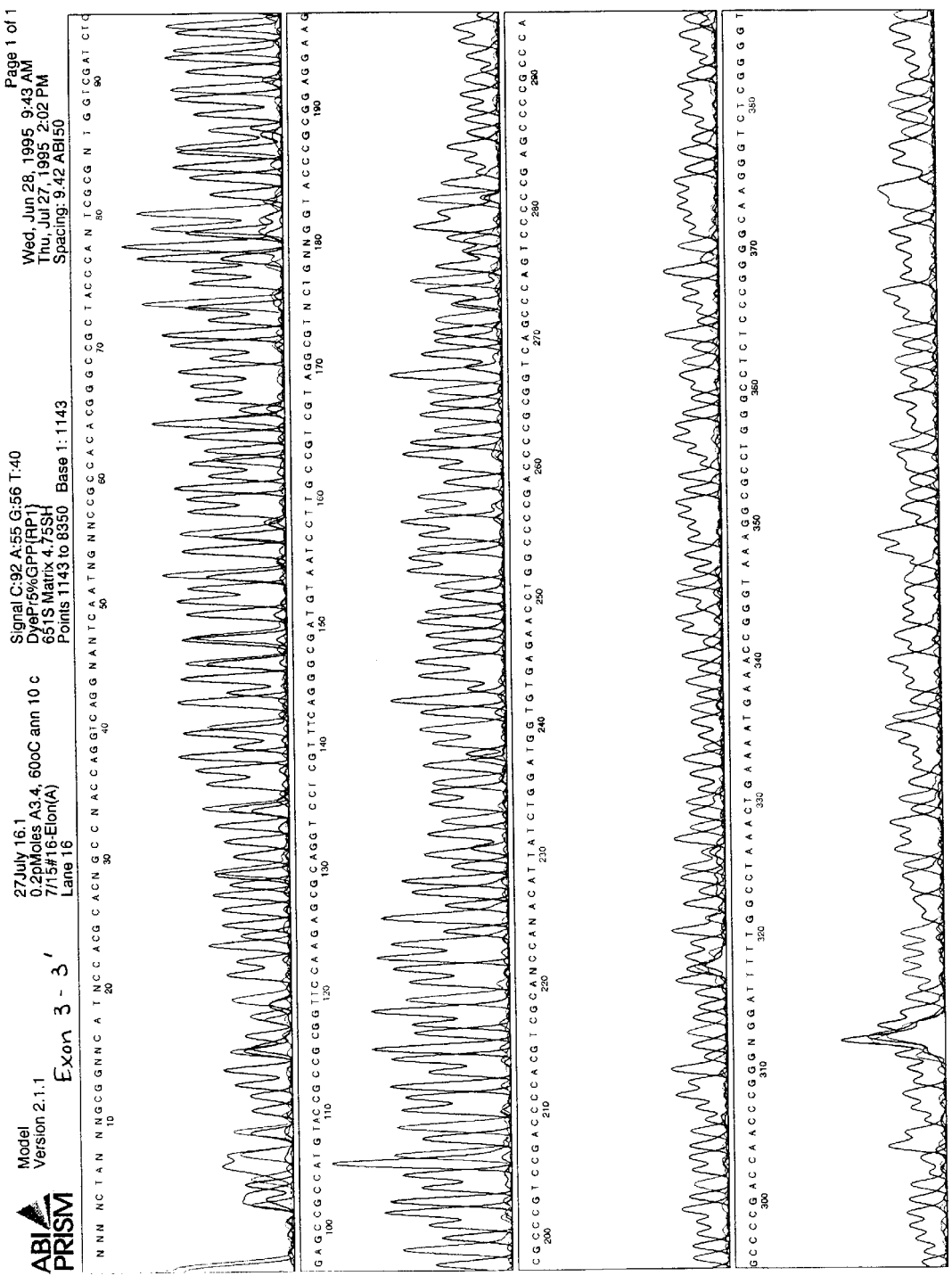
FIG. 26 is the raw sequence of the antisense strand of exon 3 of the HLA-A gene.

FIGS. 25 and 26 show the raw sequence of the sense strand and the antisense strand of exon 3 of the HLA-A gene, respectively. Sequencing primers SEQ ID #27 and SEQ ID #28 were used to obtain the sequence of the the sense strand shown in FIG. 25, and sequencing primer SEQ ID #29 was used to obtain the sequence of the antisense strand shown in FIG. 26. FIG. 27 shows a sequence alignment of the data from FIGS. 25 and 26 where: lines 1 and 2 are the reference sequence of the putative diploid alleles, HLA-A0202 and HLA-A0301, respectively; line 3 is the experimentally determined sequence of the sense strand obtained from FIG. 25; and line 4 is the experimentally determined sequence of the antisense strand obtained from FIG. 26 (note that the line numbers 1, 2, 3, and 4 refer to the numbers in the leftmost column of each of the sequence panels in FIG. 24).

Figure 28:
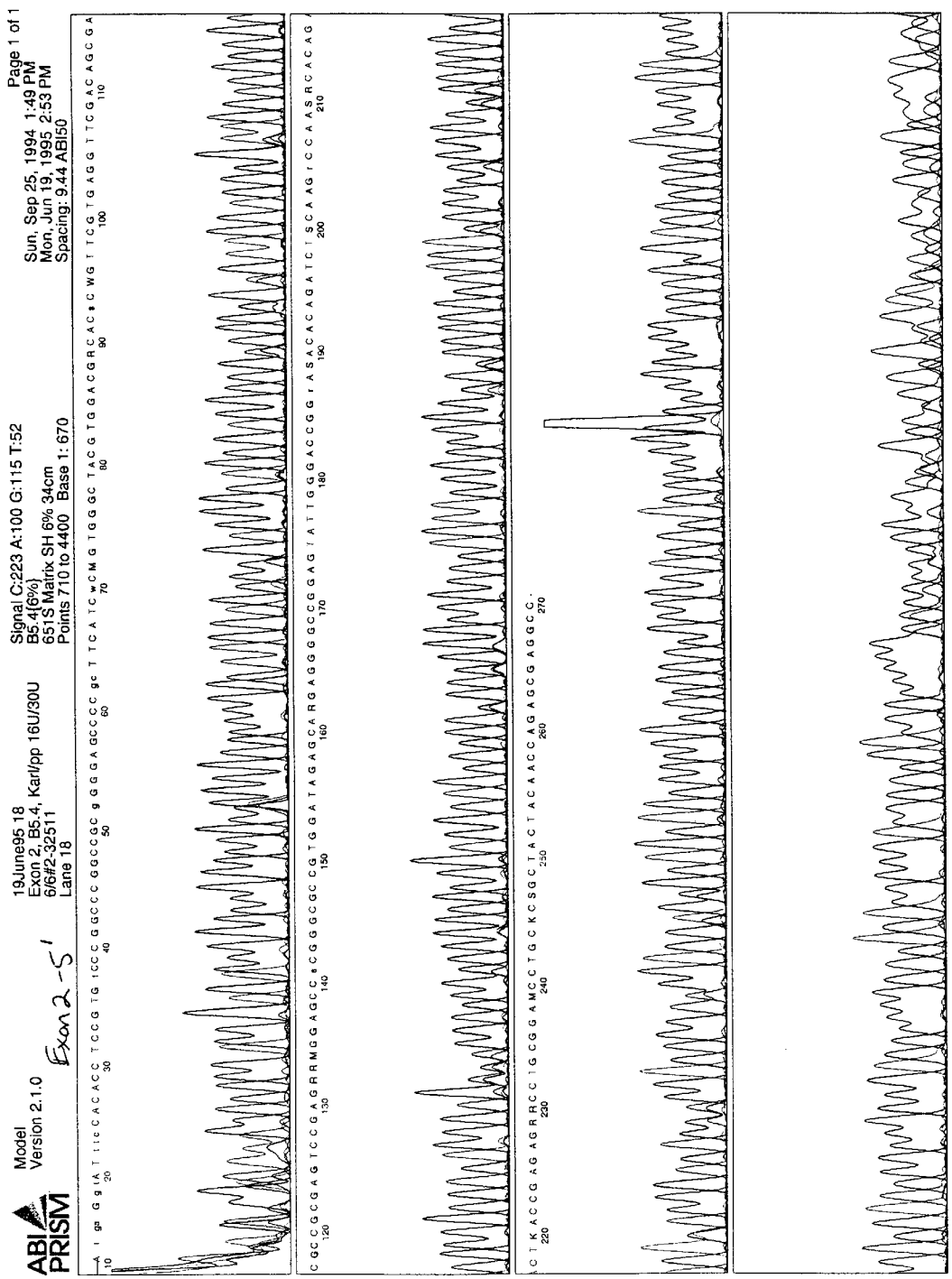
FIG. 28 is the raw sequence of the sense strand of exon 2 of the HLA-B gene.
Figure 29:
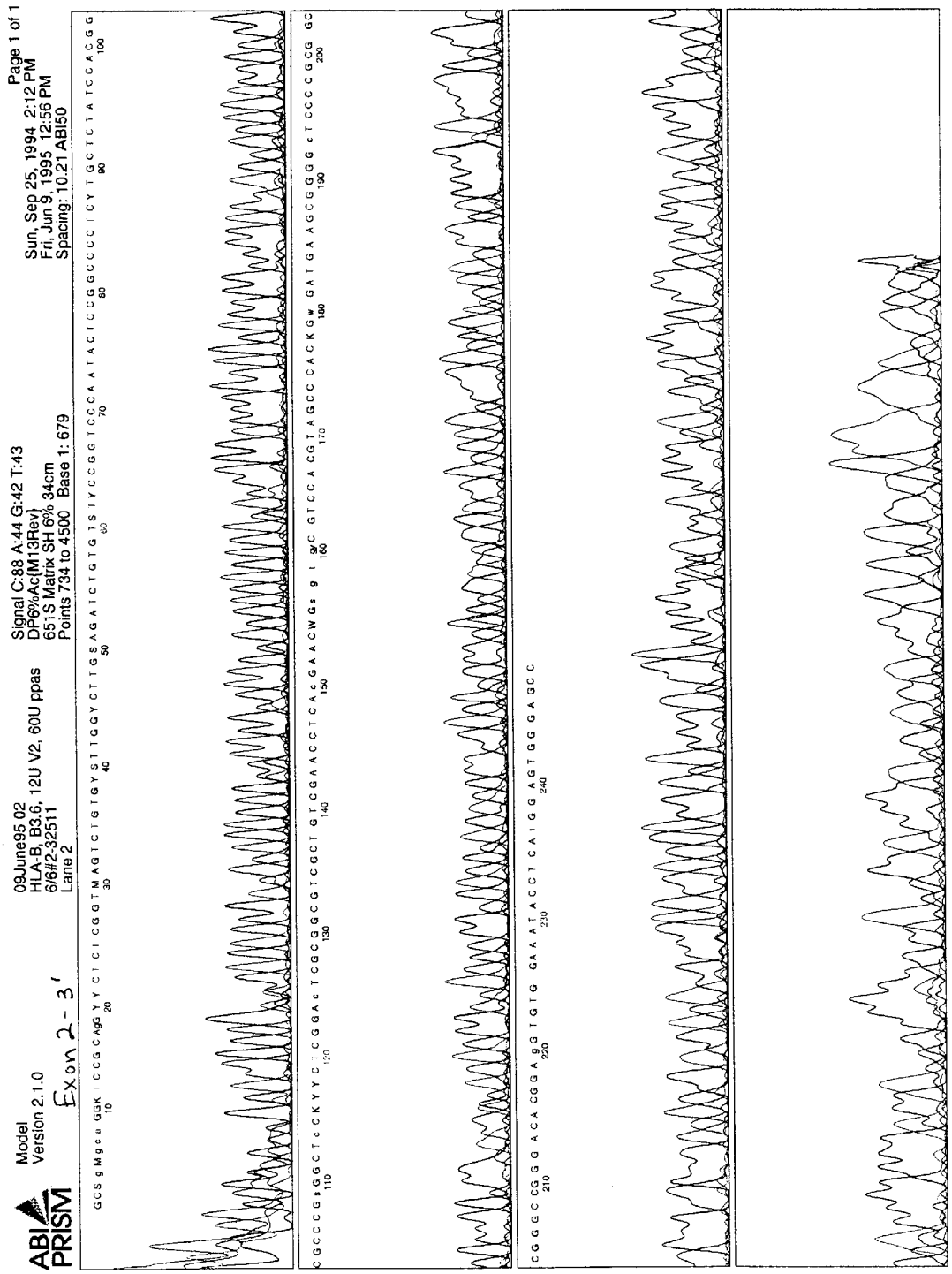
FIG. 29 is the raw sequence of the antisense strand of exon 2 of the HLA-B gene.

FIGS. 28–33 show typing data from the HLA-B class I gene. FIGS. 28 and 29 show the raw sequence of the sense strand and the antisense strand of exon 2 of the HLA-B gene, respectively. Sequencing primer SEQ ID #9 was used to obtain the sequence of the the sense strand shown in FIG. 28, and sequencing primer SEQ ID #12 was used to obtain the sequence of the antisense strand shown in FIG. 29. FIG. 30 shows a sequence alignment of the data from FIGS. 28 and 29 where: lines 19 and 20 are the reference sequence of the putative diploid alleles, HLA-B-1801 and HLA-B27052, respectively; line 14 is the experimentally determined sequence of the sense strand obtained from FIG. 28; and line 16 is the experimentally determined sequence of the antisense strand obtained from FIG. 29 (note that the line numbers 19, 20, 14, and 16 refer to the numbers in the leftmost column of each of the sequence panels in FIG. 30).

Figure 31:
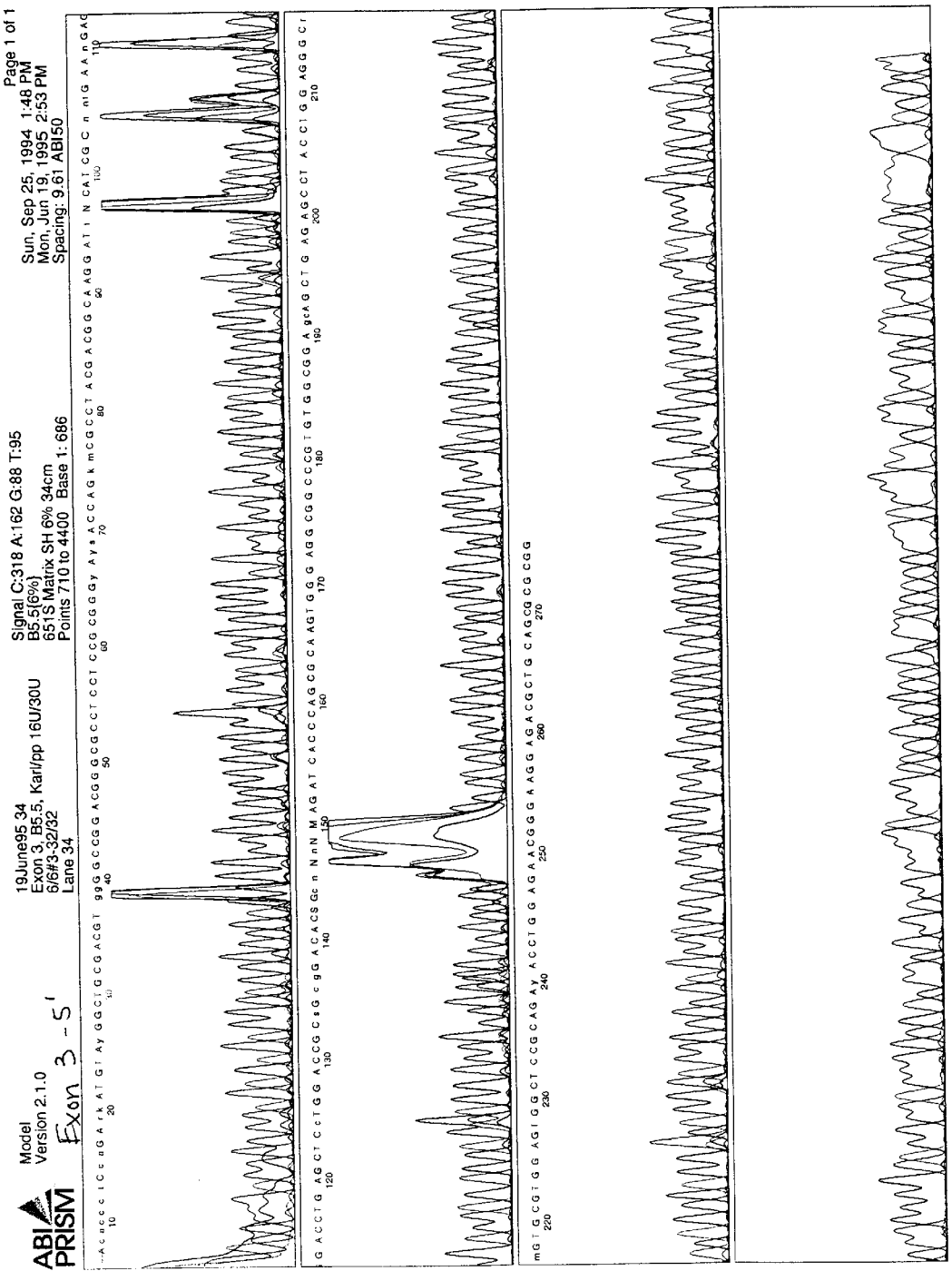
FIG. 31 is the raw sequence of the sense strand of exon 3 of the HLA-B gene.
Figure 32:
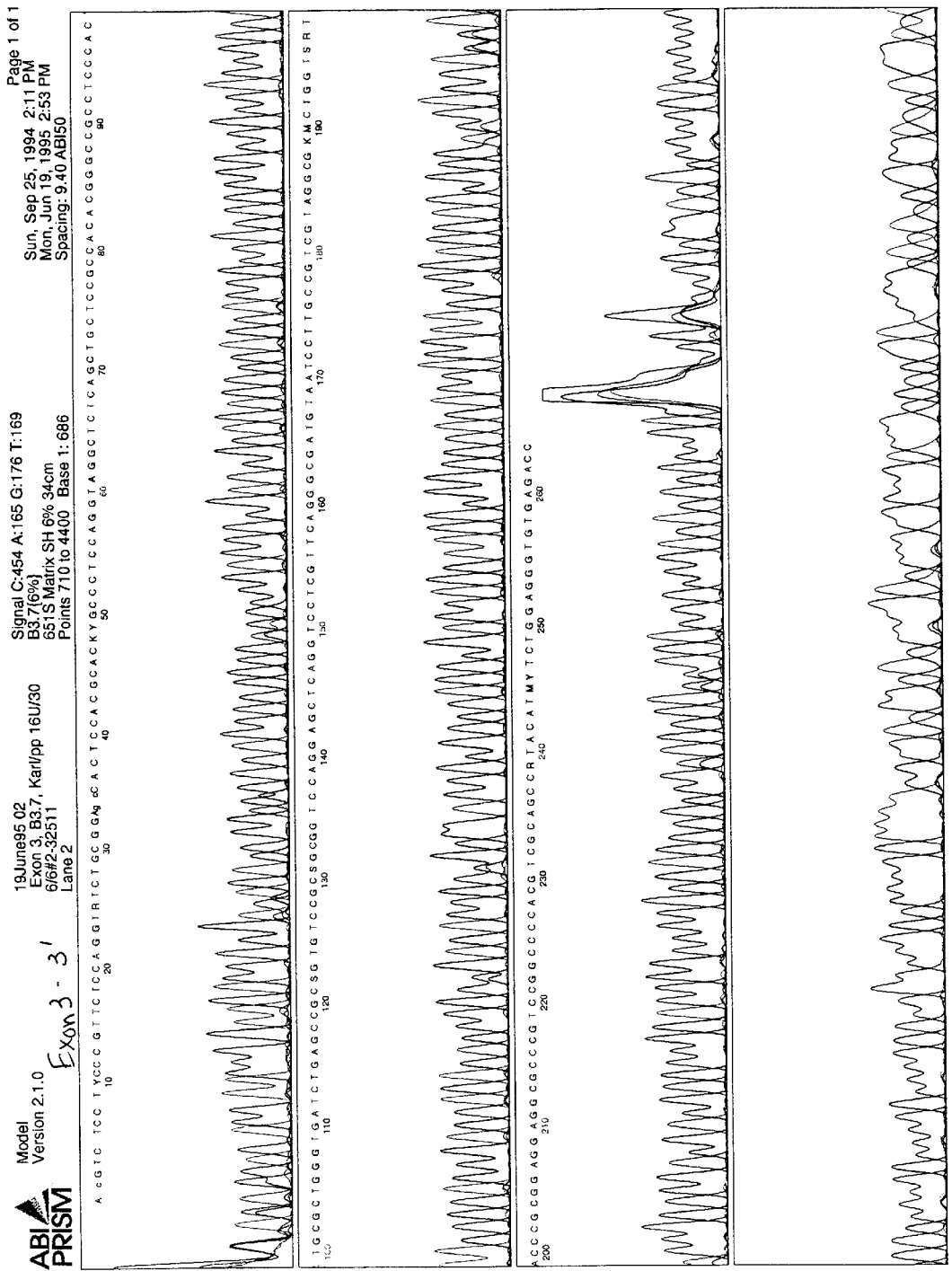
FIG. 32 is the raw sequence of the antisense strand of exon 3 of the HLA-B gene.

FIGS. 31 and 32 show the raw sequence of the sense strand and the antisense strand of exon 3 of the HLA-B gene, respectively. Sequencing primer SEQ ID #10 was used to obtain the sequence of the the sense strand shown in FIG. 31, and sequencing primer SEQ ID #13 was used to obtain the sequence of the antisense strand shown in FIG. 32. FIG. 33 shows a sequence alignment of the data from FIGS. 31 and 32 where: lines 1 and 2 are the reference sequence of the putative diploid alleles, HLA-B1801 and HLA-B27052, respectively; line 3 is the experimentally determined sequence of the sense strand obtained from FIG. 31; and line 4 is the experimentally determined sequence of the antisense strand obtained from FIG. 32 (note that the line numbers 1, 2, 3, and 4 refer to the numbers in the leftmost column of each of the sequence panels in FIG. 33).

EXAMPLE 5

PCR Amplification of HLA-C Class I Genes

PCR amplification was performed using a Perkin-Elmer 9600 thermal cycler. The amplification was performed with a wax-barrier hot start using Ampliwax™ wax pellets (PE p/n N808-0100). The amplification was performed on human genomic DNA that was purified from peripheral blood cells using the salting-out method, e.g., Miller et al., supra. The average length of the purified genomic DNA was estimated to be at least 5 kilobases.

The amplification primers used for amplifying the HLA-C gene are shown in Table VII below.

TABLE VII

Amplification Primers

| SEQ ID | Gene | Exon | Strand | Sequence[a] |
|---|---|---|---|---|
| SEQ ID #30 | HLA-C | 1 | Antisense | CATCCTGCTGCTCTCGGGAG |
| SEQ ID #8 | HLA-C | 5 | Sense | CCACAGCTCCTAGGACAGCTAGGA | a. The Strand refers to the strand of the target DNA duplex to which the amplification primer binds, i.e., an antisense primer binds to the antisense strand of the target.

The PCR reaction for the HLA-C gene was prepared as follows. Five $\mu$l of a 10 mM deoxynucleotide triphosphate (dNTP) solution (2.5 mM each of dATP, dCTP, dGTP, and dTTP), 1 $\mu$l of a 10 pMole/$\mu$l solution of the SEQ ID #13 amplification primer, 1 $\mu$l of a 10 pMole/$\mu$l solution of the SEQ ID #8 amplification primer, a volume of sterile double-distilled (dd) $H_2O$ sufficient to result in a final volume of 25 $\mu$l.

Next, the above-prepared 25 $\mu$l reaction mixture was added to a Microamp reaction tube (PE p/n N801-0533, N801-0534, N801-0540) containing one Ampliwax™ pellet (PE p/n N808-0100). The tube was capped, briefly spun in a centrifuge at 3000 rpm to remove all droplets from the side of the tube, then heated to 90° C. for 1 min to melt the Ampliwax™ pellet. The tube was then cooled to 4° C., thus forming a wax liquid barrier.

Above the wax barrier was added a solution containing 9.65 $\mu$l of dd$H_2O$, 0.35 $\mu$l of a 5 U/$\mu$l solution of of AmpliTaq™ DNA polymerase enzyme, 10 $\mu$l of the 5× concentrated PCR buffer, and 5 $\mu$l of a 10 ng/$\mu$l solution of purified genomic DNA, resulting in 25 $\mu$l total volume.

The above-prepared reaction tube was placed in a Perkin-Elmer 9600 thermal cycler, denatured at 98° C. for 20 s, then subjected to the following thermal cycle program: (i) 98° C. for 10 s, 65° C. for 2 min, where the cycle was repeated eight times; followed by (ii) 96° C. for 10 s, 65° C. for 2 min, where the cycle was repeated 32 times.

Following thermocycling, 10 $\mu$l of each of the reactions was analyzed by agarose gel electrophoresis to ensure proper PCR amplification. A 0.7% agarose gel was used containing ethidium bromide at 0.8 $\mu$g/ml and TBE buffer (89 mM Tris-HCl, 89 mM Boric Acid, 2 mM $Na_2$EDTA, pH8.3) as both the gel and running buffer. The gel was electrophoresed at 7 V/cm for 1 hr and visualized using a UV transilluminator. A band at about 2.0 kb for the HLA-C product was seen indicating successful amplification of the specific gene (sizes based on internal size standards).

EXAMPLE 6

DNA Sequencing of Exons 2 and 3 of the HLA-C Class I Gene Using the Amplification Product from Example 5

Sequencing was performed with no purification of the PCR products using the AmpliTaq® DNA polymerase FS enzyme from Perkin-Elmer (p/n 402114). The sequencing protocol used was that suggested by Perkin-Elmer with some minor modifications, e.g., ABI Prisim Dye Primer Cycle Sequencing Core Kit Protocol, Revision A, July 1995, supra. The sequencing primers shown below in Table VIII were used to sequence exons 2 and 3 of the HLA-C gene.

TABLE VIII

DNA Sequencing Primers

| SEQ ID | Gene | Exon | Strand[a] | Sequence[b] |
|---|---|---|---|---|
| SEQ ID #31 | C | 2 | Antisense | AGGAGGGTCGGGCGGGTCTCAG[c] |
| SEQ ID #12 | C | 2 | Sense | CACTCACCGGCCTCGCTCTGG |
| SEQ ID #13 | C | 3 | Sense | CCACTGCCCCTGGTACCCG | a. The Strand refers to the strand of the DNA duplex to which the sequencing primer binds.
b. Note that the primer sequences include a CAGGA leader sequence at the 5'-end that was added reduce the effect of interaction of the dye label with the primer. The CGGA leader sequence was not used for controlling hybridization specificity.
c. SEQ ID #31 did not have a CAGGA leader sequence attached to the 5'-end. Instead, only a C was added to the 5'-end.

Each of the primers in Table VIII is labeled at the 5'-end with one of the four fluorescent dyes 5-carboxy-fluorescein (FAM), 2',7'-dimethoxy-4', 5'-dichloro- 6-carboxy-fluorescene (JOE), N,N,N',N'-tetramethyl-6-carboxyrhodamine (TAMRA), and 6-carboxy-X-rhodamine (ROX), e.g., U.S. Pat. No. 4,855,225.

The following FIGS. 34–38 show examples of HLA class I typing data collected using the protocols of Examples 5 and 6.

Figure 34:
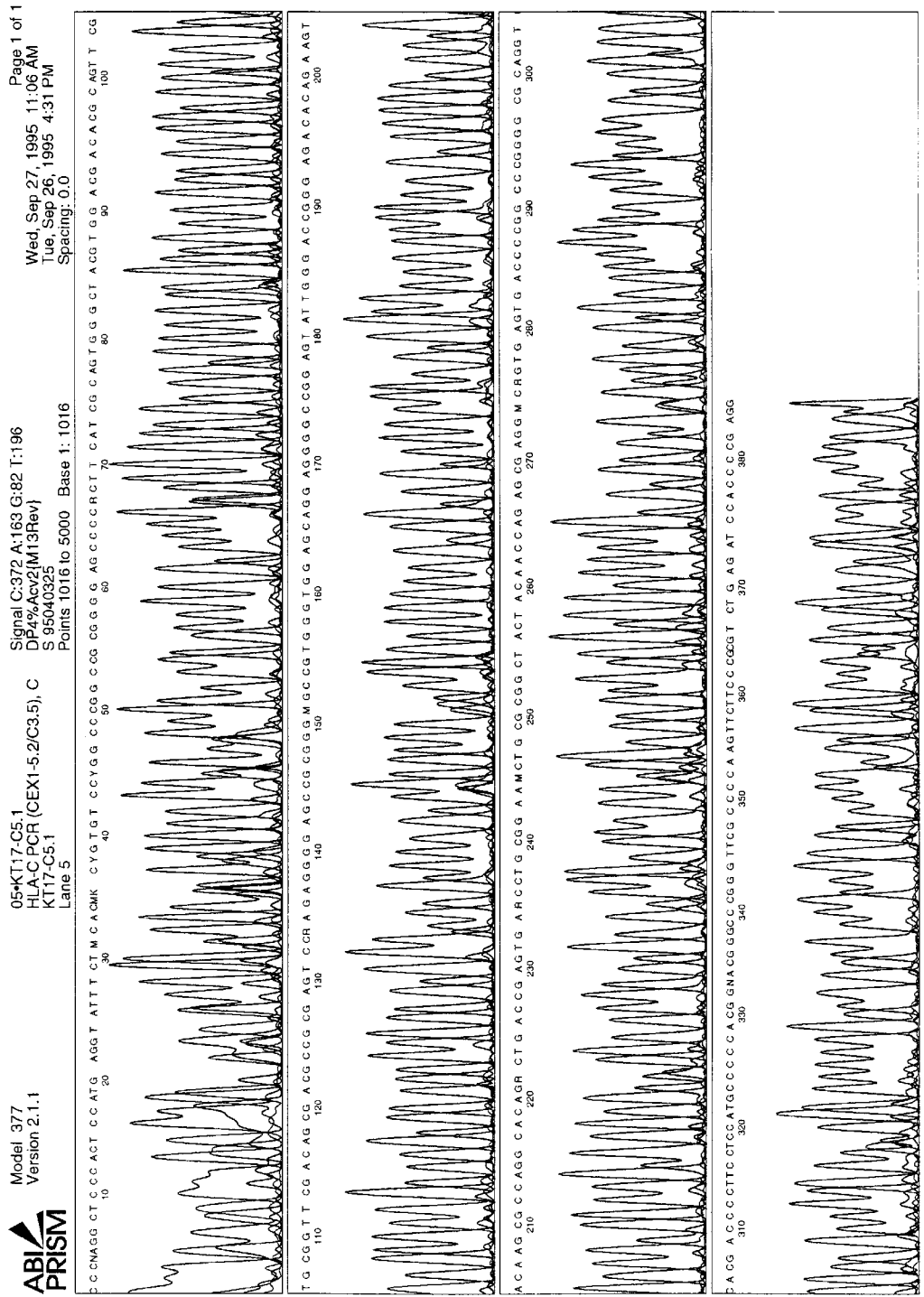
FIG. 34 is the raw sequence of the sense strand of exon 2 of the HLA-C gene.
Figure 35:
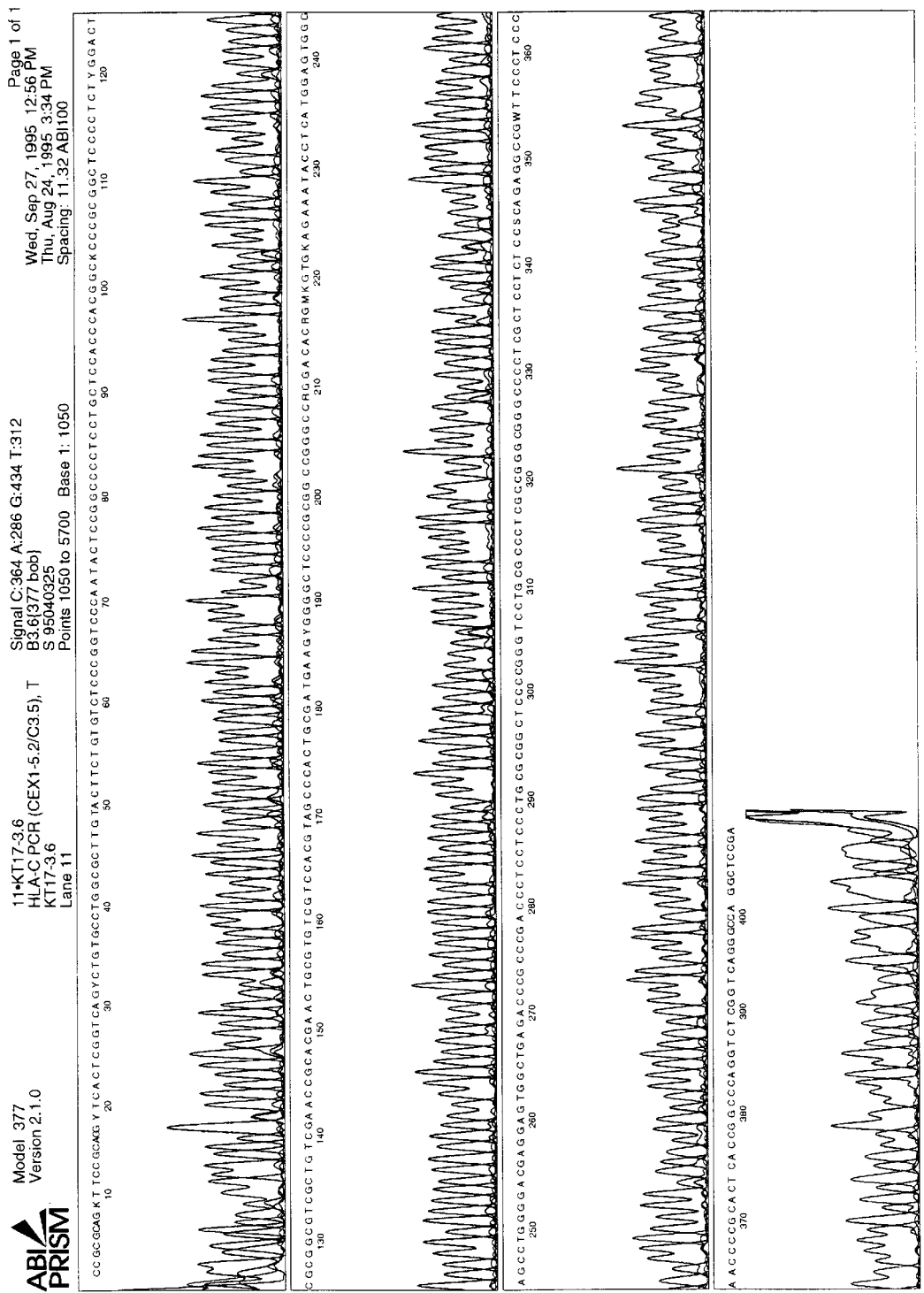
FIG. 35 is the raw sequence of the antisense strand of exon 2 of the HLA-C gene.

FIGS. 34–38 show typing data from the HLA-C class I gene. FIGS. 34 and 35 show the raw sequence of the sense strand and the antisense strand of exon 2 of the HLA-C gene, respectively. Sequencing primer SEQ ID #31 was used to obtain the sequence of the sense strand shown in FIG. 34, and sequencing primer SEQ ID #12 was used to obtain the sequence of the antisense strand shown in FIG. 35. FIGS. 36A and 36B show a sequence alignment of the data from FIGS. 34 and 35 where: line 3 and 4 are the reference sequence of the putative diploid alleles, HLA-Cw0303 and HLA-Cw0401, respectively; lines 1 and 2 are the experimentally determined sequences of the sense strand obtained from FIG. 34 and the antisense strand obtained from FIG. 35; and line 5 is a consensus sequence for the heterozygote allele (note that the line numbers 1, 2, 3, 4 and 5 refer to the numbers in the leftmost column of each of the sequence panels in FIGS. 36A and 36B).

Figure 37:
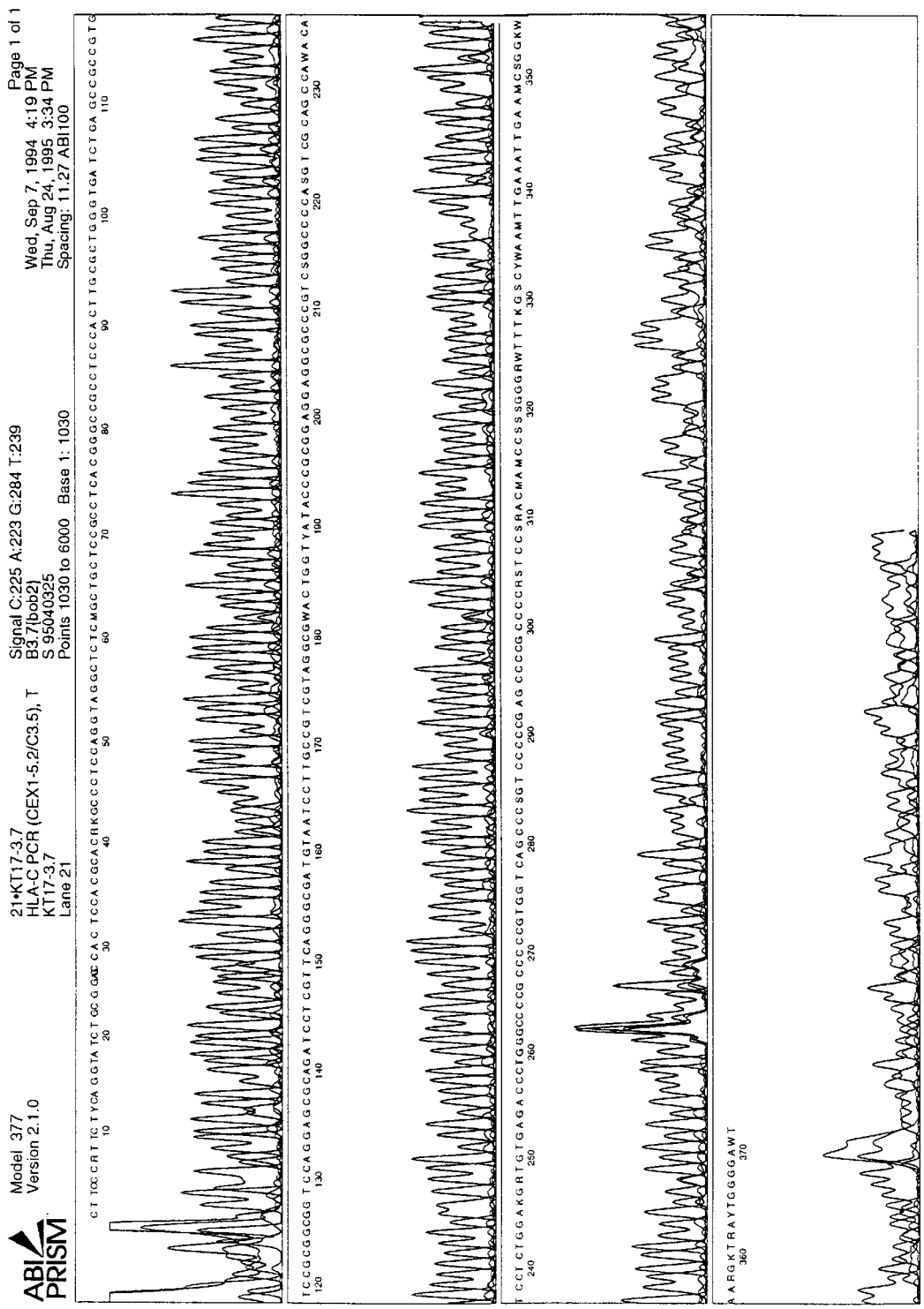
FIG. 37 is the raw sequence of the antisense strand of exon 3 of the HLA-C gene.

FIG. 37 shows the raw sequence of the antisense strand of exon 3 of the HLA-C gene. Sequencing primer SEQ ID #13 was used to obtain the sequence of the the antisense strand shown in FIG. 37. FIG. 38 shows a sequence alignment of the data from FIG. 37 where: lines 1 and 2 are the reference sequence of the putative diploid alleles, HLA-Cw0303 and HLA-Cw0401, respectively; line 3 is the experimentally determined sequence of the antisense strand obtained from FIG. 37; and line 4 is a consensus sequence for the heterozygote allele (note that the line numbers 1, 2, 3, and 4 refer to the numbers in the leftmost column of each of the sequence panels in FIG. 38).

Although only a few embodiments have been described in detail above, those having ordinary skill in the molecular biology art will clearly understand that many modifications are possible in the preferred embodiment without departing from the teachings thereof. All such modifications are intended to be encompassed within the scope of the following claims.

---

What is claimed is:

1. A method useful for typing HLA class I genes comprising the steps of:
    providing a sample DNA containing a HLA class I gene having a first exon, a second exon, and a target sequence;
    wherein the HLA class I gene is selected from the group consisting of HLA-A gene, HLA-B gene, and HLA-C gene;
    wherein the first exon is exon 1 of the HLA class I gene and the second exon is exon 5 of the HLA class I gene;
    contacting the sample DNA with a first amplification primer, the first amplification primer including a sequence complementary to the first exon of the HLA class I gene;
    contacting the sample DNA with a second amplification primer, the second amplification primer including sequence complementary to the second exon of the HLA class I gene;
    amplifying the target sequence of the sample DNA by PCR using the first and second amplification primers, thereby forming an amplicon; and
    detecting the amplicon using a sequence-specific detection means.

2. The method of claim 1 wherein the HLA class I gene is HLA-A and the first amplification primer comprises the oligonucleotide sequence CGCCGAGGATGGCCGTC (SEQ ID #1) and the second amplification primer comprises the degenerate oligonucleotide sequences GGAGAAC-CAGGCCAGCAATGATGCCC (SEQ ID #2) and GGAGAACTAGGCCAGCAATGATGCCC (SEQ ID #3).

3. The method of claim 1 wherein the HLA class I gene is HLA-B and the first amplification primer comprises the degenerate oligonucleotide sequences CCTCCTGCT-GCTCTCGGC (SEQ ID #21) and CCTCCTGCT-GCTCTCGGG (SEQ ID#22), and GCT-GCTCTGGGGGGCAG (SEQ ID #23), and the second amplification primer comprises the oligonucleotide sequence GCTCCGATGACCACAACTGCT (SEQ ID #24).

4. The method of claim 1 wherein the HLA class I gene is HLA-B and the first amplification primer comprises the oligonucleotide sequence GGCCCTGACCGAGACCTGG (SEQ ID #4) and the second amplification primer comprises the oligonucleotide sequence TCCGATGACCACAACT-GCTAGGAC (SEQ ID #5).

5. The method of claim 1 wherein the HLA class I gene is HLA-C and the first amplification primer comprises the degenerate oligonucleotide sequences GGCCCTGAC-CGAGACCTGGGC (SEQ ID #6) and GGCCCTGACCCA-GACCTGGGC (SEQ ID #7) and the second amplification primer comprises the oligonucleotide sequence CCA-CAGCTCCTAGGACAGCTAGGA (SEQ ID #8).

6. The method of claim 1 wherein the HLA class I gene is HLA-C and the first amplification primer comprises the oligonucleotide sequence CATCCTGCTGCTCTCGGGAG (SEQ ID #30) and the second amplification primer comprises the oligonucleotide sequence CCACAGCTCCTAG-GACAGCTAGGA (SEQ ID #8).

7. The method of claim 1 wherein the sequence-specific detection means is DNA sequencing.

8. The method of claim 1 wherein the sequence-specific detection means is Sanger-type DNA sequencing comprising the steps of:
contacting the amplicon with a sequencing primer;
extending the sequencing primer using a polymerase in the presense of deoxynucleotides and dideoxynucleotides, thereby forming a mixture of extension products differing in length;
separating the extension products such that extension products differing in length by a single nucleotide are resolved; and,
detecting the separated extension products.

9. The method of claim 8 wherein the sequencing primer (i) is between 10 nucleotides and 30 nucleotides in length and (ii) has a nucleotide sequence complementary to the HLA-A, HLA-B, and HLA-C genes in the nucleotide sequence regions selected from the group consisting of:
a first nucleotide sequence region from −20 nucleotides to +20 nucleotides of the 5' intron-exon border of the sense strand of exon 2;
a second nucleotide sequence region from −30 nucleotides to +20 nucleotides of the 5' intron-exon border of the sense strand of exon 3;
a third nucleotide sequence region from 31 30 nucleotides to +20 nucleotides of the 5' intron-exon border of the sense strand exon 4;
a fourth nucleotide sequence region from +30 nucleotides to −20 nucleotides of the 5' intron-exon border of the antisense strand exon 2;
a fifth nucleotide sequence region from +20 nucleotides to −20 nucleotides of the 5' intron-exon border of the antisense strand of exon 3; and
a sixth nucleotide sequence region from +40 nucleotides to −10 nucleotides of the 5' intron-exon border of the antisense strand of exon 4.

10. The method of claim 9 wherein each member of the set of sequencing primers is selected from the group consisting of:
a first sequencing primer having the sequence CTCGC-CCCCAGGCTCCCAC (SEQ ID #15);
a second sequencing primer having the sequence GCGGGGGCGGGTCCAGG (SEQ ID #16);
a third sequencing primer having the sequence CTGACTCTTCCCATCAGACCC (SEQ ID #17);
a fourth sequencing primer having the sequence CACT-CACCGGCCTCGCTCTGG (SEQ ID #18);
a fifth sequencing primer having the sequence CCACT-GCCCCTGGTACCCG (SEQ ID #19); and
a sixth sequencing primer having the sequence AGGGT-GAGGGGCTTCGGCAGCC (SEQ ID #20).

11. The method of claim 8 wherein the HLA class 1 gene is the sense strand of exon 2 of the HLA-A gene and the sequencing primer comprises the degenerate oligonucleotide sequences TCGGGCAGGTCTCAGCC (SEQ ID#25) and TCGGGCGGGTCTCAGCC (SEQ ID #26).

12. The method of claim 8 wherein the HLA class 1 gene is the antisense strand of exon 2 of the HLA-A gene and the sequencing primer comprises the oligonucleotide sequence CACTCACCGGCCTCGCTCTGG (SEQ ID #12).

13. The method of claim 8 wherein the HLA class 1 gene is the sense strand of exon 3 of the HLA-A gene and the sequencing primer comprises the degenerate oligonucleotide sequences GGGCTCGGGGGACCGGG (SEQ ID #27) and GGGCTCGGGGGACTGGG (SEQ ID #28).

14. The method of claim 8 wherein the HLA class 1 gene is the sense strand of exon 2 of the HLA-B gene and the sequencing primer comprises the oligonucleotide sequence CTCGCCCCCAGGCTCCCAC (SEQ ID #9).

15. The method of claim 8 wherein the HLA class 1 gene is the antisense strand of exon 2 of the HLA-B gene and the sequencing primer comprises the oligonucleotide sequence CACTCACCGGCCTCGCTCTGG (SEQ ID #12).

16. The method of claim 8 wherein the HLA class 1 gene is the sense strand of exon 3 of the HLA-B gene and the sequencing primer comprises the oligonucleotide sequence GCGGGGGCGGGTCCAGG (SEQ ID #10).

17. The method of claim 8 wherein the HLA class 1 gene is the antisense strand of exon 3 of the HLA-B gene and the sequencing primer comprises the oligonucleotide sequence CCACTGCCCCTGGTACCCG (SEQ ID #13).

18. The method of claim 8 wherein the HLA class 1 gene is the sense strand of exon 2 of the HLA-C gene and the sequencing primer comprises the oligonucleotide sequence AGGAGGGTCGGGCGGGTCTCAG (SEQ ID #31).

19. The method of claim 8 wherein the HLA class 1 gene is the antisense strand of exon 2 of the HLA-C gene and the sequencing primer comprises the oligonucleotide sequence CACTCACCGGCCTCGCTCTGG (SEQ ID #12).

20. The method of claim 8 wherein the HLA class 1 gene is the antisense strand of exon 3 of the HLA-C gene and the sequencing primer comprises the oligonucleotide sequence CCACTGCCCCTGGTACCCG (SEQ ID #13).

21. The method of claim 1 further comprising the step of comparing the the determined DNA sequence with the DNA sequences of known HLA types.

22. A kit for useful for typing HLA class I genes comprising:
an amplification reagent comprising:
a thermostable polymerase;
each of the A, G, C, and T deoxynucleotides;
a buffer; and
first and second amplification primers, each amplification primer being between 10 nucleotides and 30 nucleotides in length, (i) the first primer having a nucleotide sequence complementary to sequence located in exon 1 of the HLA-A gene, and (ii) the second primer having a nucleotide sequence complementary to sequence located in exon 5 of the HLA-A gene.

23. A kit useful for typing HLA class I genes comprising:
an amplification reagent comprising:
a thermostable polymerase;
each of the A, G, C, and T deoxynucleotides;
a buffer; and
first and second amplification primers, each amplification primer being between 10 nucleotides and 30 nucleotides in length, (i) the first primer having a nucleotide sequence complementary to sequence located in exon 1 of the HLA-B gene, and (ii) the second primer having a nucleotide sequence complementary to sequence located in exon 5 of the HLA-B gene.

24. A kit useful for typing HLA class I genes comprising:
an amplification reagent comprising:
a thermostable polymerase;
each of the A, G, C, and T deoxynucleotides;
a buffer; and
first and second amplification primers, each amplification primer being between 10 nucleotides and 30 nucleotides in length, (i) the first primer having a nucleotide sequence complementary to sequence located in exon 1 of the HLA-C gene, and (ii) the second primer having a nucleotide sequence complementary to sequence located in exon 5 of the HLA-C gene.

25. The kit of claim 22, 23, or 24 further comprising:
a sequencing reagent comprising:
a polymerase;
each of the A, G, C, and T deoxynucleotides;
each of the A, G, C, and T dideoxydeoxynucleotides;
a buffer, and
a set of sequencing sequencing primers wherein each member of the set of sequencing primers (i) is between 10 nucleotides and 30 nucleotides in length and (ii) has a nucleotide sequence complementary to the HLA-A, HLA-B, and HLA-C genes in the nucleotide sequence regions selected from the group consisting of:
a first nucleotide sequence region from −20 nucleotides to +20 nucleotides of the 5' intron-exon border of the sense strand of exon 2;
a second nucleotide sequence region from −30 nucleotides to +20 nucleotides of the 5' intron-exon border of he sense strand of exon 3;
a third nucleotide sequence region from −30 nucleotides to +20 nucleotides of the 5' intron-exon border of the sense strand exon 4;
a fourth nucleotide sequence region from +30 nucleotides to −20 nucleotides of the 5' intron-exon border of the antisense strand exon 2;
a fifth nucleotide sequence region from +20 nucleotides to −20 nucleotides of the 5' intron-exon border of the antisense strand of exon 3; and
a sixth nucleotide sequence region from +40 nucleotides to −10 nucleotides of the 5' intron-exon border of the antisense strand of exon 4.

26. A set of PCR amplification primers useful for amplification of the HLA-A class 1 gene comprising:
a first primer comprising the oligonucleotide sequence CGCCGAGGATGGCCGTC (SEQ ID #1); and
a second primer comprising the degenerate oligonucleotide sequences GGAGAACCAGGCCAGCAATGATGCCC (SEQ ID #2) and GGAGAACTAGGCCAGCAATGATGCCC (SEQ ID #3).

27. A set of PCR amplification primers useful for amplification of the HLA-B class 1 gene comprising:
a first primer comprising the oligonucleotide sequence GGCCCTGACCGAGACCTGG (SEQ ID #4); and
a second primer comprising the oligonucleotide sequence TCCGATGACCACAACTGCTAGGAC (SEQ ID #5).

28. A set of PCR amplification primers useful for amplification of the HLA-B class 1 gene comprising:
a first primer comprising the degenerate oligonucleotide sequences CCTCCTGCTGCTCTCGGC (SEQ ID #21), and CCTCCTGCTGCTCTCGGGA (SEQ ID #22), and GCTGCTCTGGGGGGCAG (SEQ ID #23); and
a second primer comprising the oligonucleotide sequence GCTCCGATGACCACAACTGCT (SEQ ID #24).

29. A set of PCR amplification primers useful for amplification of the HLA-C class 1 gene comprising:
a first primer comprising the degenerate oligonucleotide sequences GGCCCTGACCCAGACCTGGGC (SEQ ID #6), and GGCCCTGACCCAGACCTGGGC (SEQ ID #7); and
a second primer comprising the oligonucleotide sequence CCACAGCTCCTAGGACAGCTAGGA (SEQ ID #8).

30. A set of PCR amplification primers useful for amplification of the HLA-C class 1 gene comprising:
a first primer comprising the oligonucleotide sequence CATCCTGCTGCTCTCGGGAG (SEQ ID #30); and
a second primer comprising the oligonucleotide sequence CCACAGCTCCTAGGACAGCTAGGA (SEQ ID #8).

31. A sequencing primer useful for sequencing exon 2 of HLA-A, -B, or -C class 1 genes comprising the oligonucleotide sequence CTCGCCCCCAGGCTCCCAC (SEQ ID #9).

32. A sequencing primer useful for sequencing exon 2 of HLA-A, -B, or -C class 1 genes comprising the oligonucleotide sequence CACTCACCGGCCTCGCTCTGG (SEQ ID #12).

33. A sequencing primer useful for sequencing exon 2 of HLA-A, -B, or -C class 1 genes comprising the degenerate oligonucleotide sequences TCGGGCAGGTCTCAGCC (SEQ ID #25) and TCGGGCGGGTCTCAGCC (SEQ ID #26).

34. A sequencing primer useful for sequencing exon 2 of HLA-A, -B, or -C class 1 genes comprising the oligonucleotide sequence AGGAGGGTCGGGCGGGTCTCAG (SEQ ID #31).

35. A sequencing primer useful for sequencing exon 3 of HLA-A, -B, or -C class 1 genes comprising the oligonucleotide sequence GCGGGGGCGGGTCCAGG (SEQ ID #10).

36. A sequencing primer useful for sequencing exon 3 of HLA-A, -B, or -C class 1 genes comprising the oligonucleotide sequence CCACTGCCCCTGGTACCCG (SEQ ID #13).

37. A sequencing primer useful for sequencing exon 3 of HLA-A, -B, or -C class 1 genes comprising the oligonucleotide sequence GAGGCGCCCCGTGGC (SEQ ID #29).

38. A sequencing primer useful for sequencing exon 3 of HLA-A, -B, or -C class 1 genes comprising the degenerate oligonucleotide sequences GGGCTCGGGGGACCGGG (SEQ ID #27) and GGGCTCGGGGGACTGGG (SEQ ID #28).

39. A sequencing primer useful for sequencing exon 4 of HLA-A, -B, or -C class 1 genes comprising the oligonucleotide sequence CTGACTCTTCCCATCAGACCC (SEQ ID #11).

40. A sequencing primer useful for sequencing exon 4 of HLA-A, -B, or -C class 1 genes comprising the oligonucleotide sequence AGGGTGAGGGGCTTCGGCAGCC (SEQ ID #14).

41. A sequencing primer useful for sequencing exon 3 of HLA-A, -B, or -C class 1 genes comprising the oligonucleotide sequence GGGCTGACCACGGGGGCGGGGCCCAG (SEQ ID #32).

* * * * *